(12) United States Patent
Galdi et al.

(10) Patent No.: US 9,580,458 B2
(45) Date of Patent: Feb. 28, 2017

(54) POLYMORPHIC FORM OF SODIUM HYODEOXYCHOLATE (NAHDC) AND ITS PREPARATION PROCESS

(71) Applicant: PRODOTTI CHIMICI E ALIMENTARI S.P.A., Basaluzzo (AL) (IT)

(72) Inventors: Gianluca Galdi, Pieve Ligure (IT); Paolo Sacco, Campo Ligure (IT); Valeria Ferrari, Basaluzzo (IT)

(73) Assignee: PRODOTTI CHIMICI E ALIMENTARI S.P.A., Basaluzzo (AL) (IT)

( * ) Notice: Subject to any disclaimer, the term of this patent is extended or adjusted under 35 U.S.C. 154(b) by 0 days.

(21) Appl. No.: 15/025,569

(22) PCT Filed: Oct. 2, 2014

(86) PCT No.: PCT/IB2014/065016
§ 371 (c)(1),
(2) Date: Mar. 29, 2016

(87) PCT Pub. No.: WO2015/049657
PCT Pub. Date: Apr. 9, 2015

(65) Prior Publication Data
US 2016/0222053 A1     Aug. 4, 2016

(30) Foreign Application Priority Data
Oct. 3, 2013   (EP) ..................................... 13187285

(51) Int. Cl.
*C07J 9/00*       (2006.01)
(52) U.S. Cl.
CPC .................................... *C07J 9/005* (2013.01)

(58) Field of Classification Search
CPC ............................... C07J 9/005; A61K 31/575
See application file for complete search history.

(56) References Cited

U.S. PATENT DOCUMENTS 7,982,062 B2 * 7/2011 Allegrini .................. C07J 9/005
                                                           552/548
8,304,383 B2   11/2012 Zadini et al.

FOREIGN PATENT DOCUMENTS

EP          1903050 A2    3/2008

OTHER PUBLICATIONS

Anonymous: "ICE", Dec. 3, 2012, Retrieved from the Internet: http://www.iceitaly.com/products15.htm.
Search Report and Written Opinion of PCT/IB2014/065016 of Jan. 29, 2015.

* cited by examiner

*Primary Examiner* — Sudhakar Katakam
(74) *Attorney, Agent, or Firm* — Silvia Salvadori, P.C.; Silvia Salvadori

(57) ABSTRACT

The object of the present invention is a new anhydrous polymorphic crystalline form of sodium hyodeoxycholate (NaHDC) named as form II (FII) and the process for preparing it. Such a process makes it possible to obtain sodium hyodeoxycholate in the anhydrous polymorphic form II (FII), with high chemical and polymorphic purity. The invention also describes the anhydrous polymorphic crystalline forms of NaHDC named as form I (FI) and form III (FIII), the hydrated forms of NaHDC named as SI and SII, crystalline forms of NaHDC, respectively hydrated with four and eight water molecules and the amorphous form.

22 Claims, 62 Drawing Sheets

| Pos. [°2Th.] | Rel. Int. [%] |
|---|---|
| 6.94 | 81.00 |
| 9.84 | 82.46 |
| 13.92 | 91.77 |
| 14.56 | 74.09 |
| 15.40 | 100.00 |
| 16.22 | 25.02 |
| 18.80 | 18.71 |
| 20.13 | 71.52 |
| 21.81 | 3.61 |
| 23.30 | 27.51 |
| 25.49 | 21.66 |
| 27.94 | 4.43 |
| 28.42 | 6.34 |
| 30.28 | 4.35 |
| 31.17 | 2.55 |
| 32.06 | 5.49 |
| 32.62 | 3.32 |
| 33.81 | 5.40 |
| 36.12 | 4.80 |
| 37.84 | 4.94 |
| 38.97 | 2.01 |

Fig. 2

| Anhydrous FII 25°C | | Anhydrous FII 100°C | | Anhydrous FII 220°C | | Anhydrous FI 25°C | | Anhydrous FII 280°C | |
|---|---|---|---|---|---|---|---|---|---|
| Pos. [°2Th.] | Rel. Int. [%] | Pos. [°2Th.] | Rel. Int. [%] | Pos. [°2Th.] | Rel. Int. [%] | Pos. [°2Th.] | Rel. Int. [%] | Pos. [°2Th.] | Rel. Int. [%] |
| 6.94 | 81.00 | 6.71 | 53.64 | 6.87 | 39.33 | 6.17 | 100.00 | 5.9621 | 18.81 |
| 9.84 | 82.46 | 9.76 | 40.98 | 9.72 | 48.00 | 7.82 | 17.89 | 7.7879 | 16.56 |
| 13.92 | 91.77 | 13.956 | 33.97 | 13.88 | 51.65 | 9.50 | 60.46 | 9.4451 | 33.58 |
| 14.56 | 74.09 | 14.49 | 56.08 | 14.52 | 56.70 | 11.77 | 95.16 | 11.6404 | 34.68 |
| 15.40 | 100.00 | 15.38 | 59.46 | 15.33 | 72.84 | 12.35 | 37.63 | 12.2060 | 5.46 |
| 16.22 | 25.02 | 16.16 | 23.67 | 16.06 | 27.06 | 13.18 | 4.77 | 13.5677 | 4.95 |
| 18.80 | 18.71 | 18.77 | 17.79 | 18.82 | 19.66 | 14.74 | 99.19 | 14.6188 | 81.41 |
| 20.13 | 71.52 | 19.99 | 100.00 | 19.93 | 100.00 | 15.05 | 72.87 | 15.0291 | 100.00 |
| 21.81 | 3.61 | 21.85 | 4.61 | 21.81 | 4.86 | 16.39 | 24.78 | 16.2186 | 26.79 |
| 23.30 | 27.51 | 23.29 | 24.77 | 23.16 | 24.26 | 17.03 | 26.52 | 17.0287 | 7.59 |
| 25.49 | 21.66 | 25.30 | 16.69 | 25.44 | 20.25 | 17.78 | 58.55 | 17.7553 | 60.55 |
| 27.94 | 4.43 | 27.85 | 5.45 | 27.87 | 4.96 | 18.51 | 19.20 | 18.4833 | 2.91 |
| 28.42 | 6.34 | 28.60 | 6.99 | 28.48 | 6.94 | 19.63 | 74.97 | 19.5136 | 58.83 |
| 30.28 | 4.35 | 30.43 | 5.97 | 30.25 | 5.72 | 21.71 | 39.32 | 21.5669 | 27.33 |
| 31.17 | 2.55 | 31.18 | 4.82 | 31.37 | 4.94 | 22.91 | 6.21 | 23.9125 | 2.64 |
| 32.06 | 5.49 | 32.09 | 8.55 | 31.99 | 8.98 | 24.04 | 6.82 | 24.0384 | 2.78 |
| 32.62 | 3.32 | 32.52 | 6.12 | 32.51 | 5.80 | 25.53 | 29.51 | 25.4518 | 13.21 |
| 33.81 | 5.40 | 33.79 | 7.28 | 33.81 | 7.28 | 26.57 | 12.24 | 26.4668 | 7.88 |
| 36.12 | 4.80 | 36.13 | 7.96 | 36.10 | 7.27 | 28.40 | 14.77 | 28.4220 | 9.41 |
| 37.84 | 4.94 | 37.79 | 8.95 | 37.85 | 7.97 | 29.51 | 16.17 | 29.4914 | 12.22 |
| 38.97 | 2.01 | 38.94 | 6.30 | 38.91 | 5.88 | 31.96 | 20.29 | 31.8451 | 11.75 |
| | | | | | | 34.60 | 3.97 | 34.5397 | 5.65 |
| | | | | | | 36.14 | 2.08 | 36.0526 | 5.93 |
| | | | | | | 37.19 | 7.48 | 37.1826 | 8.13 |
| | | | | | | 38.32 | 3.34 | 38.5175 | 5.89 |

Fig. 5

| Peak (cm$^{-1}$) |
|:---:|
| 3254.5 |
| 2958.9 |
| 2917.3 |
| 2874.6 |
| 2851.0 |
| 1560.7 |
| 1474.9 |
| 1454.7 |
| 1443.6 |
| 1394.2 |
| 1347.4 |
| 1292.9 |
| 1261.0 |
| 1245.7 |
| 1218.6 |
| 1161.2 |
| 1002.3 |

Fig. 8

|  | Target RH (%) | Change in mass (%) - ref | | Hysteresis |
| --- | --- | --- | --- | --- |
|  |  | Sorption | Desorption |  |
| Cycle 1 | 0.0 | 0.00 | -0.10 |  |
|  | 10.0 | 0.17 | 0.64 | 0.47 |
|  | 20.0 | 0.31 | 1.57 | 1.26 |
|  | 30.0 | 0.45 | 12.46 | 12.01 |
|  | 40.0 | 0.61 | 18.98 | 18.38 |
|  | 50.0 | 0.84 | 33.91 | 33.07 |
|  | 60.0 | 1.13 | 34.16 | 33.03 |
|  | 70.0 | 1.98 | 34.40 | 32.41 |
|  | 80.0 | 20.06 | 34.66 | 14.60 |
|  | 90.0 | 35.14 | 35.14 |  |

Fig. 11

|  | Target RH (%) | Change in Mass (%) - ref | | Hysteresis |
|---|---|---|---|---|
|  |  | Sorption | Desorption |  |
| Cycle 1 | 0.0 | 0.00 | 2.74 |  |
|  | 10.0 | 0.17 | 4.02 | 3.85 |
|  | 20.0 | 0.32 | 6.36 | 6.04 |
|  | 30.0 | 0.47 | 10.18 | 9.71 |
|  | 40.0 | 0.64 | 15.46 | 14.82 |
|  | 50.0 | 0.86 | 17.55 | 16.69 |
|  | 60.0 | 1.19 | 24.80 | 23.62 |
|  | 70.0 | 5.95 | 31.60 | 25.65 |
|  | 80.0 | 33.71 | 39.26 | 5.55 |
|  | 90.0 | 45.49 | 45.49 |  |

Fig. 13

| Pos. [°2Th.] | Rel. Int. [%] |
|---|---|
| 6.17 | 100.00 |
| 7.82 | 17.89 |
| 9.50 | 60.46 |
| 11.77 | 95.16 |
| 12.35 | 37.63 |
| 13.18 | 4.77 |
| 14.74 | 99.19 |
| 15.05 | 72.87 |
| 16.39 | 24.78 |
| 17.03 | 26.52 |
| 17.78 | 58.55 |
| 18.51 | 19.20 |
| 19.63 | 74.97 |
| 21.71 | 39.32 |
| 22.91 | 6.21 |
| 24.04 | 6.82 |
| 25.53 | 29.51 |
| 26.57 | 12.24 |
| 28.40 | 14.77 |
| 29.51 | 16.17 |
| 31.96 | 20.29 |
| 34.60 | 3.97 |
| 36.14 | 2.08 |
| 37.19 | 7.48 |
| 38.32 | 3.34 |

Fig. 15

| Anhydrous FI 25°C | | Anhydrous FI 100°C | | Anhydrous FI 200°C | | Anhydrous FI 280°C | |
|---|---|---|---|---|---|---|---|
| Pos. [°2Th.] | Rel. Int. [%] | Pos. [°2Th.] | Rel. Int. [%] | Pos. [°2Th.] | Rel. Int. [%] | Pos. [°2Th.] | Rel. Int. [%] |
| 6.17 | 100.00 | 5.9790 | 83.47 | 5.9447 | 89.57 | 5.9348 | 100.00 |
| 7.82 | 17.89 | 7.6806 | 21.33 | 7.8598 | 17.87 | 7.8239 | 20.45 |
| 9.50 | 60.46 | 9.4296 | 46.90 | 9.3900 | 52.93 | 9.3990 | 51.31 |
| 11.77 | 95.16 | 11.6086 | 69.34 | 11.6861 | 78.60 | 11.6344 | 74.26 |
| 12.35 | 37.63 | 12.2282 | 10.65 | 12.1432 | 21.19 | 12.1881 | 23.69 |
| 13.18 | 4.77 | 14.2214 | 35.36 | 13.5495 | 3.95 | 13.5494 | 2.55 |
| 14.74 | 99.19 | 14.5952 | 100.00 | 14.6245 | 100.00 | 14.6503 | 91.46 |
| 15.05 | 72.87 | 15.3797 | 56.32 | 15.0870 | 78.72 | 15.0226 | 70.53 |
| 16.39 | 24.78 | 16.2547 | 23.72 | 16.3122 | 30.37 | 16.3741 | 23.64 |
| 17.03 | 26.52 | 17.0236 | 14.19 | 17.1101 | 16.49 | 17.0144 | 15.88 |
| 17.78 | 58.55 | 17.6375 | 43.64 | 17.7204 | 68.94 | 17.7399 | 62.98 |
| 18.51 | 19.20 | 18.4765 | 7.05 | 18.5086 | 7.94 | 18.4080 | 9.59 |
| 19.63 | 74.97 | 19.5173 | 63.64 | 19.5267 | 75.36 | 19.5556 | 77.06 |
| 21.71 | 39.32 | 21.6584 | 26.50 | 21.6205 | 33.20 | 21.6571 | 38.18 |
| 22.91 | 6.21 | 22.8994 | 2.39 | 22.8832 | 1.94 | 22.8633 | 3.47 |
| 24.04 | 6.82 | 24.0652 | 2.87 | 24.0781 | 2.51 | 24.0127 | 3.62 |
| 25.53 | 29.51 | 25.4425 | 17.11 | 25.5148 | 23.05 | 25.4825 | 25.89 |
| 26.57 | 12.24 | 26.5714 | 3.63 | 26.6986 | 6.95 | 26.6005 | 9.28 |
| 28.40 | 14.77 | 28.4784 | 12.42 | 28.2791 | 11.10 | 28.3251 | 16.04 |
| 29.51 | 16.17 | 29.4061 | 15.34 | 29.4720 | 13.10 | 29.5009 | 17.22 |
| 31.96 | 20.29 | 31.9670 | 17.12 | 31.9617 | 14.81 | 32.0127 | 18.62 |
| 34.60 | 3.97 | 34.5676 | 8.25 | 34.5954 | 1.64 | 34.4968 | 7.84 |
| 36.14 | 2.08 | 36.0224 | 9.43 | 36.0286 | 2.83 | 36.0574 | 6.02 |
| 37.19 | 7.48 | 37.1266 | 13.23 | 37.1917 | 7.97 | 37.2095 | 11.74 |
| 38.32 | 3.34 | 5.9790 | 83.47 | 38.4170 | 6.88 | 38.1314 | 8.61 |

Fig. 19

| Peak (cm$^{-1}$) |
| --- |
| 3259.0 |
| 2932.5 |
| 2916.1 |
| 2893.2 |
| 2867.4 |
| 2848.1 |
| 1557.5 |
| 1454.8 |
| 1435.3 |
| 1421.5 |
| 1405.8 |
| 1387.1 |
| 1334.2 |
| 1311.5 |
| 1084.6 |
| 1060.3 |

Fig. 21

|  | Target RH (%) | Change in Mass (%) - ref | | Hysteresis |
| --- | --- | --- | --- | --- |
|  |  | Sorption | Desorption |  |
| Cycle 1 | 0.0 | 0.00 | -0.16 |  |
|  | 10.0 | 0.35 | 0.67 | 0.32 |
|  | 20.0 | 1.08 | 1.62 | 0.54 |
|  | 30.0 | 2.19 | 11.82 | 9.63 |
|  | 40.0 | 2.84 | 19.33 | 16.50 |
|  | 50.0 | 3.67 | 33.59 | 29.92 |
|  | 60.0 | 4.60 | 34.03 | 29.43 |
|  | 70.0 | 14.84 | 34.34 | 19.50 |
|  | 80.0 | 34.56 | 34.70 | 0.14 |
|  | 90.0 | 35.22 | 35.22 |  |

Fig. 24

|  | Target RH (%) | Change in Mass (%) - ref | | Hysteresis |
|---|---|---|---|---|
|  |  | Sorption | Desorption |  |
| Cycle 1 | 0.0 | 0.00 | 0.17 |  |
|  | 10.0 | 0.35 | 1.09 | 0.75 |
|  | 20.0 | 1.10 | 1.98 | 0.88 |
|  | 30.0 | 2.15 | 3.23 | 1.08 |
|  | 40.0 | 2.80 | 16.70 | 13.90 |
|  | 50.0 | 3.32 | 17.47 | 14.16 |
|  | 60.0 | 3.91 | 19.74 | 15.83 |
|  | 70.0 | 7.58 | 33.56 | 25.97 |
|  | 80.0 | 34.06 | 37.39 | 3.33 |
|  | 90.0 | 43.22 | 43.22 |  |

Fig. 26

| Pos. [°2Th.] | Rel. Int. [%] |
|---|---|
| 5.54 | 7.20 |
| 6.07 | 15.49 |
| 9.33 | 1.41 |
| 10.20 | 23.18 |
| 11.24 | 6.98 |
| 11.85 | 8.54 |
| 12.63 | 2.97 |
| 13.21 | 13.06 |
| 14.63 | 100.00 |
| 14.96 | 54.48 |
| 15.78 | 22.90 |
| 16.13 | 29.99 |
| 16.91 | 12.76 |
| 17.69 | 7.25 |
| 18.13 | 8.64 |
| 18.62 | 25.50 |
| 19.16 | 42.19 |
| 19.56 | 9.29 |
| 20.65 | 6.58 |
| 21.60 | 7.89 |
| 22.22 | 7.43 |
| 23.01 | 2.07 |
| 23.67 | 2.83 |
| 24.24 | 7.47 |
| 24.61 | 3.64 |
| 25.98 | 4.41 |
| 26.54 | 2.75 |
| 29.08 | 2.04 |
| 31.87 | 0.88 |
| 33.06 | 1.02 |
| 33.85 | 1.27 |
| 37.97 | 1.52 |
| 38.81 | 1.30 |

Fig. 30

| Peak (cm⁻¹) |
|---|
| 2929.5 |
| 2863.5 |
| 1556.8 |
| 1408.0 |
| 1373.6 |
| 1038.2 |
| 1027.8 |
| 997.7 |
| 852.1 |
| 917.4 |

Fig. 34

| Pos. [°2Th.] | Rel. Int. [%] |
|---|---|
| 4.92 | 100.00 |
| 8.99 | 3.17 |
| 9.94 | 3.81 |
| 12.34 | 9.91 |
| 14.89 | 11.16 |
| 15.70 | 14.71 |
| 16.46 | 30.28 |
| 17.72 | 35.75 |
| 19.31 | 7.89 |
| 19.75 | 12.22 |
| 21.01 | 44.65 |
| 23.35 | 8.73 |
| 24.64 | 6.30 |
| 25.78 | 41.25 |
| 26.85 | 3.35 |
| 28.03 | 10.90 |
| 28.80 | 3.39 |
| 29.93 | 41.42 |
| 32.37 | 4.35 |
| 33.18 | 6.09 |
| 34.88 | 2.85 |
| 35.74 | 9.30 |
| 38.13 | 6.30 |

Fig. 36

| Pos. [°2Th.] | Rel. Int. [%] |
|---|---|
| 4.88 | 16.60 |
| 8.81 | 8.23 |
| 12.19 | 11.41 |
| 12.82 | 34.39 |
| 15.30 | 65.85 |
| 15.47 | 91.58 |
| 16.24 | 100.00 |
| 17.45 | 80.23 |
| 19.12 | 14.46 |
| 19.52 | 12.95 |
| 20.05 | 8.45 |
| 20.83 | 20.37 |
| 21.68 | 6.00 |
| 22.32 | 7.74 |
| 22.95 | 9.10 |
| 23.35 | 7.66 |
| 24.35 | 6.09 |
| 25.30 | 36.25 |
| 25.98 | 6.29 |
| 26.64 | 7.76 |
| 27.33 | 10.35 |
| 27.64 | 15.54 |
| 28.07 | 10.75 |
| 28.56 | 2.48 |
| 29.03 | 1.44 |
| 29.75 | 22.40 |
| 30.19 | 3.93 |
| 30.94 | 2.16 |
| 31.41 | 3.21 |
| 32.17 | 2.84 |
| 33.30 | 6.55 |
| 33.90 | 3.83 |
| 34.66 | 4.16 |
| 35.47 | 3.81 |
| 36.15 | 2.43 |
| 36.99 | 3.87 |
| 37.54 | 5.04 |
| 38.04 | 3.61 |
| 39.08 | 0.73 |

Fig. 41

| Pos. [°2Th.] | Rel. Int. [%] |
|---|---|
| 5.54 | 89.29 |
| 15.58 | 100 |

Fig. 46

| Peak (cm$^{-1}$) |
| --- |
| 3316.7 |
| 2928.4 |
| 2863.6 |
| 1557.3 |
| 1446.2 |
| 1404.4 |
| 1374.4 |
| 1334.4 |
| 1316.9 |
| 1038.4 |
| 1029.3 |
| 998.7 |
| 952.8 |
| 912.2 |

Fig. 50

|  | Target RH (%) | Change in Mass (%) - ref | | Hysteresis |
|---|---|---|---|---|
|  |  | Sorption | Desorption |  |
| Cycle 1 | 0.0 | 0.00 | -1.71 |  |
|  | 10.0 | 2.27 | -1.18 | -3.44 |
|  | 20.0 | 4.06 | -0.51 | -4.57 |
|  | 30.0 | 5.74 | 12.06 | 6.32 |
|  | 40.0 | 8.56 | 16.70 | 8.13 |
|  | 50.0 | 12.65 | 32.26 | 19.61 |
|  | 60.0 | 17.09 | 32.47 | 15.38 |
|  | 70.0 | 21.84 | 32.66 | 10.82 |
|  | 80.0 | 33.15 | 32.89 | -0.27 |
|  | 90.0 | 33.34 | 33.34 |  |

Fig. 52

|  | Target RH (%) | Change in Mass (%) - ref | | Hysteresis |
|---|---|---|---|---|
|  |  | Sorption | Desorption |  |
| Cycle 1 | 0.0 | 0.00 | -0.76 |  |
|  | 10.0 | 1.30 | 0.10 | -1.20 |
|  | 20.0 | 2.96 | 1.15 | -1.81 |
|  | 30.0 | 5.69 | 12.23 | 6.54 |
|  | 40.0 | 8.06 | 18.85 | 10.79 |
|  | 50.0 | 9.53 | 33.21 | 23.68 |
|  | 60.0 | 11.72 | 33.53 | 21.81 |
|  | 70.0 | 14.18 | 33.83 | 19.66 |
|  | 80.0 | 27.43 | 34.19 | 6.76 |
|  | 90.0 | 34.76 | 34.76 |  |

Fig. 57

| HPLC Analysis (HPLC/RI) | |
|---|---|
| HPLC Equipment | Perkin Elmer 200 Series |
| Autosampler | Perkin Elmer 200 Series |
| Pump | Perkin Elmer HPLC Pump 200 series |
| Data Acquisition hardware | Perkin Elmer Totalchrom Client/Server |
| RI Detector | Perkin Elmer Refraction Index 200 series |
| Column | Inertsil ODS / ODS2 4µm, 250mm |
| Column Temperature | 40 ± 0.1°C |
| Flow | 0.8 ml/min |
| Injection | 150µl |
| Run Time | 90 min. |
| Mobile Phase | $NaH_2PO_4$ 0.005 M (pH 3.0); $CH_3CN$; $CH_3OH$ 37:30:40 (v:v:v) |

Fig. 60

| Pos. [°2Th.] | Rel. Int. [%] |
|---|---|
| 6.94 | 81.00 |
| 9.84 | 82.46 |
| 13.92 | 91.77 |
| 14.56 | 74.09 |
| 15.40 | 100.00 |
| 16.22 | 25.02 |
| 18.80 | 18.71 |
| 20.13 | 71.52 |
| 21.81 | 3.61 |
| 23.30 | 27.51 |
| 25.49 | 21.66 |
| 27.94 | 4.43 |
| 28.42 | 6.34 |
| 30.28 | 4.35 |
| 31.17 | 2.55 |
| 32.06 | 5.49 |
| 32.62 | 3.32 |
| 33.81 | 5.40 |
| 36.12 | 4.80 |
| 37.84 | 4.94 |
| 38.97 | 2.01 |

Fig. 62

POLYMORPHIC FORM OF SODIUM HYODEOXYCHOLATE (NAHDC) AND ITS PREPARATION PROCESS

This application is a U.S. national stage of PCT/IB2014/065016 filed on 2 Oct. 2014, which claims priority to and the benefit of European Application No. 13187285.5, filed on 3 Oct. 2013, the contents of which are incorporated herein by reference in their entirety.

The object of the present invention is a new anhydrous polymorphic crystalline form of sodium hyodeoxycholate (NaHDC) named as form II (FII) and the process for preparing it.

Such a process makes it possible to obtain sodium hyodeoxycholate in the anhydrous polymorphic crystalline form II (FII), with high chemical and polymorphic purity.

The invention also describes the anhydrous polymorphic crystalline forms of NaHDC named as form I (FI) and form III (FIII), the hydrated forms of NaHDC named as SI and SII, crystalline forms of NaHDC respectively hydrated with four and eight water molecules and the amorphous form.

Sodium hyodeoxycholate, i.e. sodium 3α,6α-dihydroxy-5β,-cholan-24-oate, which has the following chemical formula (formula I) and CAS RN 10421-49-5, is particularly useful in the treatment and/or prevention of atherosclerotic disease, as for example described in U58304383 to AtheroNova Operations Inc.:

Formula I

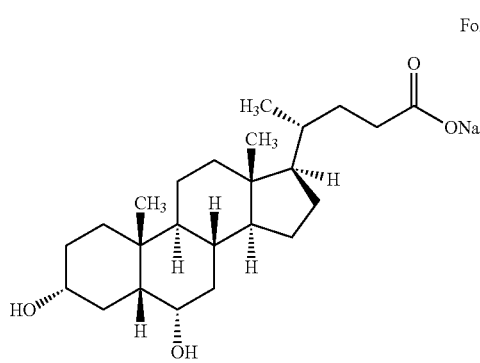

The corresponding acid, i.e. 3α,6α-dihydroxy-5β-cholan-24-oic acid of formula II, commonly named hyodeoxycholic acid (HDCA), is the most important bile acid present in porcine bile, in terms of percentage abundance, around 40% by weight over the total amount of bile acids present in porcine bile.

Formula II

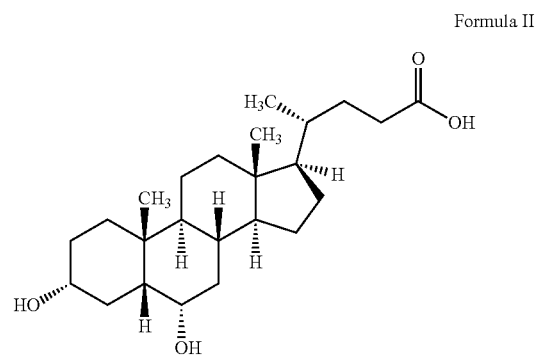

Currently, HDCA is extracted from porcine bile with a process that contemplates various steps: first of all a bile saponification process is carried out, i.e. a base hydrolysis process of the bile in an aqueous solution, necessary to de-conjugate the bile acids that are normally present in the bile in the form of glycoderivatives and tauroderivatives.

Then there is a separation step of the bile acids, which at this point are present in the solution in the form of free carboxylic acids, from the fatty acids: this "fat removal" step is carried out with solvents such as ketones, acetates, hydrocarbons, mixtures of hydrocarbons such as petroleum ether, mixtures of alkanes, alkenes, aromatic hydrocarbons, etc.

Thereafter, the HDCA is separated by precipitation by an aqueous solution or by a hydroalcoholic solution in the form of magnesium salt or other salts. Alcohols suitable for the separation of these salts are alcohols with chain C1—C5, like for example methanol, ethanol, 1-propyl alcohol (1-propanol), isopropyl alcohol 2-propanol, 1-butanol, 2-butanol, 2-pentanol, etc.

The magnesium salt of hyodeoxycholic acid, of formula III and abbreviated as (HDC) 2Mg, must be further purified through various reprecipitation steps by aqueous or hydroalcoholic solutions like those described above, to be able to obtain, after acidification, HDCA with a chemical purity comprised between 80 and 90%.

Formula III

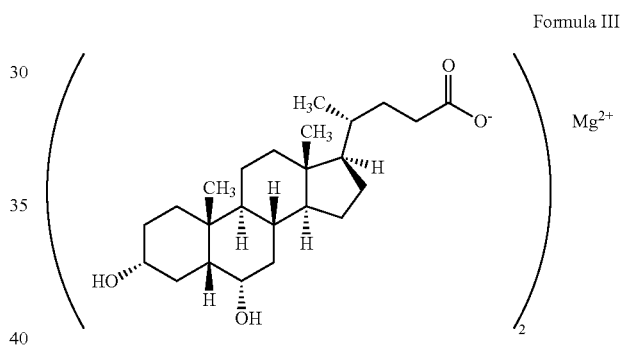

This procedure and analogous processes are described in patent documents U.S. Pat. No. 4,186,143 to Canada Packers Ltd, U.S. Pat. No. 5,349,074 to Erregierre Industria Chimica S.p.A., U.S. Pat. No. 7,982,062B2 to Dipharma S.p.A., WO2007/069814 A1 and WO2007/078039 A1 both to Dae Woong Pharma.

The prior art has never described crystalline forms of HDCA or of its salts, and in particular no information has even been published on the existence of polymorphism for the sodium salt of hyodeoxycholic acid. For example, the article of Nonappa et al., Crystal Growth & Design, Vol 9, N. 11 (2009) p. 4710-4719 characterises some polymorphs that are found in natural bile acids, but indicating that for the samples of HDCA available on the market no polymorphs were found.

The purpose of the present invention is therefore to obtain a new stable polymorphic form of the sodium salt of hyodeoxycholic acid (polymorphic form FII) and a process for preparing it, capable of providing said form of NaHDC with a high chemical and polymorphic purity.

The polymorphic form FII, unlike all of the other described forms of NaHDC, has a very high stability in the humidity sorption cycle in isotherm at 25° C. and at 40° C. (see FIGS. 10,11,12 and 13). The polymorphic form FII has non-hygroscopic behaviour unlike all other polymorphic forms (see FIGS. 27,28 and 58) found: it is thus very stable and easily stored. This behaviour is absolutely unusual for the other sodium salts of bile acids, which have the common problem of high hygroscopicity and therefore consequent difficulty of conservation due to their instability.

Polymorphic form FII has a very high and surprising stability towards humidity in isotherm at 25° C. and at 40° C.

Indeed, in sorption at 25° C. the sample is stable up to 70% RH (Relative Humidity) (at 70% RH it shows an increase in weight of less than 2%). After 70% RH it absorbs humidity and at 90% RH there is a change in weight of about 35%. Hereafter we will indicate the results of humidity stability studies of this polymorphic form FII.

From DVS (Dynamic Vapour Sorption) analysis at 25° C., polymorphic form FI is less stable than polymorphic form FII: polymorphic form FII is stable in sorption at 25° C. up to 70% RH, whereas polymorphic form FI already at 20% RH shows a change in weight of about 2% (see FIG. 27). Also from DVS analysis at 40° C., polymorphic form FI is less stable than polymorphic form FII: polymorphic form FII is stable in sorption at 40° C. up to 70% RH, whereas polymorphic form FI already at 30% RH shows a change in weight of about 2% (see FIG. 28). Moreover, NaHDC mixture (mixture of different polymorphic forms that is obtained before final reprecipitation, which is carried out for example in anhydrous acetone), from DVS analysis at 25° C. is less stable than polymorphic form FII (see FIG. 58). Polymorphic form FII is stable in sorption up to about 70% RH, whereas NaHDC mixture already at 20% RH shows a change in weight of about 3%.

The process of the invention makes it possible to obtain the polymorphic form FII of NaHDC with a defined particle size (granulometry) and optimal chemical-physical characteristics for the use of NaHDC as pharmaceutical active ingredient, particularly in the treatment and/or prevention of atherosclerotic disease.

Further advantages of the process of the present invention are its reproducibility, its scale-up potential and the possibility of obtaining the active ingredient in polymorphic form FII as powder with an optimal morphology (crystal habit) for all the operating parameters that can influence the final bioavailability, i.e. the bulk density (apparent density), the density after compacting (tapped density), compressibility, rate of dissolution, la fluidity and hygroscopicity of the powder.

Since the process of the invention makes it possible to obtain the polymorphic form FII of sodium hyodeoxycholate in the desired granulometry, operations such as grinding and micronization of the active ingredient, usually carried out to improve its bioavailability through the increase in its rate of dissolution, can be advantageously avoided.

In this way, as well as the obvious energy saving, it is possible to avoid operations that can affect the chemical and/or polymorphic purity of a product, like for example micronization, which can potentially create variable percentages of amorph in the crystalline forms already formed (known amorphization process).

Finally, the present process makes it possible to obtain the polymorphic form FII of sodium hyodeoxycholate with a high yield.

The overall yield of the process from $3\alpha,6\alpha$-dihydroxy-$5\beta$-cholan-24-oic acid (HDCA) of formula II (hyodeoxycholic acid—HDCA) having a chemical purity comprised between 80 and 90% to sodium salt of hyodeoxycholic acid (NaHDC) having a chemical purity comprised between 99.5%-99.9% and in polymorphically pure form, polymorphic form FII is comprised in the range between 65.0%-85.0% (weight/weight) and 62.0%-80.0% (mol/mol).

HDCA is purified through salification with Magnesium salts $(HDC)_2Mg$ in deionized/drinking water or hydroalcohol solution: $(HDC)_2Mg$ precipitates while the salts of the impurities remain dissolved. The acid function is restored by acidifying an aqueous suspension of $(HDC)_2Mg$. The process is repeated iteratively until a purity of between 99.5%-99.9% is achieved, with yields comprised between 90%-95% (w/w, mol/mol) for the first salification process and with yields comprised between 95%-98% (w/w, mol/mol) for the subsequent salification processes. HDCA thus purified is dissolved in an aqueous sodium hydroxide solution and then precipitated with acetone, with a yield comprised between 85%-95% (w/w) and 80%-90% (mol/mol). This product (NaHDC), once dried, is suspended in acetone under heat until the polymorphic form FII is obtained with yields comprised between 90%-95% (w/w, mol/mol). The overall yield of the process is comprised between 65%-85% (w/w) and 62%-80% (mol/mol).

The polymorphic form object of the present invention, i.e. the polymorphic form FII, is anhydrous and is the most thermodynamically stable form at room temperature and does not interconvert into the other forms in the process conditions of the present invention. Moreover, when it has been inserted into the formulation of a medicinal product, it is stable over time, since no interconversion into the other polymorphic forms of sodium hyodeoxycholate that will be described hereafter is observed. As already indicated, unlike the other forms, it has a very strong and surprising stability with regard to humidity, having non-hygroscopic behaviour, unlike all other forms thereof, which is unusual for a sodium salt belonging to the category of bile acids.

The term crystalline polymorph or polymorph is used in the present invention to refer to a specific crystalline form of a pharmaceutical active ingredient that can be characterised through analytical methods such as X-ray Powder Diffraction (XPRD), FT-IR/ATR spectroscopy (Fourier-Transform Infrared-Attenuated Total Reflectance Spectroscopy), FT-RAMAN spectroscopy, Differential Scanning calorimetry (DSC), Thermo-Gravimetry Analysis (TGA) and Dynamic Vapour Sorption (DVS) analysis in isotherm at 25° C. and at 40° C. In the present invention the polymorphic form FII, can, without distinction, be named by one of the following terms:
polymorphic form II, or
polymorphic form II (FII), or
crystalline polymorphic form II, or
crystalline polymorphic form II (FII), or
anhydrous crystalline polymorphic form II, or
anhydrous crystalline polymorphic form II (FII), or
crystalline form FII, or
anhydrous crystalline form FII.

The polymorphic form FI can, without distinction, be named by one of the following terms:
polymorphic form I, or
polymorphic form I (FI), or
crystalline polymorphic form I, or
crystalline polymorphic form I (FI), or
anhydrous crystalline polymorphic form I, or
anhydrous crystalline polymorphic form I (FI), or
crystalline form FI, or
anhydrous crystalline form FI.

The polymorphic form FIII can, without distinction, be named by one of the following terms:
polymorphic form III, or
polymorphic form III (FIII), or crystalline polymorphic form III, or
crystalline polymorphic form III (FIII), or
anhydrous crystalline polymorphic form III, or
anhydrous crystalline polymorphic form III (FIII), or
crystalline form FIII, or
anhydrous crystalline form FIII.

Similarly, for the hydrated polymorphic form used as an example SI, it is possible to use, without distinction, a term of the type:
hydrated polymorphic form SI, or
hydrated crystalline polymorphic form SI.

For the hydrated polymorphic form used as an example SII, it is possible to use, without distinction, a term of the type:
hydrated polymorphic form SI, or
hydrated crystalline polymorphic form SI.

BRIEF DESCRIPTION OF THE FIGURES

FIG. 2: shows the 2 theta values of the XPRD peaks of FIG. 1 of the anhydrous crystalline form II (FII), together with the corresponding relative intensity. The peaks highlighted in bold are the characteristic peaks of the form FII.

FIG. 5: comparison between list of XRPD peaks anhydrous form FII at 25° C., anhydrous form FII at 100° C., anhydrous form FII at 220° C., anhydrous form FII at 280° C. towards XRPD anhydrous form FI at 25° C. of NaHDC of FIG. 4.

FIG. 8: shows the values in $cm^{-1}$ of the characteristic peaks FT-IR/ATR of FIG. 7 of the anhydrous crystalline form FII of NaHDC.

FIG. 11: isotherm ratio at 25° C. of FIG. 10 anhydrous crystalline form FII of NaHDC.

FIG. 13: isotherm ratio at 40° C. of FIG. 12 anhydrous crystalline form FII of NaHDC.

FIG. 15: shows the 2 theta values of the XPRD peaks of FIG. 14 of the anhydrous crystalline form FI, together with the corresponding relative intensity. The peaks in bold can be defined as characteristic of Form I (FII)

FIG. 19: comparison between list of peaks Anhydrous form FI, XRPD anhydrous form FI at 25° C., XRPD anhydrous form FI at 100° C., XRPD anhydrous form FI at 200° C., XRPD anhydrous form FI at 280° C. of NaHDC of FIG. 18.

FIG. 21: shows the values in $cm^{-1}$ of the characteristic peaks FT-IR/ATR of FIG. 20 of the anhydrous crystalline form FI of NaHDC.

FIG. 24: isotherm ratio at 25° C. of FIG. 23 Anhydrous crystalline form FI of NaHDC.

FIG. 26: isotherm ratio at 40° C. of FIG. 25 anhydrous crystalline form FI of NaHDC.

FIG. 30: shows the 2 theta values of the XPRD peaks of FIG. 29 of the anhydrous crystalline form FIII, together with the corresponding relative intensity. The peaks in bold can be defined as characteristic of Form III (FIII).

FIG. 34: shows the values in $cm^{-1}$ of the characteristic peaks FT-IR/ATR of FIG. 33 of the anhydrous crystalline form FIII of NaHDC.

FIG. 36: shows the 2 theta values of the XPRD peaks of FIG. 35 of the hydrated crystalline form SI, together with the corresponding relative intensity. The peaks in bold can be defined as characteristic of Form SI (SI).

FIG. 41: shows the 2 theta values of the XPRD peaks of FIG. 40 of the hydrated crystalline form SII, together with the corresponding relative intensity. The peaks in bold can be defined as characteristic of Form SII (SII).

FIG. 46: shows the 2 theta values of the XPRD peaks of FIG. 45 of the amorphous form of NaHDC, together with the corresponding relative intensity. The peaks in bold can be defined as characteristic of the amorphous Form.

FIG. 50: shows the values in $cm^{-1}$ of the characteristic peaks FT-IR/ATR of FIG. 49 of the amorphous form of NaHDC.

FIG. 52: isotherm ratio at 25° C. of FIG. 51 amorphous form of NaHDC.

FIG. 57: isotherm ratio at 25° C. of FIG. 56 of NaHDC mixture.

FIG. 60: HPLC method for analysing the purity of the polymorphic form FII of NaHDC in acid form as HDCA and instrument conditions.

FIG. 62: shows the 2 theta values of the XPRD peaks of FIG. 61 of the polymorphic form FII of NaHDC, together with the corresponding relative intensity. The peaks in bold can be defined as characteristic of Form II (FII).

The object of the present invention is therefore sodium hyodeoxycholate in the polymorphic form FII. The amount of water in the NaHDC crystal polymorphic form FII is less than 1%, preferably less than 0.6% and even more preferably it is less than 0.4%, where said percentages are in relation to the total weight of the crystal.

Figure 1:
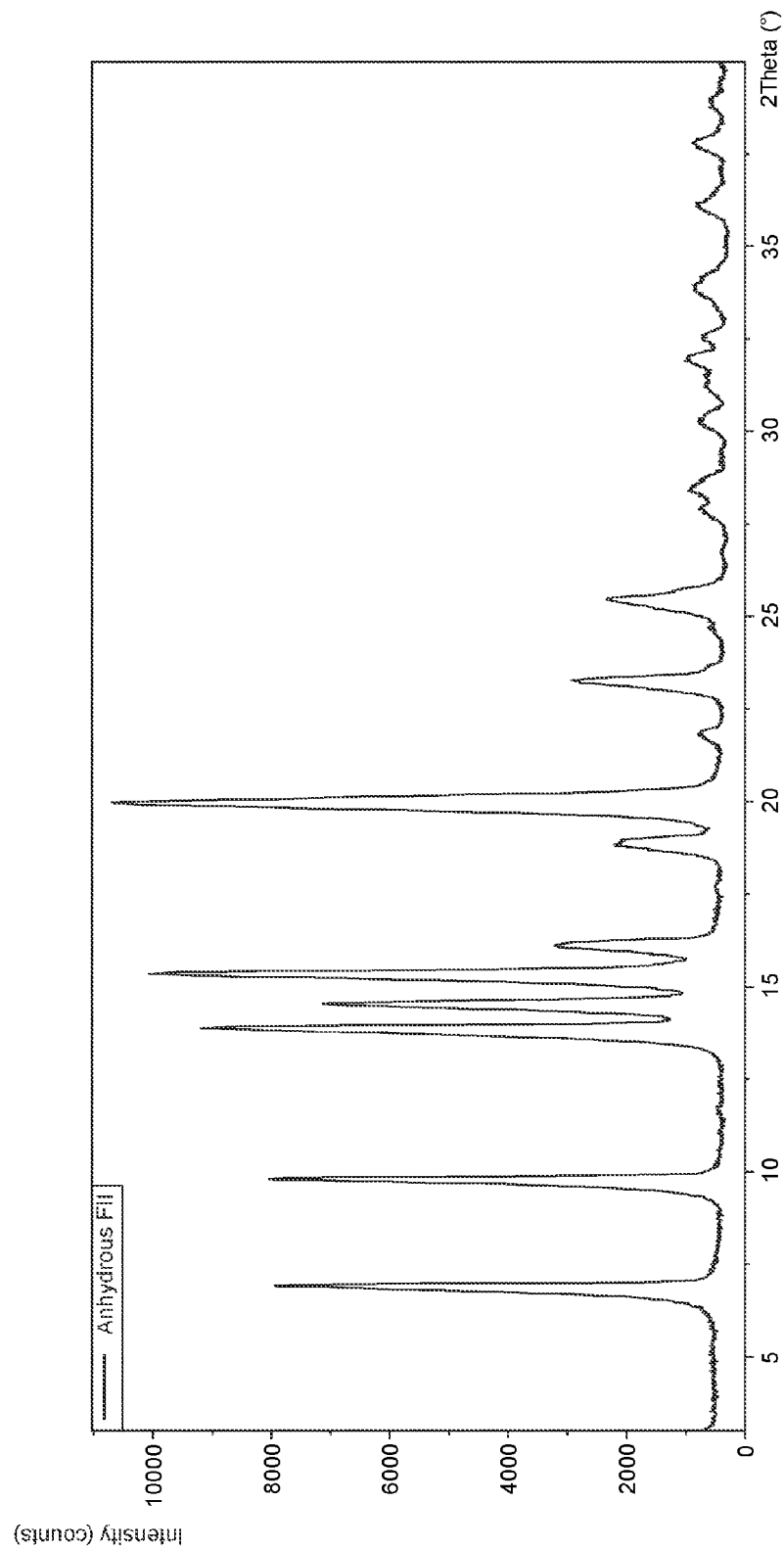
FIG. 1: shows the X-ray powder diffractogram (XPRD) of the anhydrous crystalline form II (FII) of NaHDC.
Figure 3:
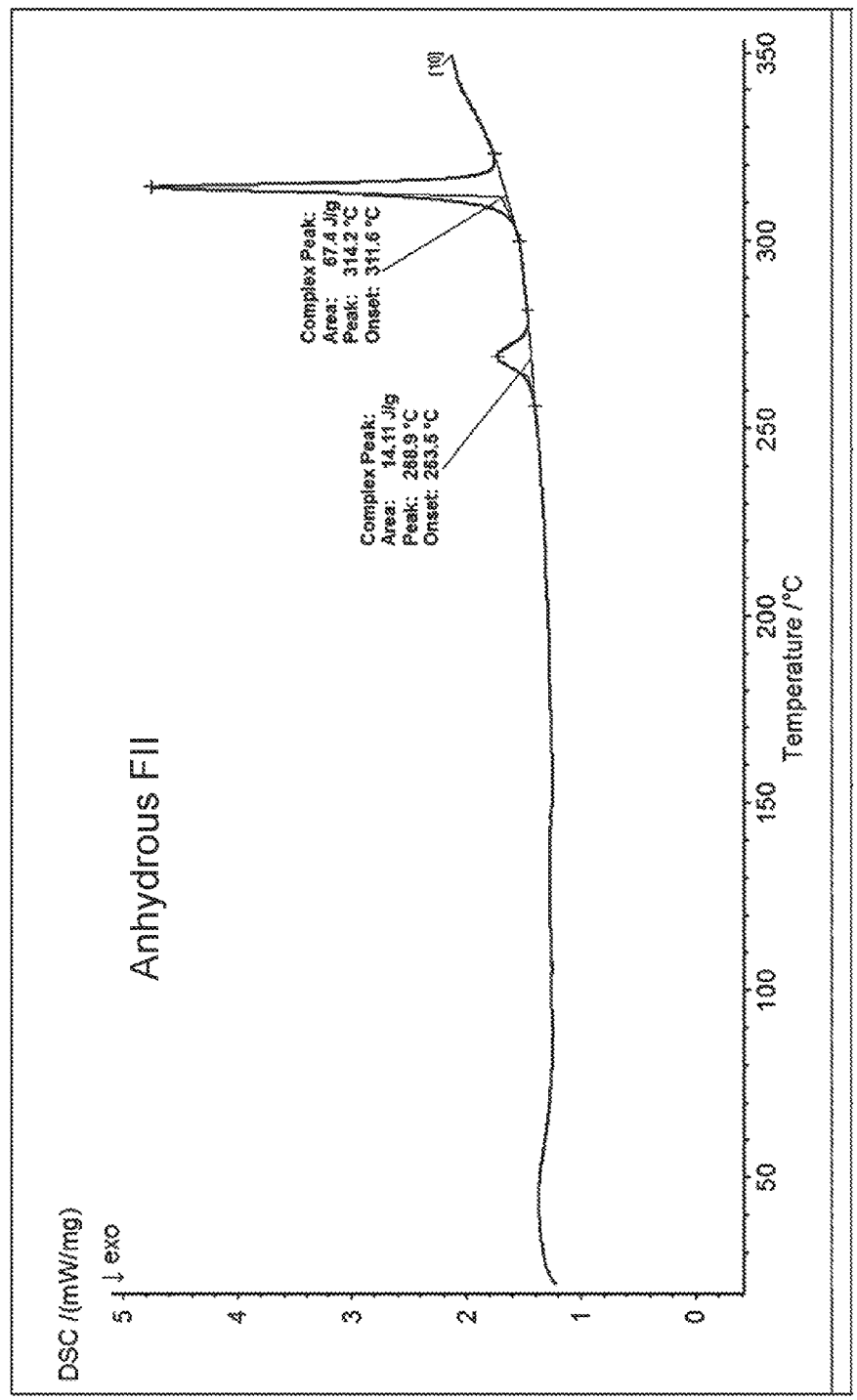
FIG. 3: shows the differential scanning calorimetry (DSC) profile of the anhydrous crystalline form II (FII) of NaHDC.
Figure 6:
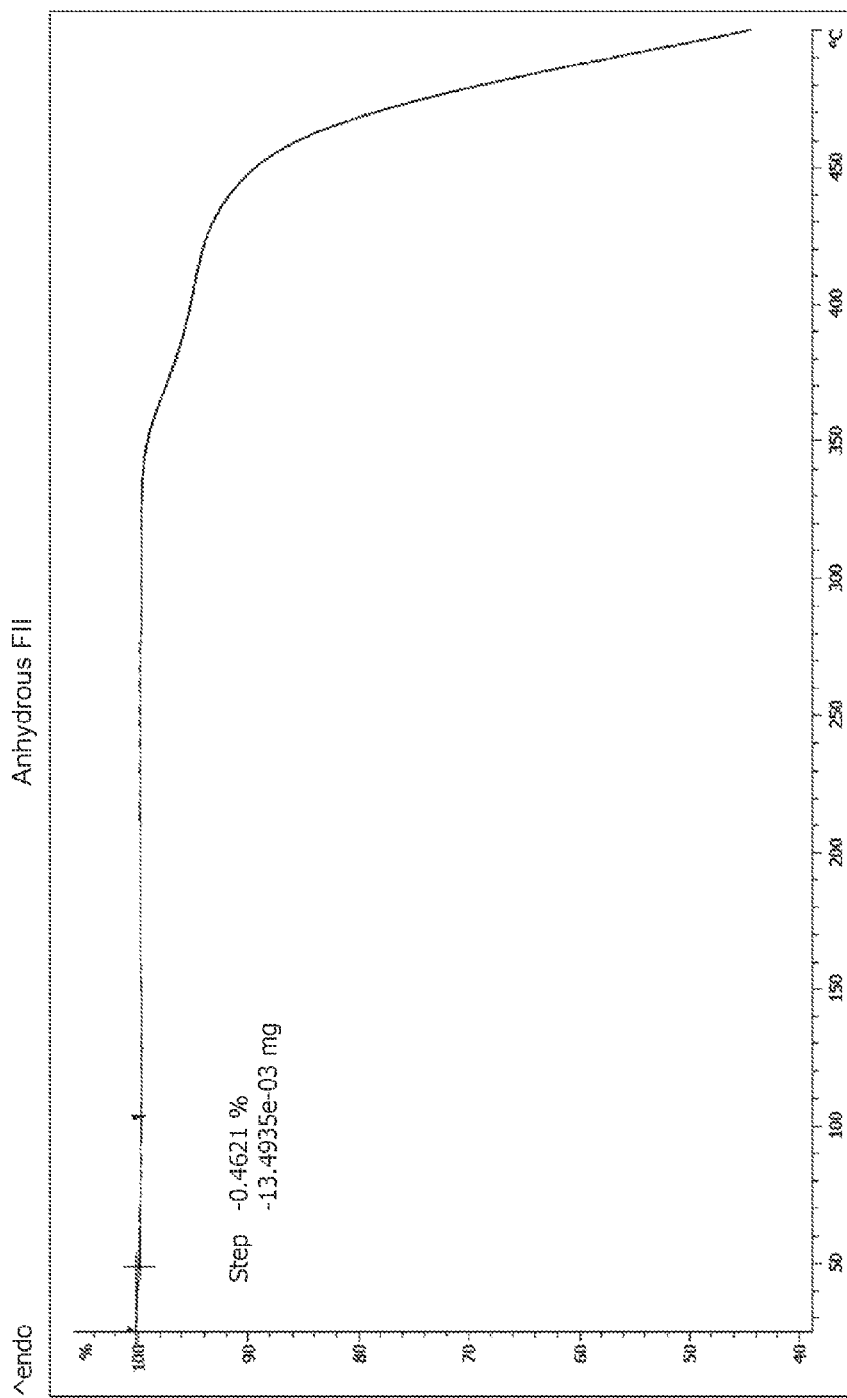
FIG. 6: shows the thermogravimetric profile (TGA) of the anhydrous crystalline form FII of NaHDC.
Figure 7:
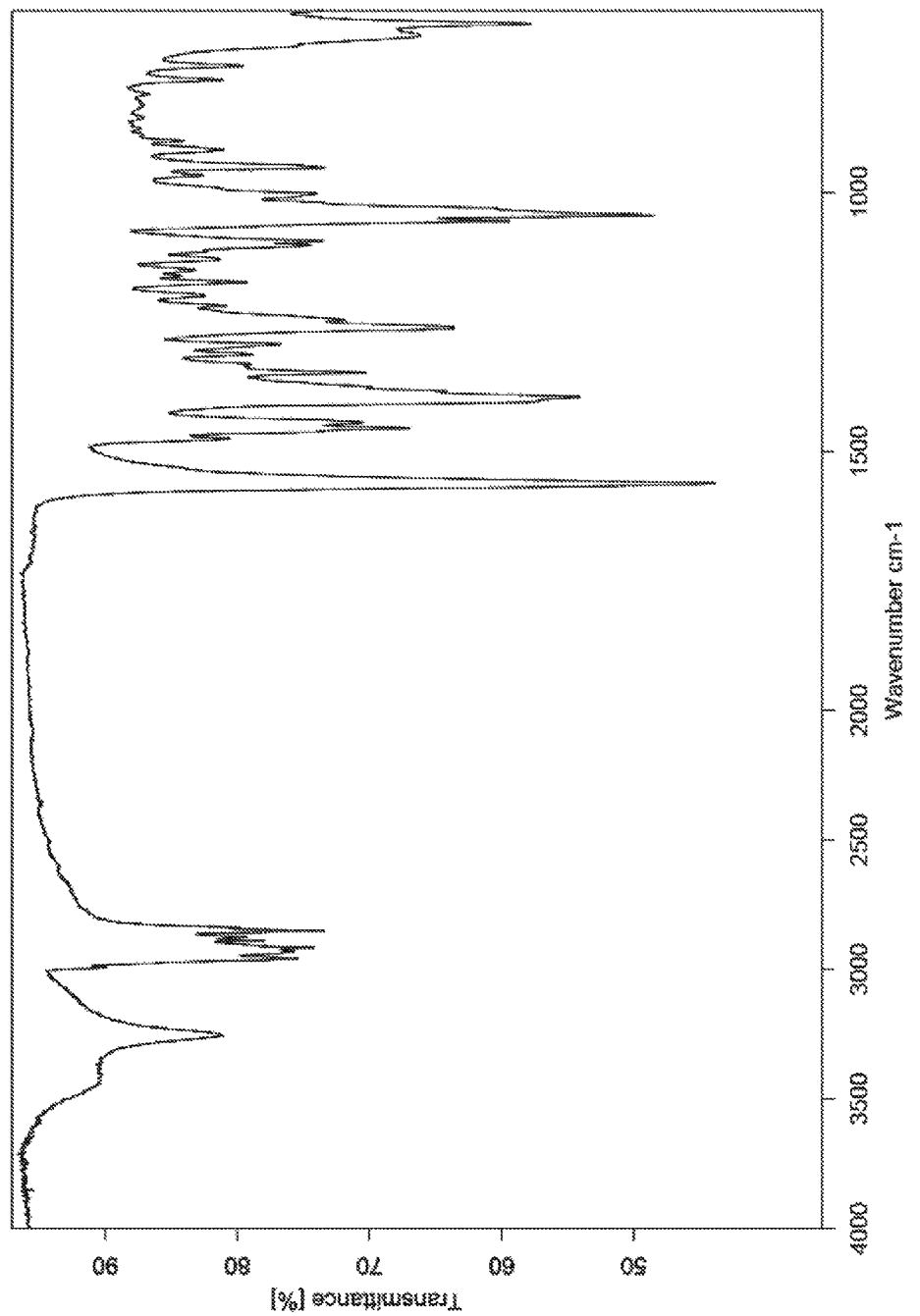
FIG. 7: shows the FT-IR/ATR spectrum of the polymorphic form FII of NaHDC.
Figure 9:
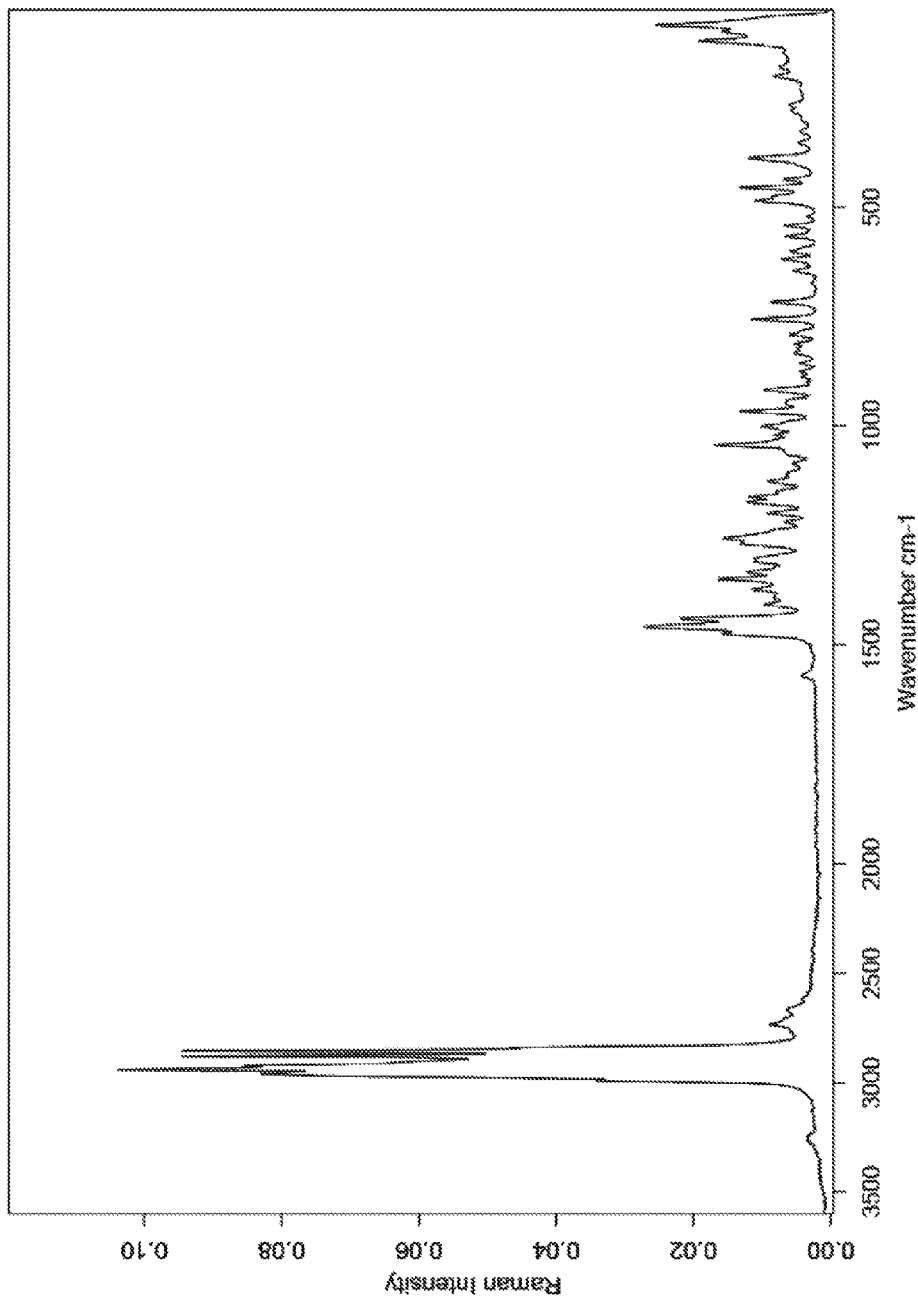
FIG. 9: shows the FT-RAMAN spectrum of the anhydrous crystalline form FII of NaHDC.
Figure 10:
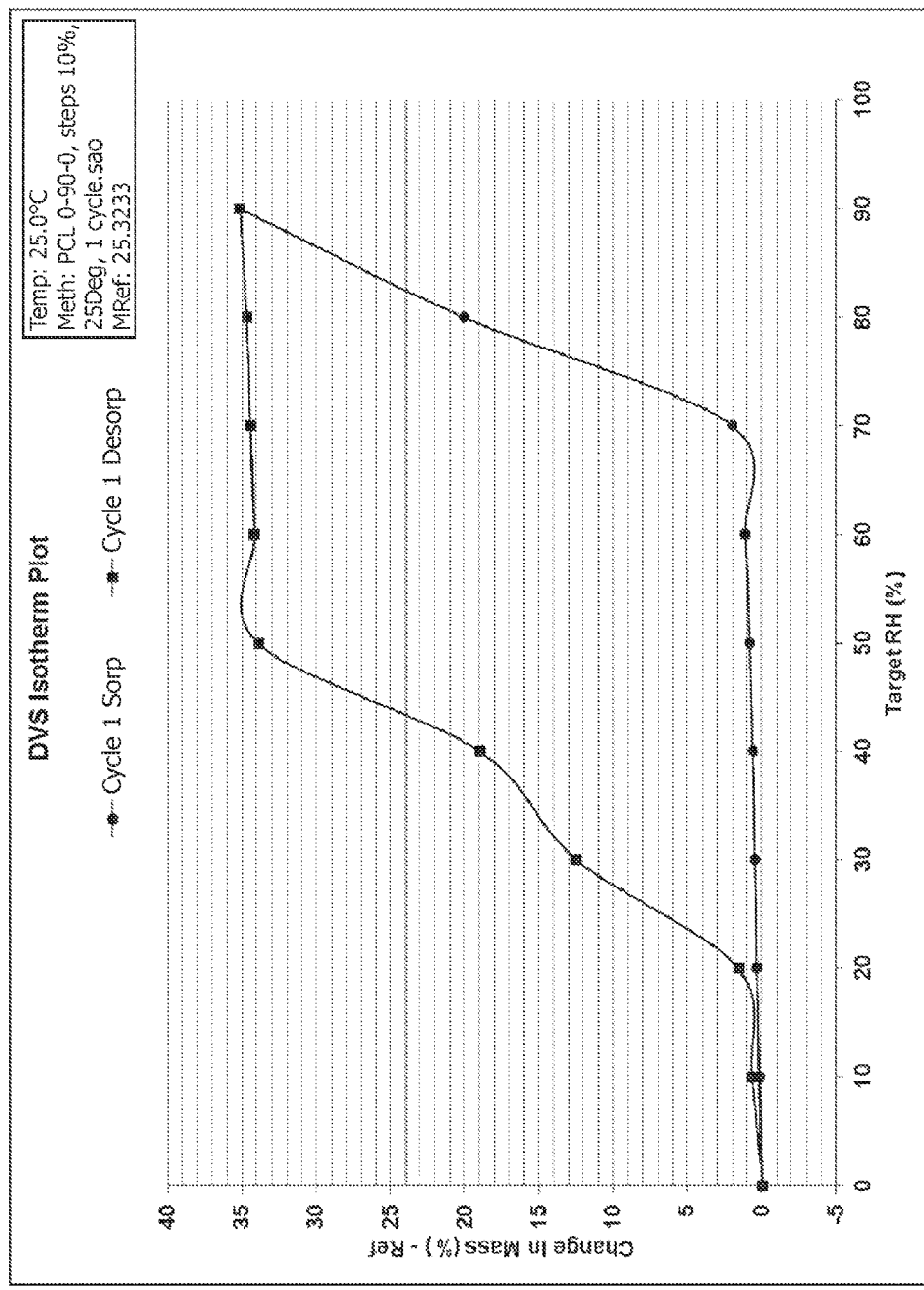
FIG. 10: isotherm at 25° C. anhydrous crystalline form FII of NaHDC.
Figure 12:
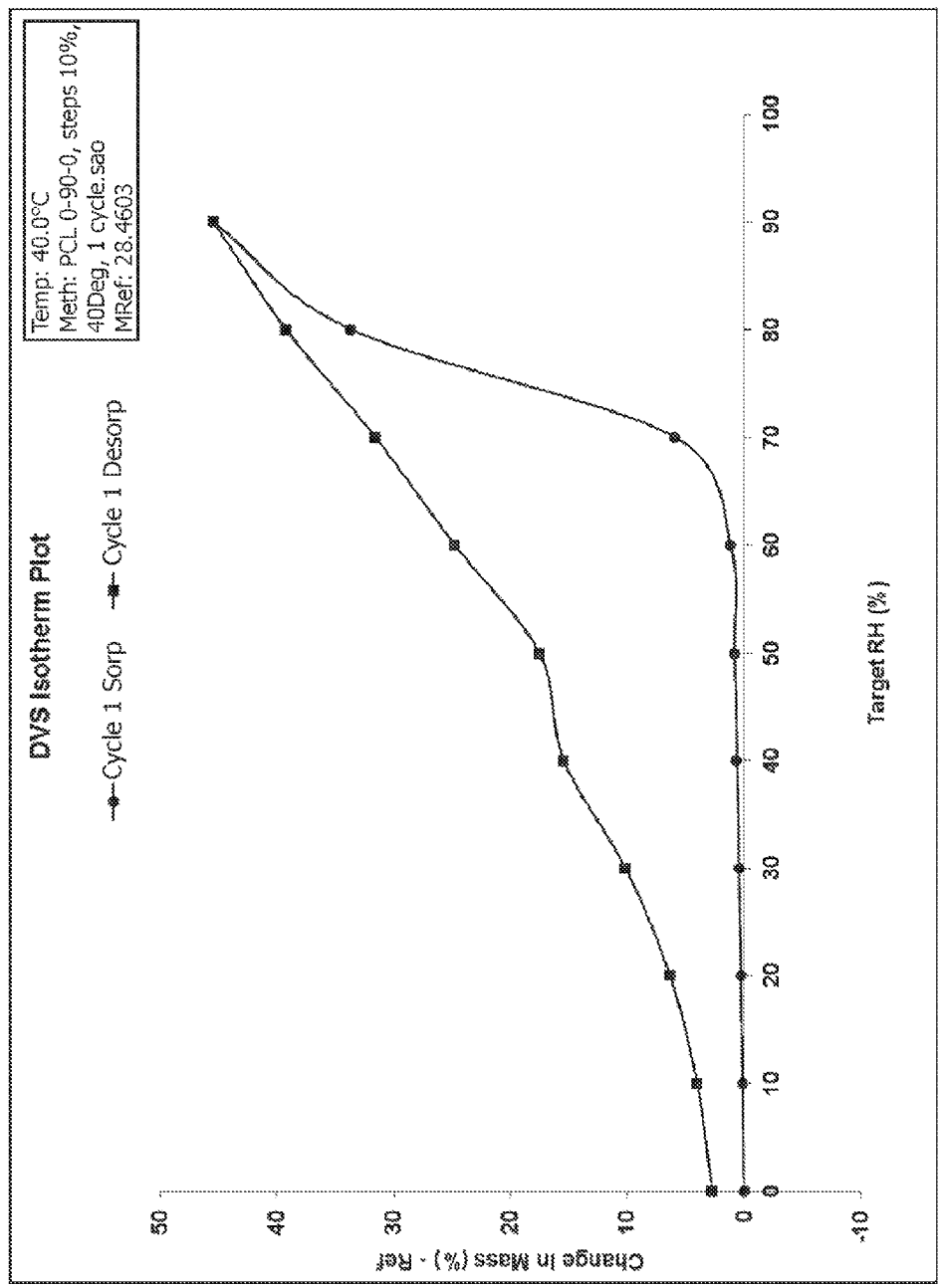
FIG. 12: isotherm at 40° C. anhydrous crystalline form FII of NaHDC.

The polymorphic form FII of NaHDC is characterised by an X-ray powder diffractogram (XPRD) profile as given as an example in FIG. 1, and/or by a differential scanning calorimetry (DSC) profile as given as an example in FIG. 3, and/or by a thermogravimetric profile (TGA) as given as an example in FIG. 6 and/or by an FT-IR/ATR spectrum as shown in FIG. 7, by an FT-RAMAN spectrum as given as an example in FIG. 9, by a dynamic vapour sorption (DVS) analysis in isotherm at 25° C. as given as an example in FIG. 10 and by a dynamic vapour sorption (DVS) analysis in isotherm at 40° C. as given as an example in FIG. 12.

The polymorphic form FII of NaHDC is characterised by the XPRD profile shown in FIG. 1, the characteristic peaks of which are found in the following 2 theta positions in FIG. 2: 6.94; 9.84; 13.92; 20.13; 23.30; degrees, with a margin of error on the value indicated for each peak of ±0.20 degrees 2 theta.

FIG. 2 shows the values of the aforementioned XPRD peaks of the polymorphic form FII, together with the corresponding relative intensity.

Figure 4:
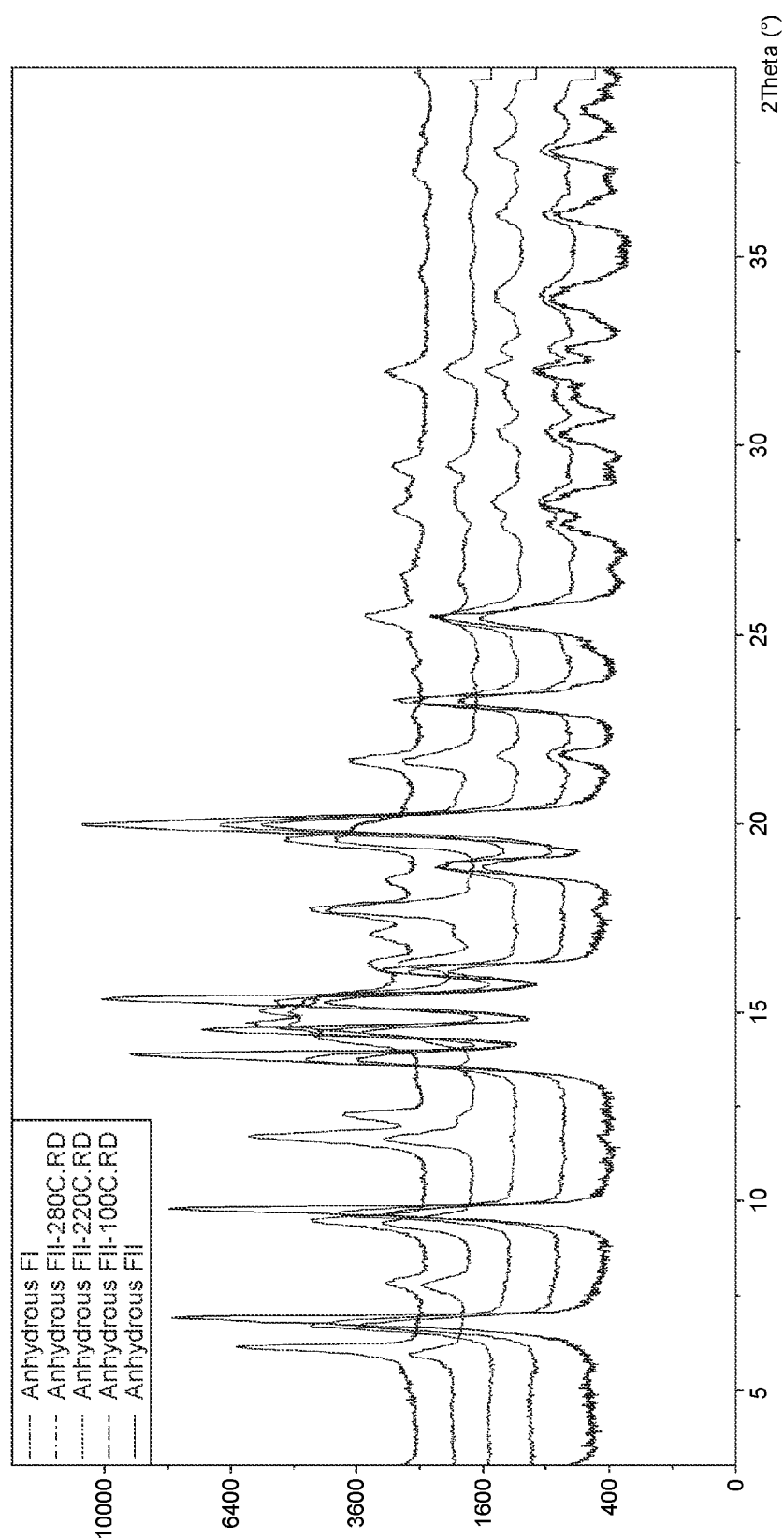
FIG. 4: comparison between XRPD anhydrous form FII at 25° C., XRPD anhydrous form FII at 100° C., XRPD anhydrous form FII at 220° C., XRPD anhydrous form FII at 280° C. towards the anhydrous form I (FI) at 25° C. of NaHDC.

The polymorphic form FII of NaHDC is characterised by the DSC profile shown in FIG. 3. In such a graph it is possible to see an endothermic peak at 260° C., with Peak onset at 263.5° C., Peak at 268.9° C. and enthalpy equal to 14.11 Joule/g, due to the solid-solid phase transition of the polymorphic form FII of NaHDC into the polymorphic form FI, as has been confirmed by X-ray Powder Diffraction (XPRD) analysis at variable temperature (see FIG. 4,5). Therefore, the polymorphic form FII does not melt and is stable up to 260° C. and at 280° C. converts into the crystalline form FI that will be described hereafter. The second peak that can be observed in FIG. 3 is the endothermic peak due to the melting of the polymorphic form FI of NaHDC at 310° C. with Peak onset at 311.6° C., Peak at 314.2° C. and enthalpy of fusion equal to 67.4 Joule/g.

The polymorphic form FII of NaHDC is characterised by the TGA profile shown in FIG. 6. The TGA profile shows an initial weight loss at about 40° C. of roughly 0.4% that can be attributed to imbibition water, after which no more losses of mass are observed up to 350° C., experimentally confirming the fact that such a form is in its "anhydrous" form.

The polymorphic form FII of NaHDC is characterised by the FT-IR/ATR spectrum shown in FIG. 7, the characteristic peaks of which are found at the following frequencies in FIG. 8: 3254.5; 2958.9; 2917.3; 2874.6; 2851.0; 1560.7; 1474.9; 1454.7; 1443.6; 1394.2; 1347.4; 1292.9; 1261.0; 1245.7; 1218.6; 1161.2; 1002.3 $cm^{-1}$, with a margin of error on the value indicated for each peak of ±1 $cm^{-1}$, The polymorphic form FII of NaHDC is characterised by the FT-RAMAN spectrum shown in FIG. 9.

The polymorphic form FII of NaHDC is characterised by the DVS graph in isotherm at 25° C.±0.1 as given as an example in FIG. 10 and by the corresponding values expressed in % as shown in FIG. 11.

The polymorphic form FII of NaHDC is characterised by the DVS graph in isotherm at 40° C.±0.1 as given as an example in FIG. 12 and by the corresponding values expressed in % as shown in FIG. 13.

The polymorphic form FII, unlike all the other described forms of NaHDC, has a very high stability in the humidity sorption cycle in isotherm at 25° C. and at 40° C. (see FIGS. 10,11,12,13). As already indicated above, the polymorphic form FII has non-hygroscopic behaviour unlike all the other polymorphic forms (see FIGS. 27,28,58) found and therefore it is very stable and easily stored. This behaviour is absolutely unusual for the other sodium salts of bile acids, which have the common problem of high hygroscopicity and therefore consequent difficulty of conservation due to their instability.

The polymorphic form FII has a very high and surprising stability with regard to humidity in isotherm at 25° C. and at 40° C.

Indeed, in sorption at 25° C. the sample is stable up to 70% RH (at 70% RH it shows a weight increase of less than 2%). After 70% RH it absorbs humidity and at 90% RH there is a weight change of about 35%. In desorption at 25° C. the sample is stable up to 50% RH preserving the change in weight of about 34% (which corresponds to about 8 water molecules). At roughly 40% RH an inflection can be seen, and at this point the sample seems to still contain about 18% water (which corresponds to about 4 water molecules). At 0% RH the weight change is zero. In sorption at 40° C. the sample is stable up to 60% RH (at 70% RH it shows a weight increase of less than 2%). At 90% RH there is a weight change of about 45% (probably the sample becomes deliquescent). In desorption at 40° C. at 50-40% RH the curve shows a plateau probably at the solidification of the sample. At 0% RH the weight change is about 6%.

Figure 27:
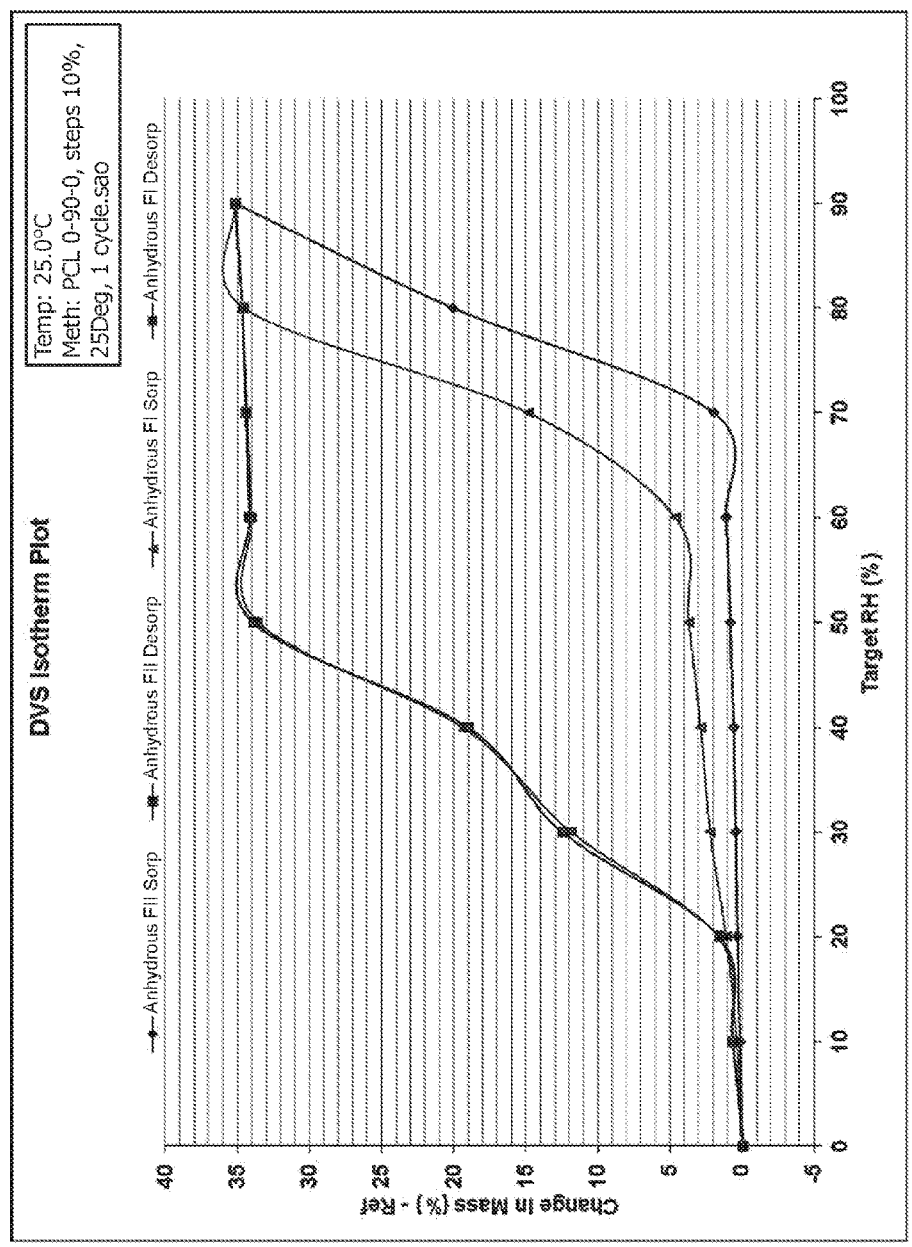
FIG. 27: isotherm comparison at 25° C. anhydrous form FI and anhydrous form FII of NaHDC.

From DVS analysis at 25° C., the polymorphic form FI is less stable than the polymorphic form FII: the polymorphic form FII is stable in sorption at 25° C. up to about 70% RH, whereas the polymorphic form FI already at 20% RH shows a change in weight of roughly 2% (see FIG. 27). From DVS analysis at 40° C., the polymorphic form FI is less stable than the polymorphic form FII: the polymorphic form FII is stable in sorption at 40° C. up to about 70% RH, whereas the polymorphic form FI already at 30% RH shows a change in weight of about 2% (see FIG. 28). Moreover, NaHDC mixture (mixture of different polymorphic forms that is obtained before final reprecipitation for example in anhydrous acetone), from DVS analysis at 25° C. is less stable than the polymorphic form FII (see FIG. 58). The polymorphic form FII is stable in sorption up to about 70% RH, whereas NaHDC mixture already at 20% RH shows a change in weight of about 3%.

Sodium hyodeoxycholate in the polymorphic form FI is another anhydrous crystalline form. The amount of water in the crystal is less than 1%, preferably less than 0.6% and even more preferably it is less than 0.4%, where said percentages are in relation to the total weight of the crystal.

Figure 14:
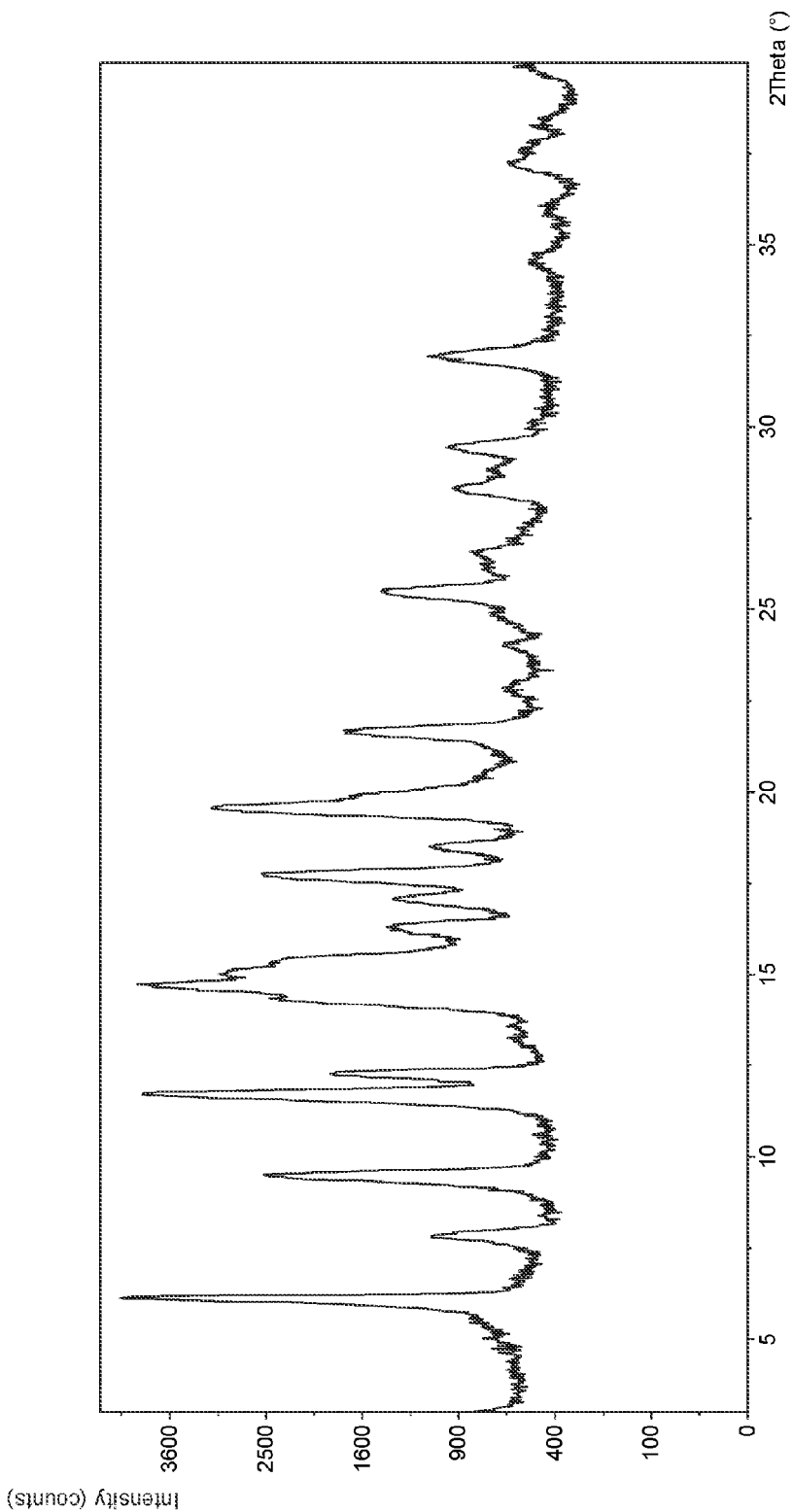
FIG. 14: shows the X-ray powder diffractogram (XPRD) of the anhydrous crystalline form FI of NaHDC.
Figure 16:
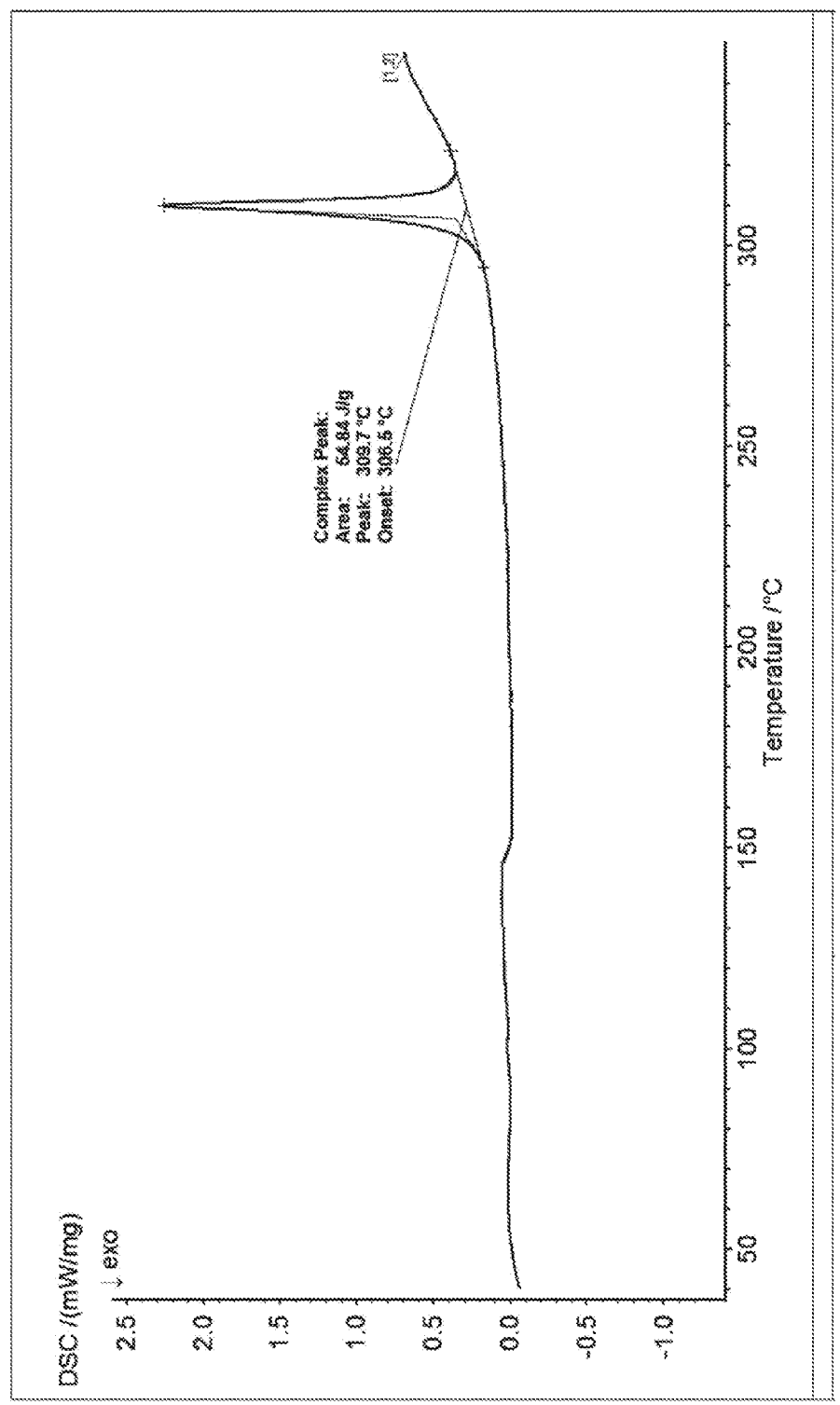
FIG. 16: shows the differential scanning calorimetry (DSC) profile of the anhydrous crystalline form FI of NaHDC.
Figure 17:
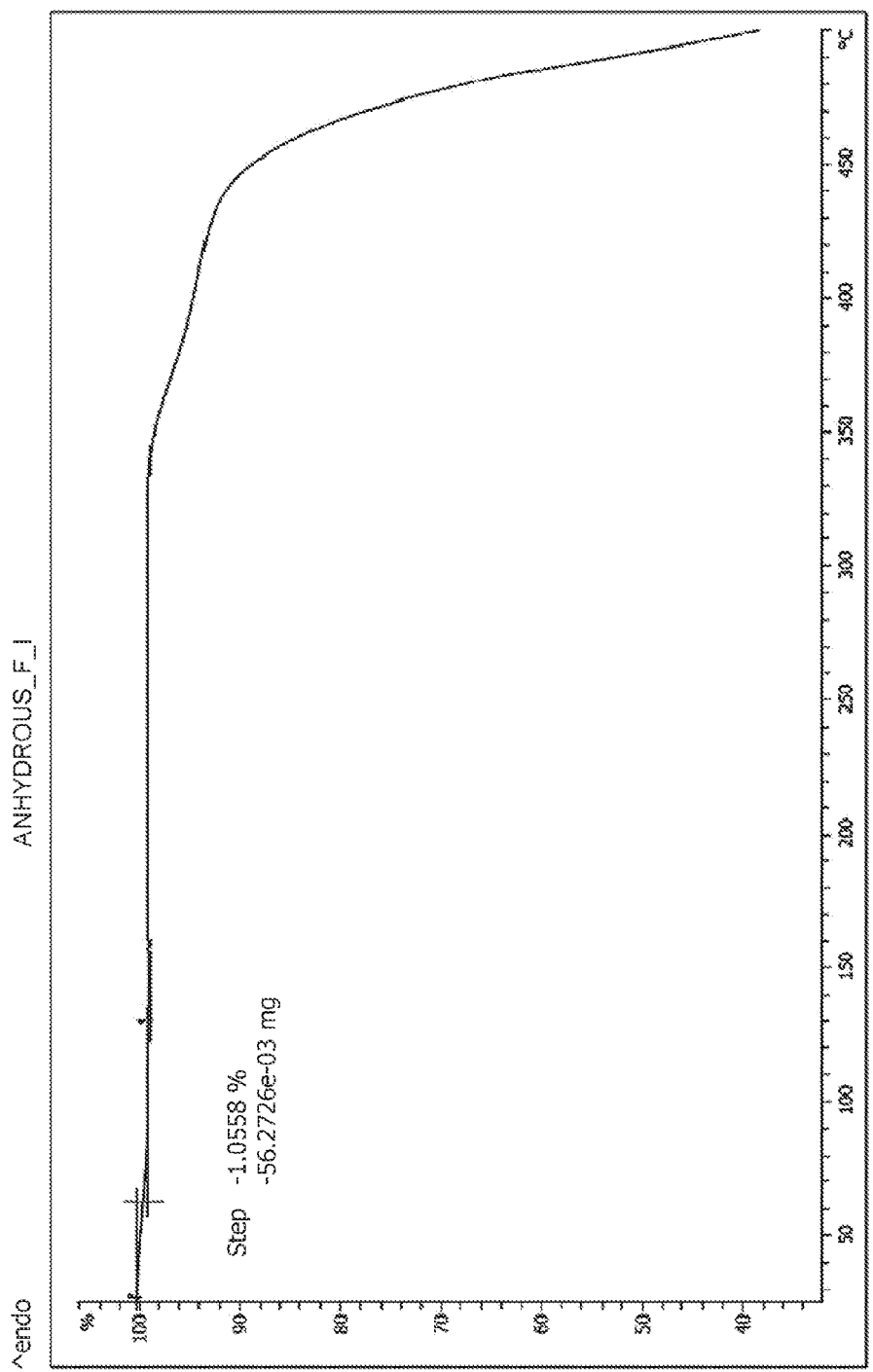
FIG. 17: shows the thermogravimetric profile (TGA) of the anhydrous crystalline form FI of NaHDC.
Figure 20:
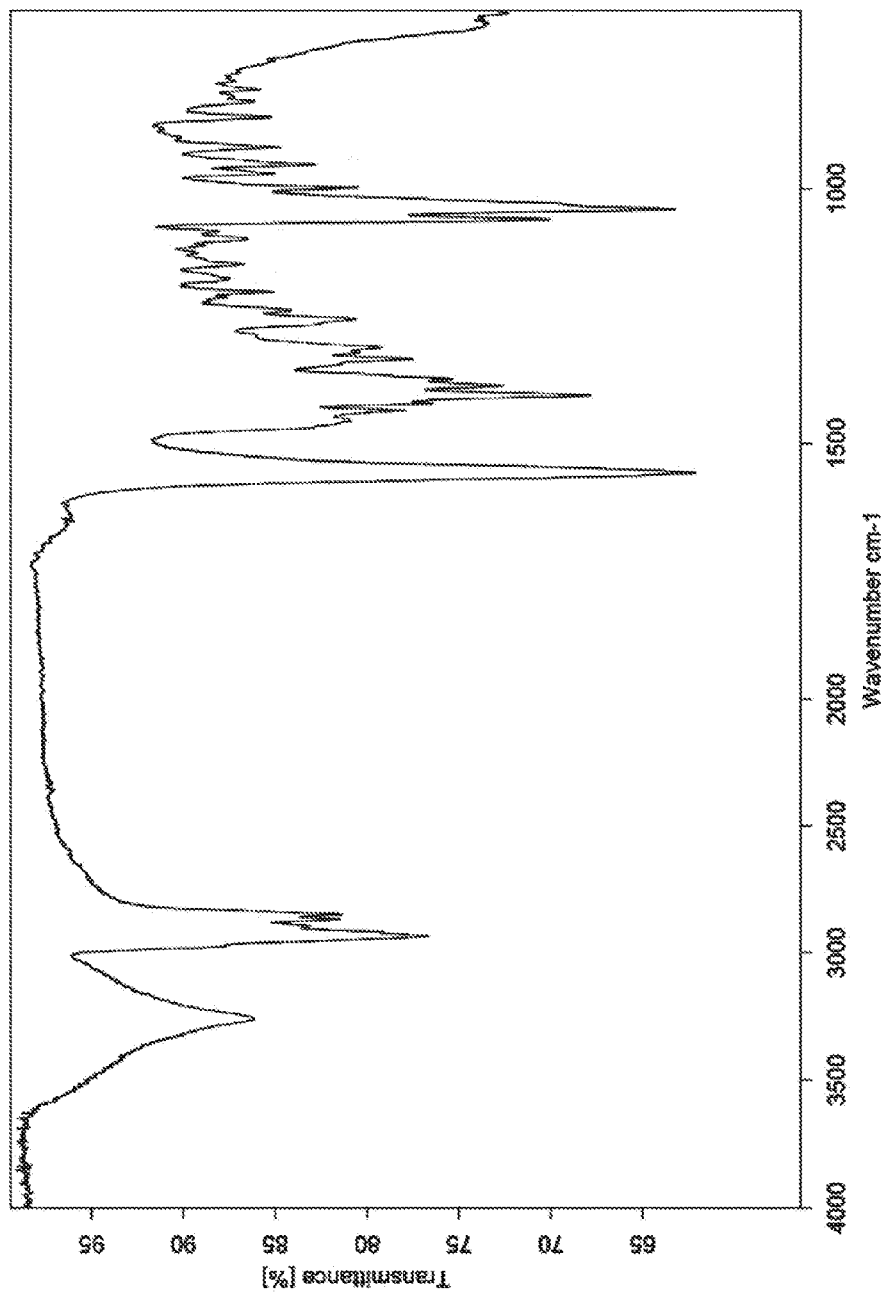
FIG. 20: shows the FT-IR/ATR spectrum of the anhydrous crystalline form FI of NaHDC.
Figure 22:
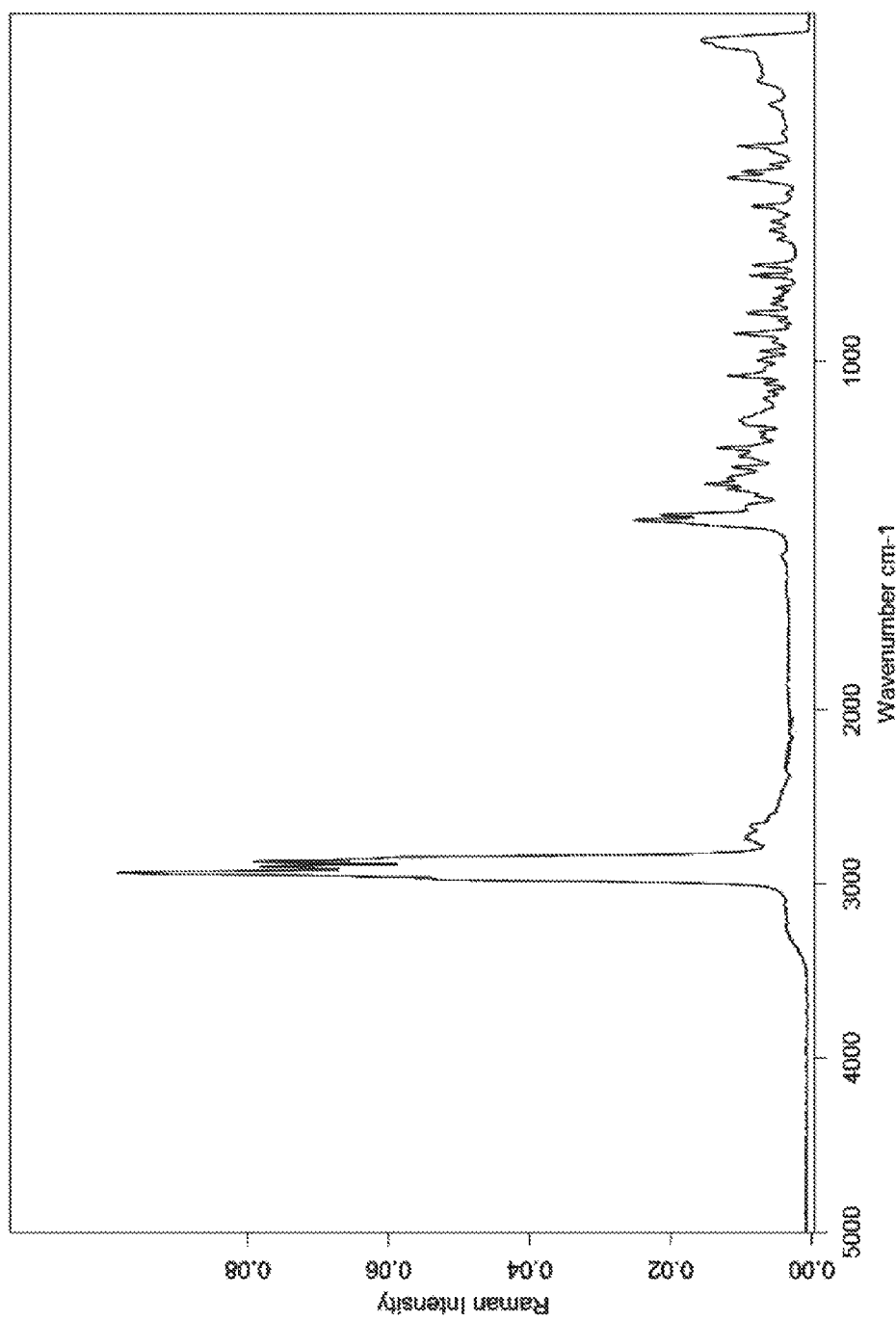
FIG. 22: shows the FT-RAMAN spectrum of the anhydrous crystalline form FI of NaHDC.
Figure 23:
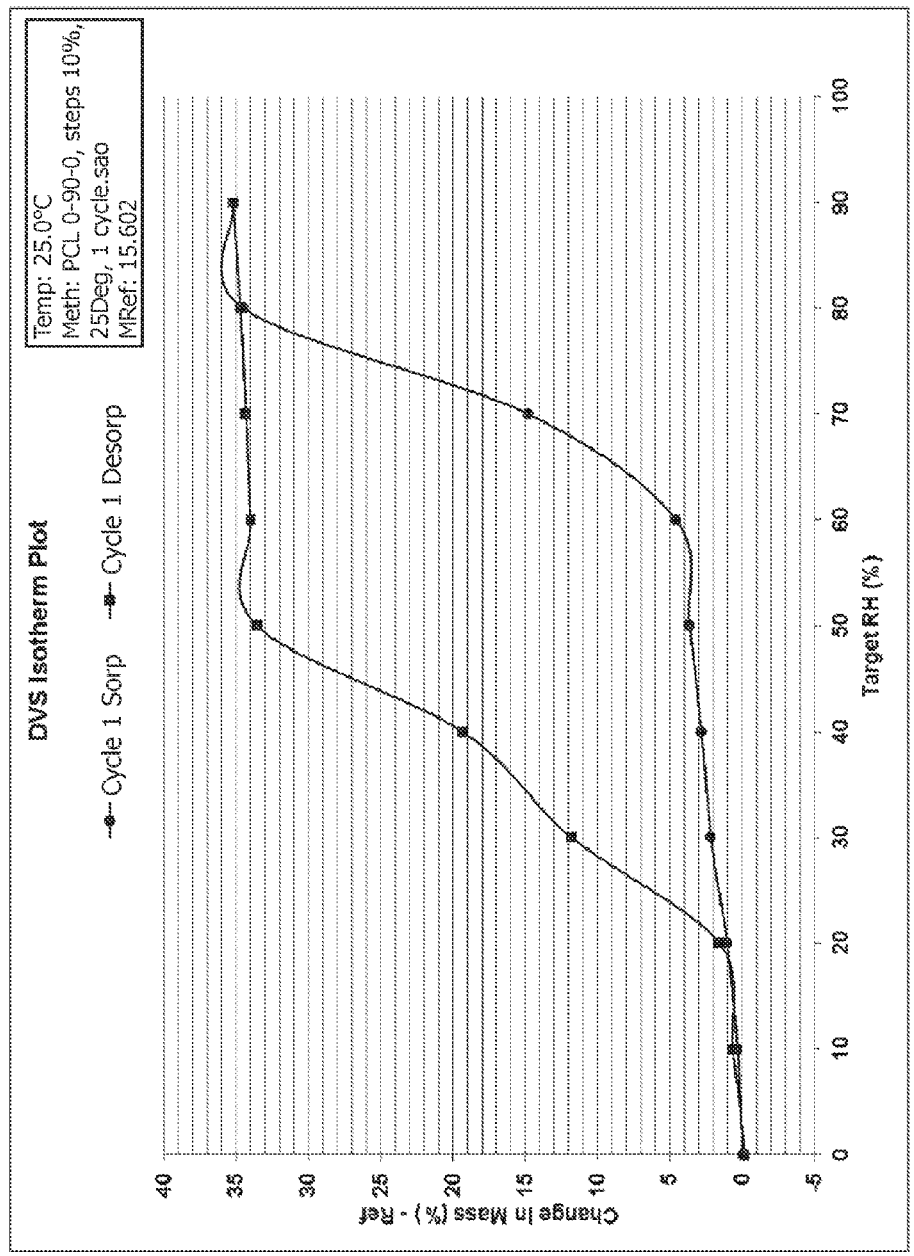
FIG. 23: isotherm at 25° C. anhydrous crystalline form FI of NaHDC.
Figure 25:
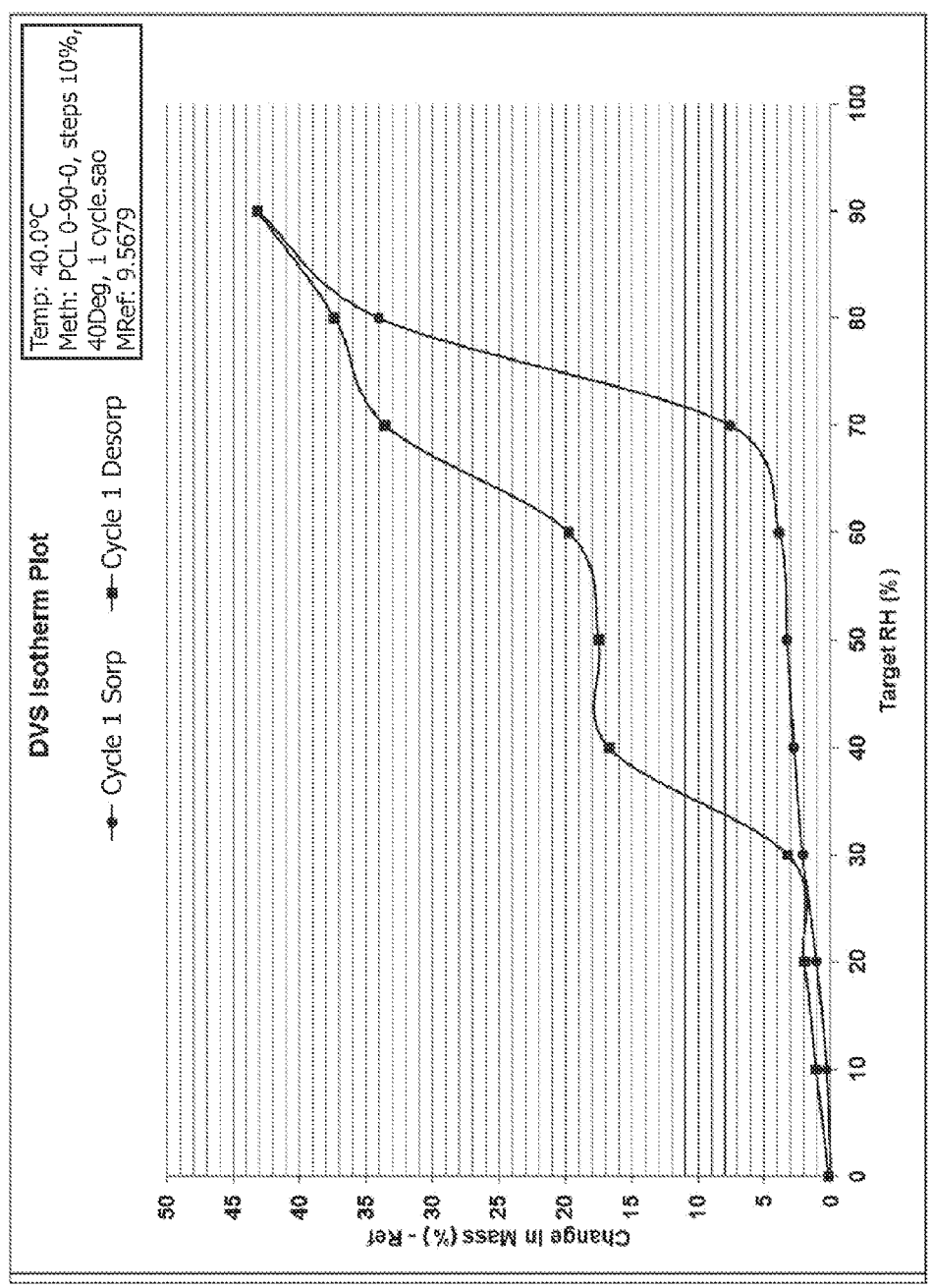
FIG. 25: isotherm at 40° C. anhydrous crystalline form FI of NaHDC.

The polymorphous crystalline form FI of NaHDC is characterised by an X-ray powder diffractogram (XPRD) profile as given as an example in FIG. 14, and/or by a differential scanning calorimetry (DSC) profile as given as an example in FIG. 16, and/or by a thermogravimetric profile (TGA) as given as an example in FIG. 17 and/or by an FT-IR/ATR spectrum as shown in FIG. 20, by an FT-RAMAN spectrum as given as an example in FIG. 22, by a dynamic vapour sorption (DVS) analysis in isotherm at 25° C. as given as an example in FIG. 23 and by a dynamic vapour sorption (DVS) analysis in isotherm at 40° C. as given as an example in FIG. 25.

Figure 28:
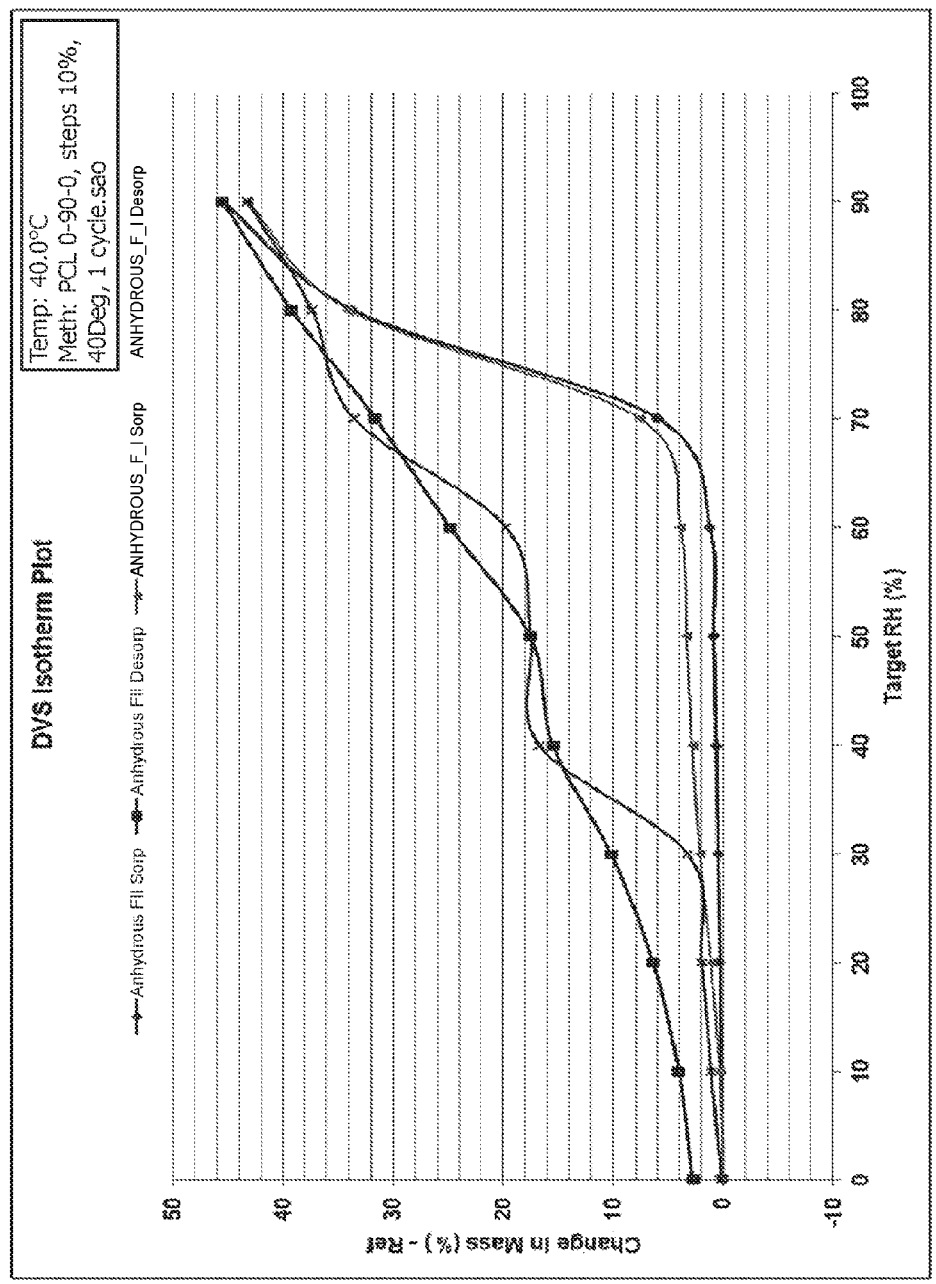
FIG. 28: isotherm comparison at 40° C. anhydrous form FI and anhydrous form FII of NaHDC.

Moreover, the comparison of the dynamic vapour sorption (DVS) analysis in isotherm at 25° C. and at 40° C. of the polymorphic form FI and of the polymorphic form FII as given as an example in FIGS. 27 and 28 is described.

The polymorphic form FI of NaHDC is characterised by the XPRD profile shown in FIG. 14, the characteristic peaks of which are found at the following 2 theta positions in FIG. 15: 6.17; 7.82; 9.50; 11.77; 12.35; 17.03; 17.78; 19.63; 21.71; 25.53; degrees, with a margin of error on the value indicated for each peak of ±0.20 degrees 2 theta.

FIG. 15 shows the values of the aforementioned XPRD peaks of the polymorphic form FI, together with the corresponding relative intensity.

The polymorphic form FI of NaHDC is characterised by the DSC profile shown in FIG. 16. In such a graph an endothermic peak can be observed at 310° C., with Peak onset at 306.5° C., Peak at 309.7° C. and enthalpy of fusion equal to 54.84 Joule/g, due to the melting of the anhydrous form FI. Moreover, the diffraction analysis (XPRD) was carried out at variable temperature (see FIGS. 18,19) and proved stable up to 280° C.

Figure 18:
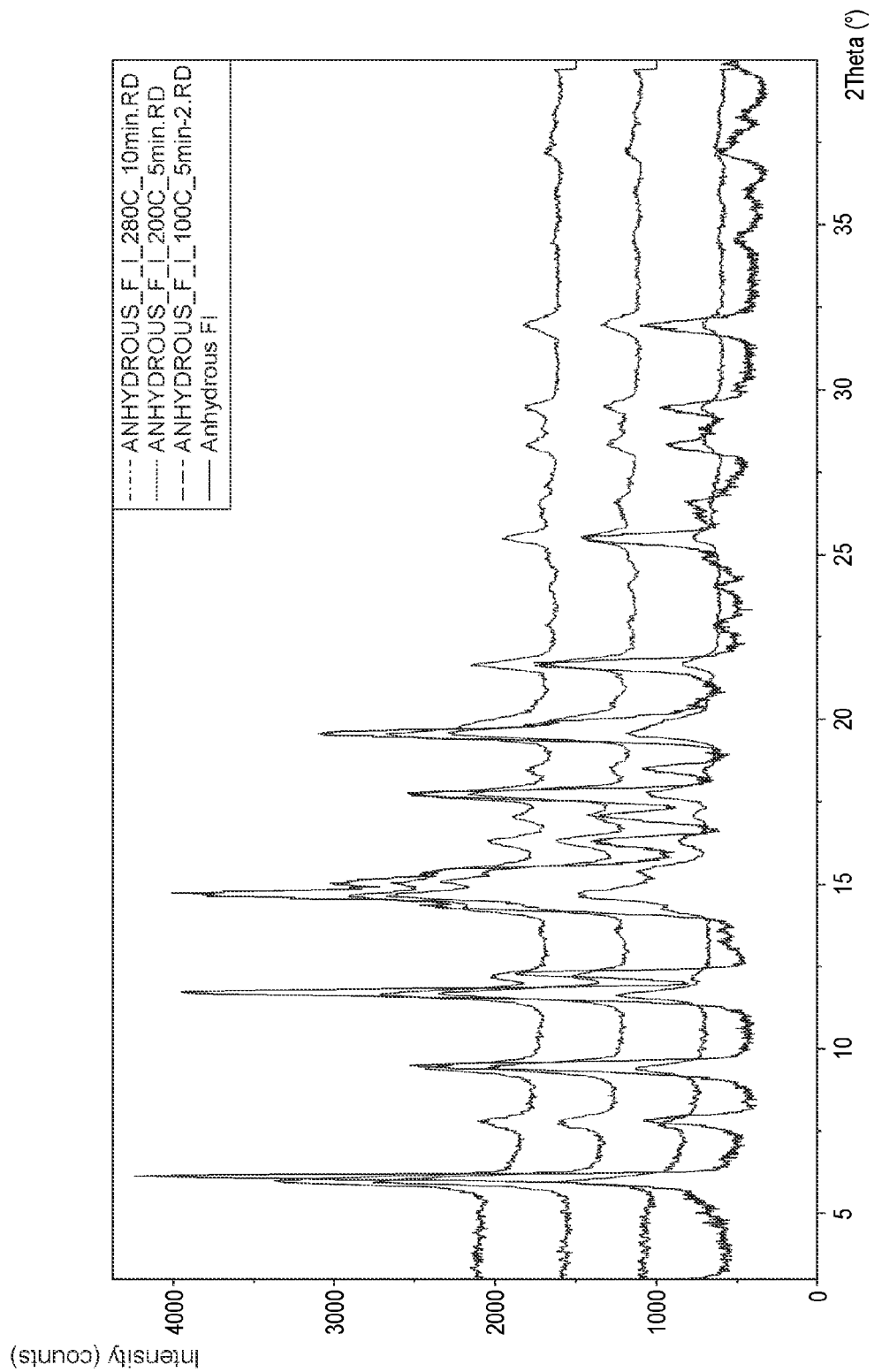
FIG. 18: comparison between XRPD anhydrous crystalline form FI at 25° C., XRPD anhydrous crystalline form FI at 100° C., XRPD anhydrous crystalline form FI at 200° C. and XRPD anhydrous crystalline form FI at 280° C. of NaHDC.

The polymorphic form FI of NaHDC is characterised by the TGA profile shown in FIG. 17. The TGA profile shows an initial weight loss at about 50° C., of about 1% attributable to imbibition water, and no more losses of mass are observed up to 350° C., experimentally confirming the fact that such a form is in its "anhydrous" form. This has been confirmed by diffraction analysis (XPRD) at variable temperature. The polymorphic form FI is stable up to 280° C. as shown in FIG. 18,19, as already shown above and then melts as shown in FIG. 16.

The polymorphic form FI of NaHDC is characterised by the FT-IR/ATR spectrum shown in FIG. 20, the characteristic peaks of which are found at the following frequencies in FIG. 21: 3259.0; 2932.5; 2916.1; 2893.2; 2867.4; 2848.1; 1557.5; 1454.8; 1435.3; 1421.5; 1405.8; 1387.1; 1334.2; 1311.5; 1084.6; 1060.3 cm$^{-1}$, with a margin of error on the value indicated for each peak of ±1 cm$^{-1}$.

The polymorphic form FI of NaHDC is characterised by the FT-RAMAN spectrum shown in FIG. 22.

The polymorphic form FI of NaHDC is characterised by the DVS graph in isotherm at 25° C.±0.1 as given as an example in FIG. 23 and by the corresponding values expressed in % as shown in FIG. 24.

In sorption, at 30% RH, the sample shows a weight change of about 2% circa and at 70% RH of 15%. At 90% RH there is a weight change of about 35%.

In desorption the sample is stable up to 50% RH preserving the weight change of about 34% (which corresponds to about 8 water molecules).

At about 40% RH an inflection can be seen, and in this point the sample seems to still contain about 18% water (which corresponds to about 4 water molecules).

At 0% RH the weight change is zero.

The polymorphic form FI of NaHDC is characterised by the DVS graph in isotherm at 40° C.±0.1 as given as an example in FIG. 25 and by the corresponding values expressed in % as shown in FIG. 26.

In sorption, at 30% RH, the sample shows a weight change of about 2% and at 70% RH of 8%. At 90% RH there is a weight change of about 43%. In desorption at 50-40% RH the curve shows a plateau and the sample shows a change in weight of about 17%. At 0% RH the weight change is zero.

Moreover, the comparison has been made in isotherm at 25° C. and at 40° C. of the polymorphic form FI and of the polymorphic form FII of NaHDC as shown in FIGS. 27 and 28.

Further polymorphic forms of NaHDC characterised in the present invention are the further polymorphic form FIII, the hydrated polymorphic forms of NaHDC named as SI and SII that are forms of NaHDC respectively hydrated with four and eight water molecules and the amorphous form.

Sodium hyodeoxycholate in the polymorphic form FIII is another anhydrous crystalline form. The amount of water in the crystal is less than 1%, preferably less than 0.6% and even more preferably it is less than 0.4%, where said percentages are in relation to the total weight of the crystal.

Figure 29:
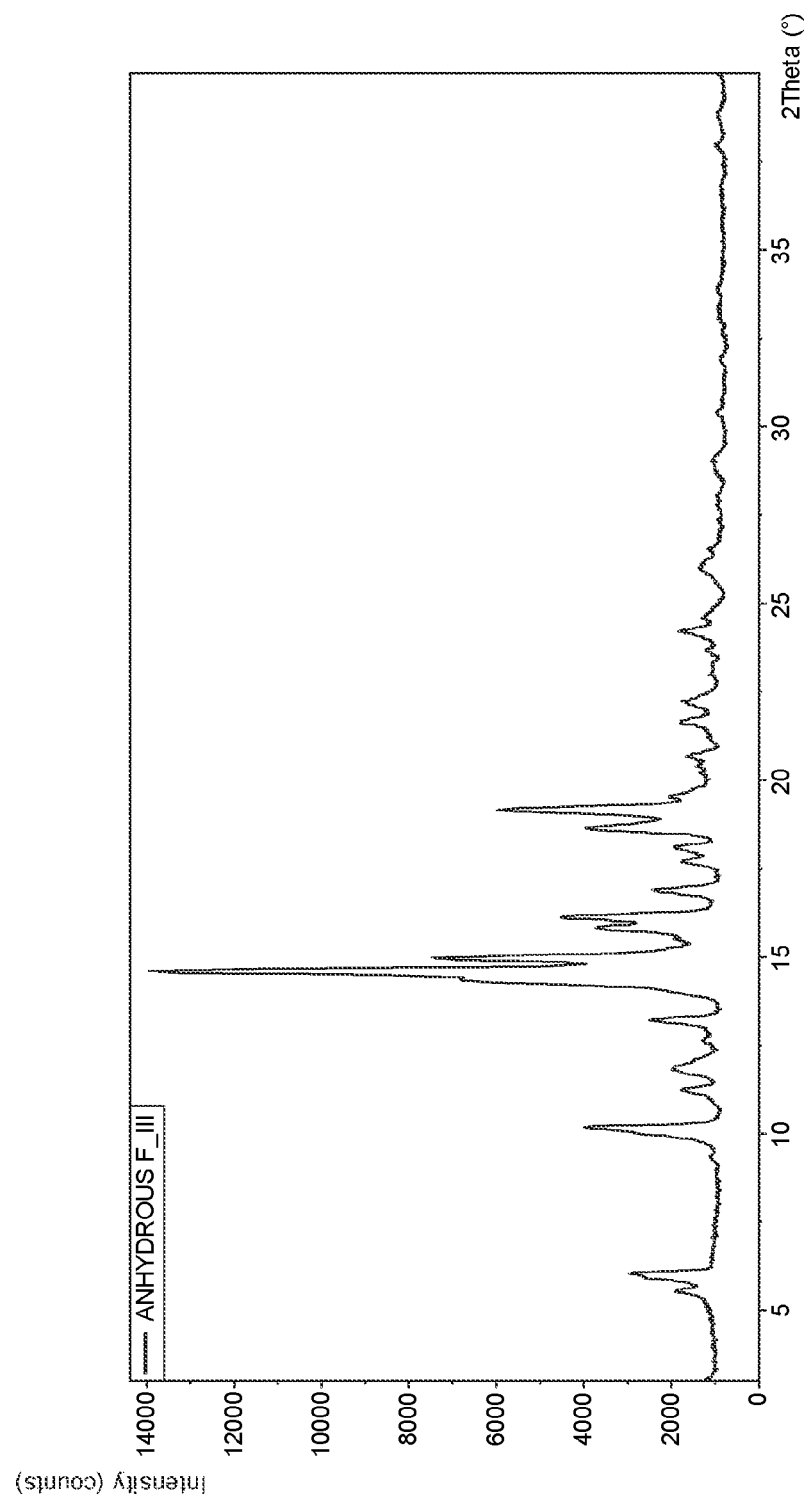
FIG. 29: shows the X-ray powder diffractogram (XPRD) of the anhydrous crystalline form III (FIII) of NaHDC.
Figure 31:
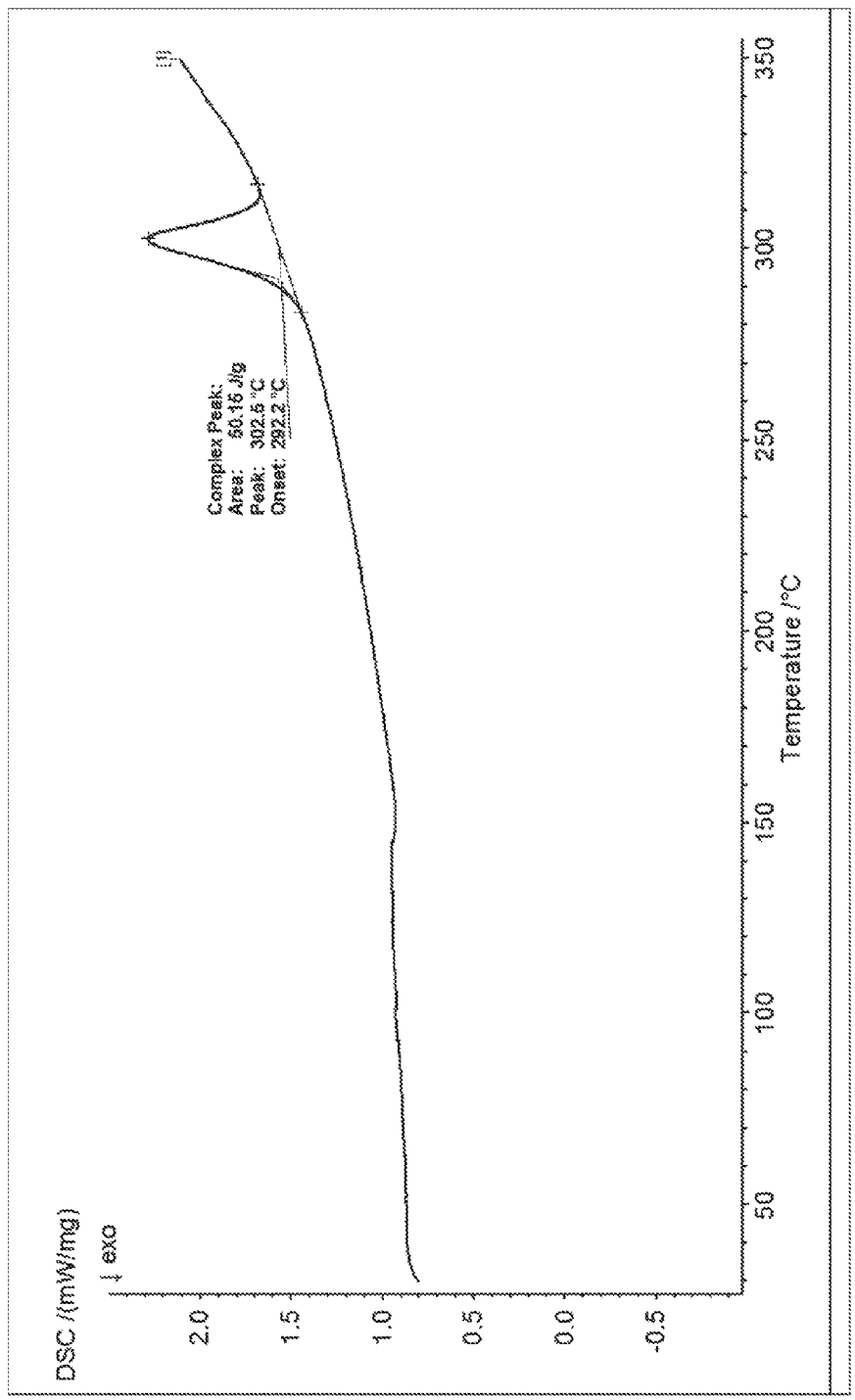
FIG. 31: shows the differential scanning calorimetry (DSC) profile of the anhydrous crystalline form FIII of NaHDC.
Figure 32:
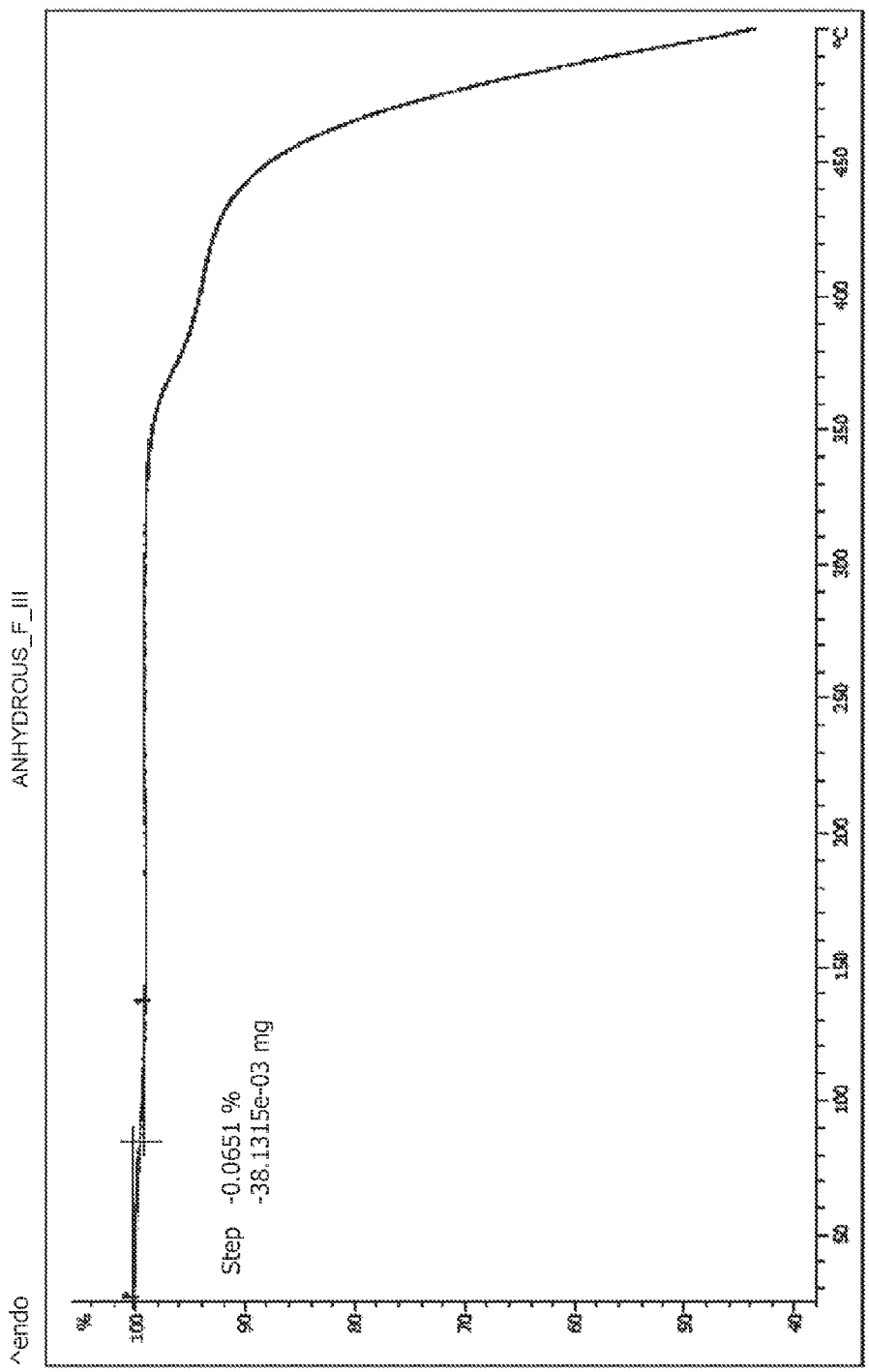
FIG. 32: shows the thermogravimetric profile (TGA) of the anhydrous crystalline form FIII of NaHDC.
Figure 33:
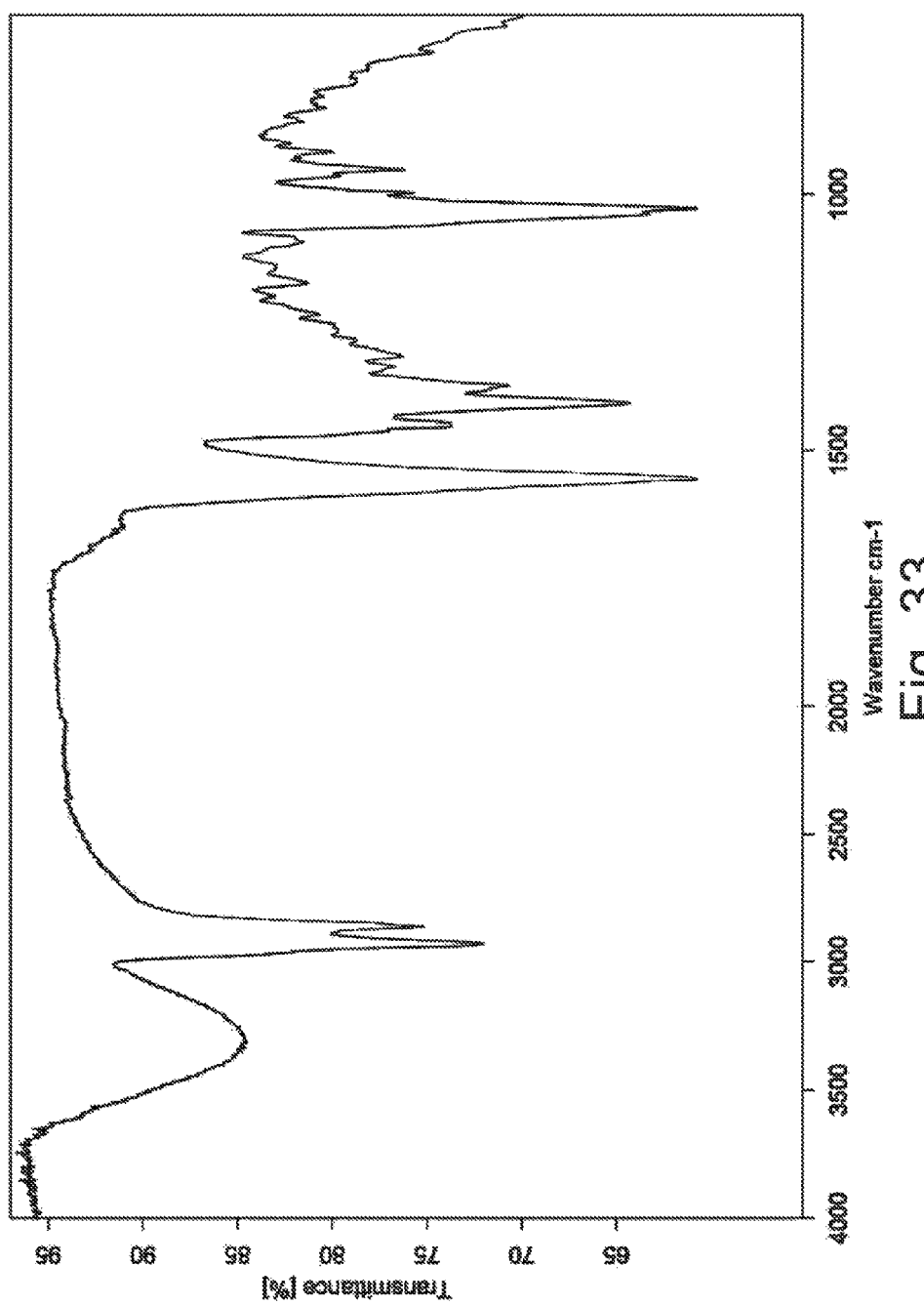
FIG. 33: shows the FT-IR/ATR spectrum of the anhydrous crystalline form FIII of NaHDC.

The polymorphic form FIII of NaHDC is characterised by an X-ray powder diffractogram (XPRD) profile as given as an example in FIG. 29, and/or by a differential scanning calorimetry (DSC) profile as given as an example in FIG. 31, and/or by a thermogravimetric profile (TGA) as given as an example in FIG. 32 and/or by an FT-IR/ATR spectrum as shown in FIG. 33.

The polymorphic form FIII of NaHDC is characterised by the XPRD profile shown in FIG. 29, the characteristic peaks of which are found at the following 2 theta positions in FIG. 30: 5.54; 10.20; 11.24; 12.63; 14.63; 14.96; 15.78; 16.91; 18.13; 18.62; 19.16; 22.22; 24.24 degrees, with a margin of error on the value indicated for each peak of ±0.20 degrees 2 theta.

FIG. 30 shows the values of the aforementioned XPRD peaks of the polymorphic form FIII, together with the corresponding relative intensity.

The polymorphic form FIII of NaHDC is characterised by the DSC profile shown in FIG. 31. In such a graph it is possible to see an endothermic peak at 290° C., with Peak onset at 292.2° C., Peak at 302.5° C. and enthalpy of fusion equal to 50.15 Joule/g, due to the melting of the anhydrous form FIII.

The polymorphic form FIII of NaHDC is characterised by the TGA profile shown in FIG. 32. The TGA profile shows an initial weight loss at about 50° C. of about 1% attributable to imbibition water, after which no more losses of mass are observed up to 350° C., experimentally confirming the fact that such a form is in its "anhydrous" form.

The polymorphic form FIII of NaHDC is characterised by the FT-IR/ATR spectrum shown in FIG. 33, the characteristic peaks of which are found at the following frequencies in FIG. 34: 2929.5; 2863.5; 1556.8; 1408.0; 1373.6; 1038.2; 1027.8; 997.7; 852.1; 917.4 cm$^{-1}$, with a margin of error on the value indicated for each peak of ±1 cm$^{-1}$.

Sodium hyodeoxycholate in the hydrated polymorphic form SI is a hydrated form, hydrated with about four water molecules.

Figure 35:
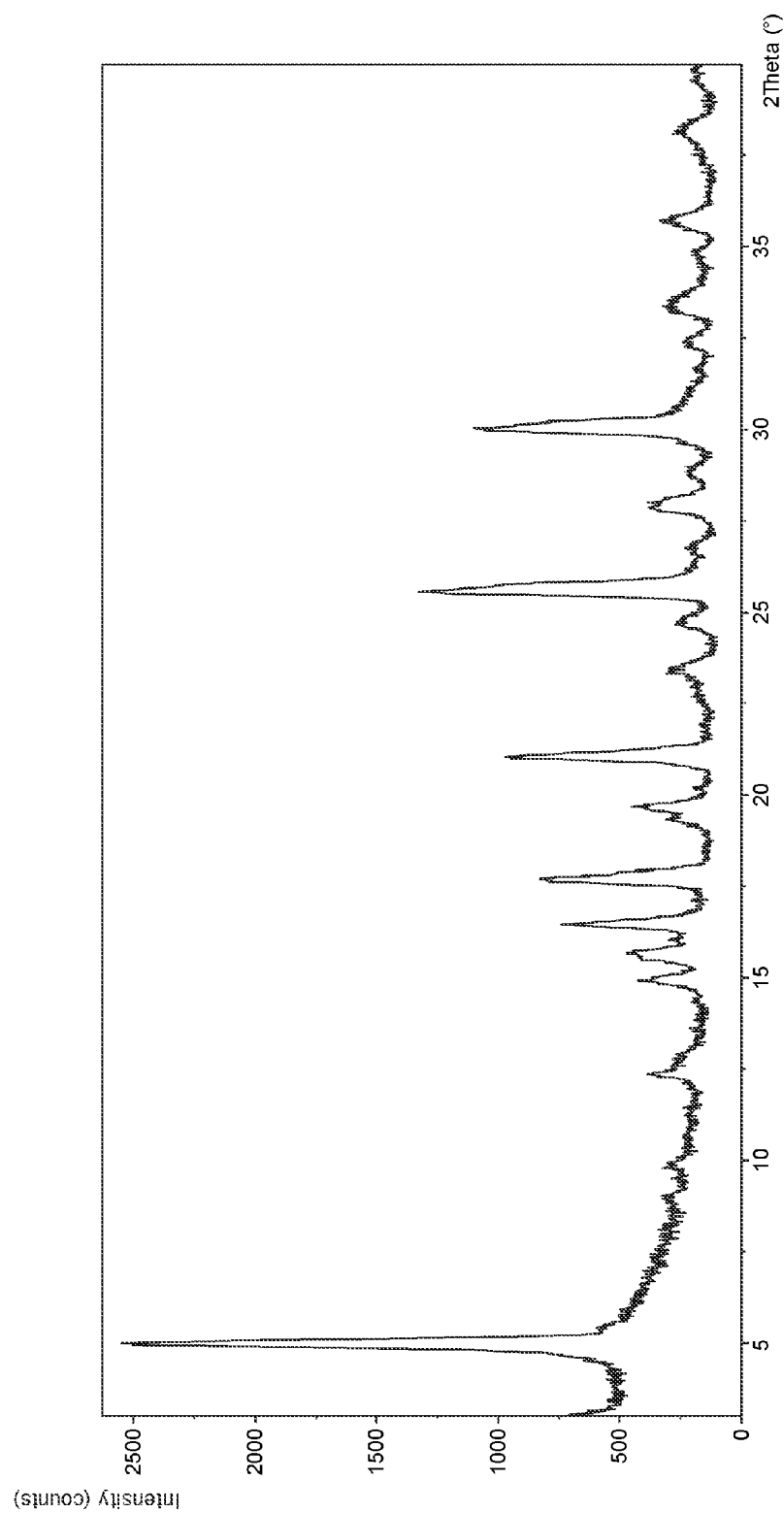
FIG. 35: shows the X-ray powder diffractogram (XPRD) of the hydrated crystalline form SI of NaHDC.
Figure 37:
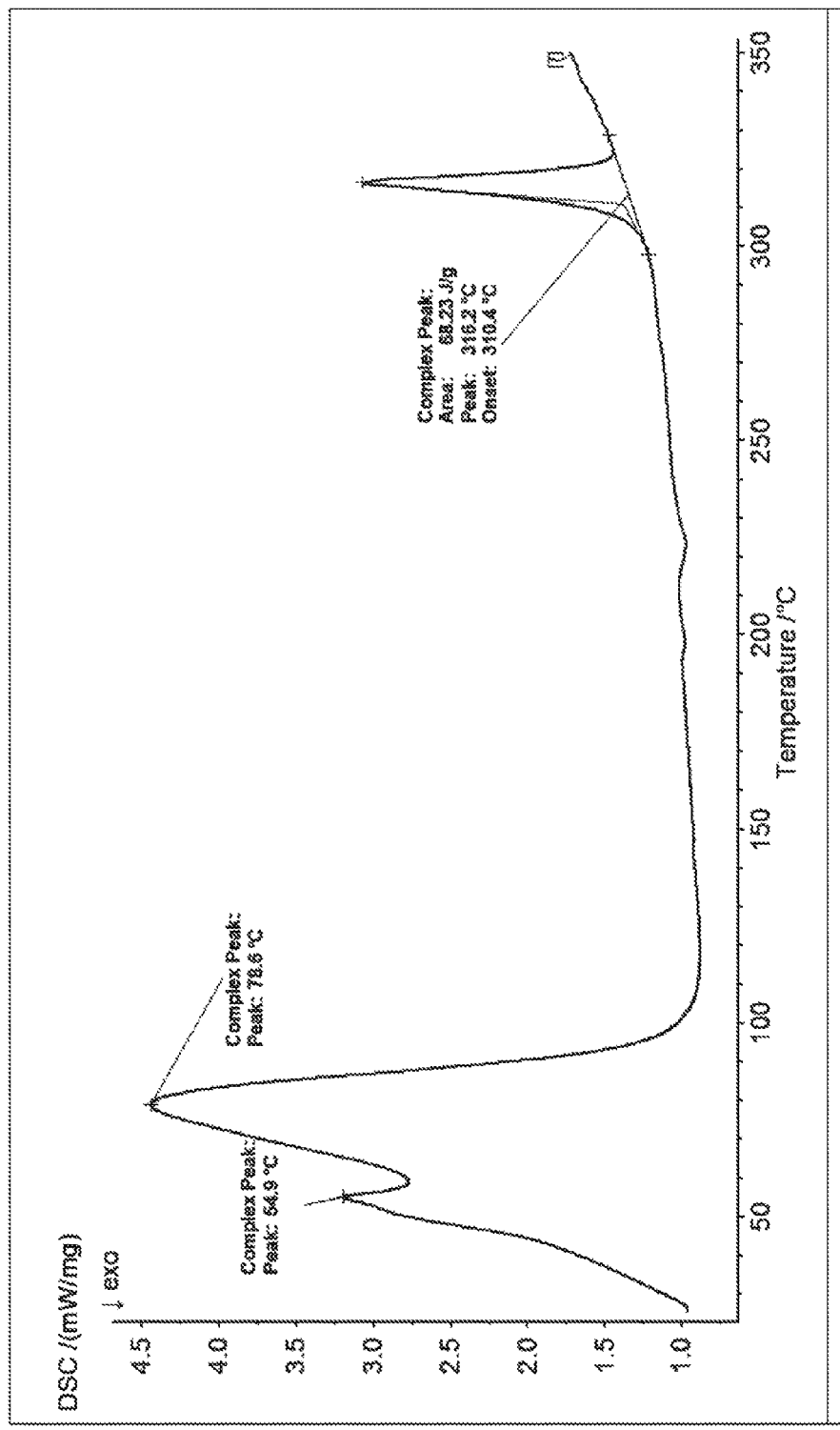
FIG. 37: shows the differential scanning calorimetry (DSC) profile of the hydrated crystalline form SI (SI) of NaHDC.
Figure 38:
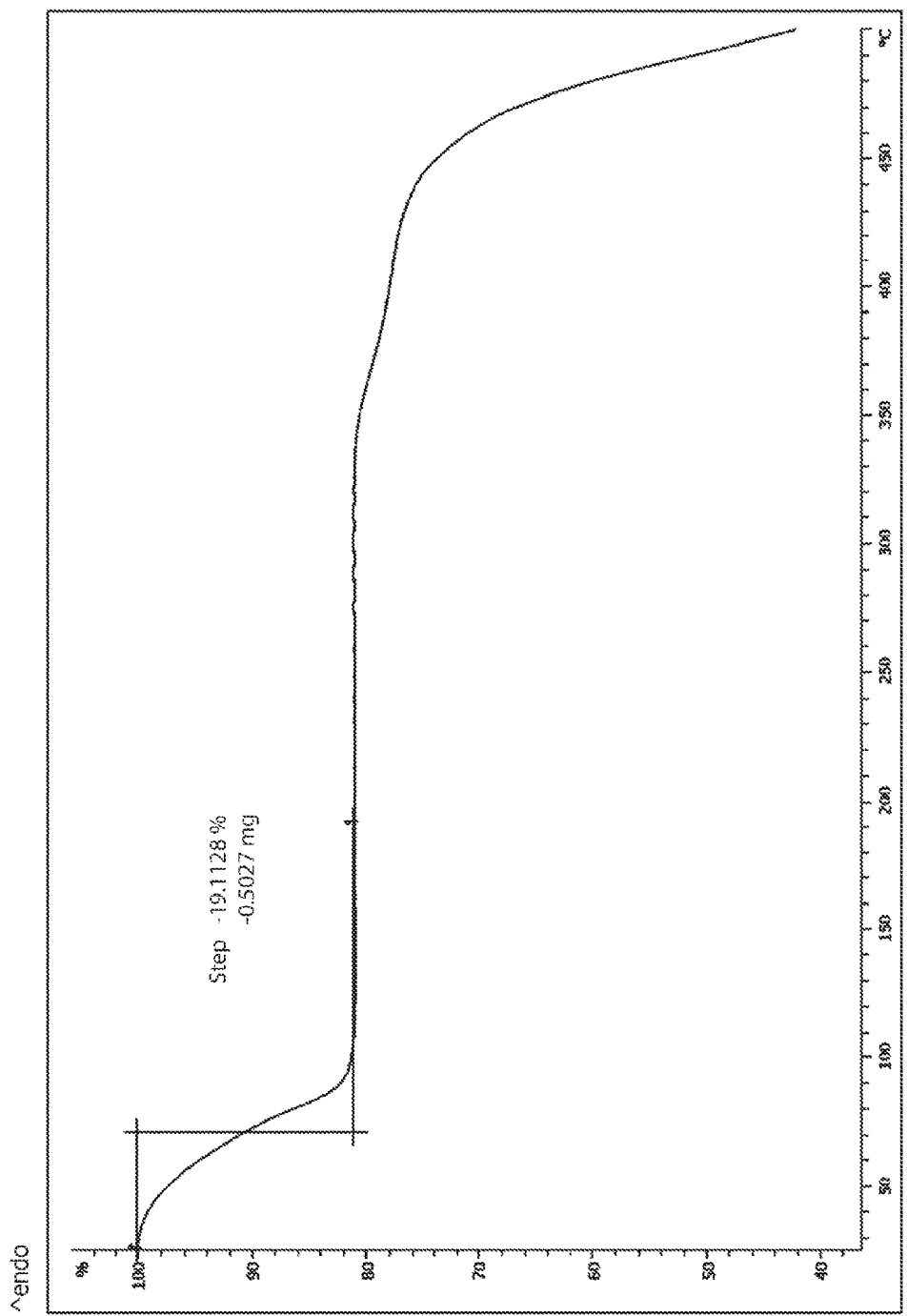
FIG. 38: shows the thermogravimetric profile (TGA) of the hydrated crystalline form SI of NaHDC.
Figure 39:
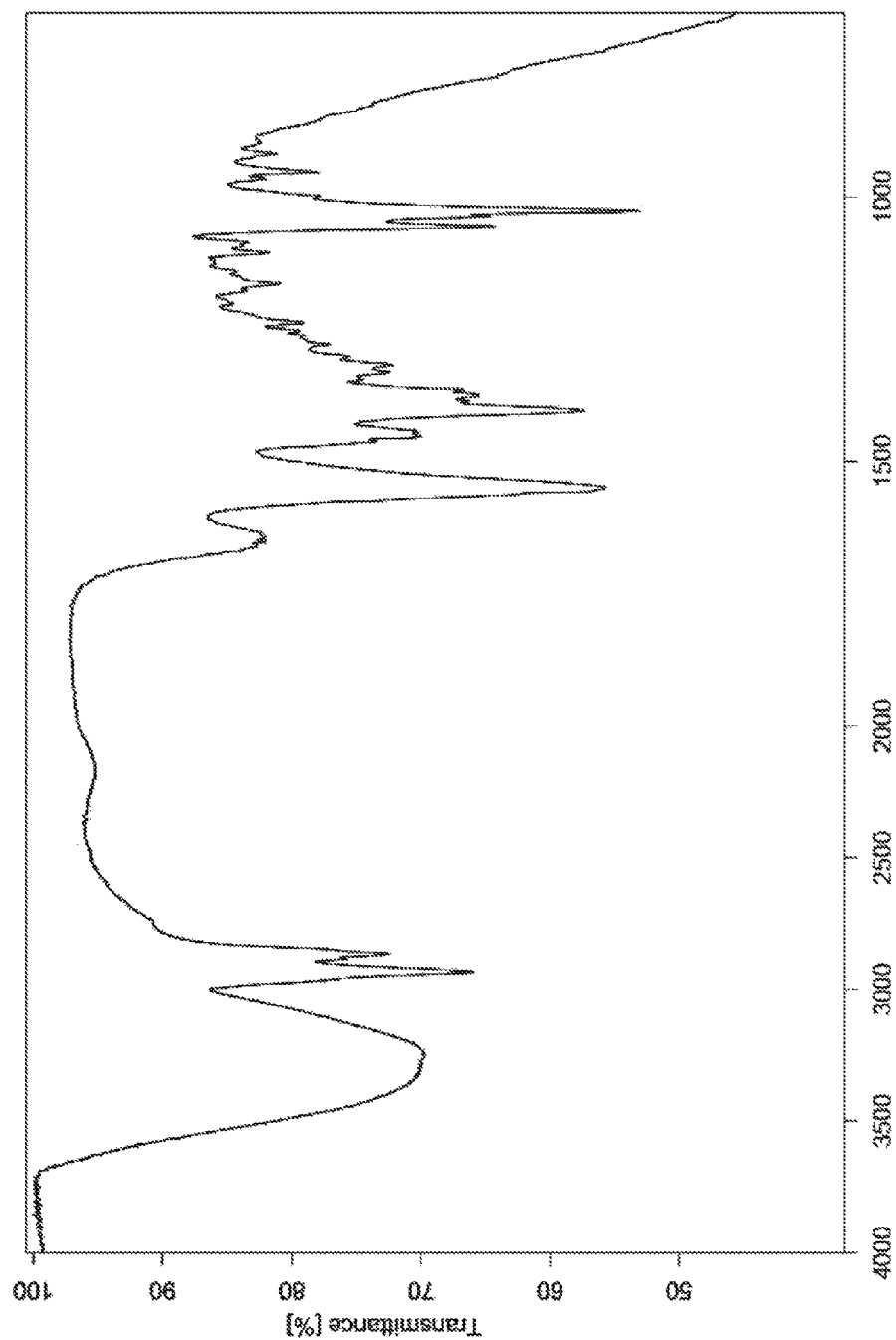
FIG. 39: shows the FT-IR/ATR spectrum of the hydrated crystalline form SI of NaHDC.

The hydrated polymorphic form SI of NaHDC is characterised by an X-ray powder diffractogram (XPRD) profile as given as an example in FIG. 35, and/or by a differential scanning calorimetry (DSC) profile as given as an example in FIG. 37, and/or by a thermogravimetric profile (TGA) as given as an example in FIG. 38 and/or by an FT-IR/ATR spectrum as shown in FIG. 39.

The hydrated polymorphic form SI of NaHDC is characterised by the XPRD profile shown in FIG. 35, the characteristic peaks of which are found at the following 2 theta positions in FIG. 36: 4.92; 12.34; 14.89; 15.70; 16.46; 17.72; 21.01; 25.78; 29.93 degrees, with a margin of error on the value indicated for each peak of ±0.20 degrees 2 theta.

FIG. 36 shows the values of the aforementioned XPRD peaks of the hydrated polymorphic form SI, together with the corresponding relative intensity.

The hydrated polymorphic form SI of NaHDC is characterised by the DSC profile shown in FIG. 37. In such a graph it is possible to see an endothermic event at about 50-70° C. (Complex Peak 54.9° C. and 78.6° C.) associated with the loss of water and an endothermic peak at about 310° C. with Peak onset at 310.4° C., Peak at 316.2° C. and enthalpy of fusion equal to 68.23 Joule/g, due to the melting of the anhydrous form FI in which the hydrated form SI interconverts.

The hydrated polymorphic form SI of NaHDC is characterised by the TGA profile shown in FIG. 38. The TGA profile shows an initial weight loss at about 70° C., of about 19% attributable to the loss of water of such a form.

The hydrated polymorphic form SI of NaHDC is characterised by the FT-IR/ATR spectrum shown in FIG. 39.

Sodium hyodeoxycholate in the hydrated polymorphic form SII is a hydrated form, hydrated with about eight water molecules.

Figure 40:
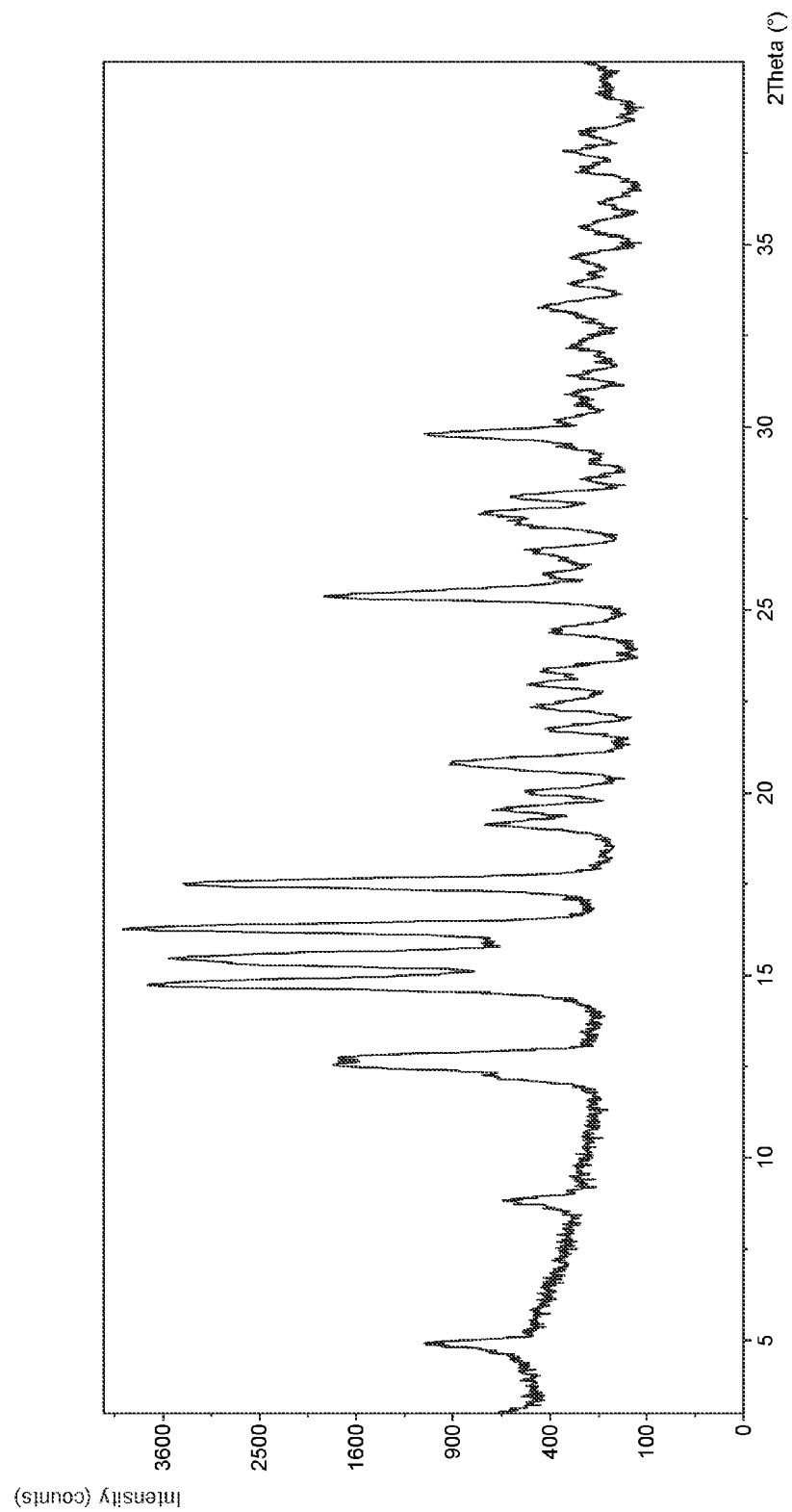
FIG. 40: shows the X-ray powder diffractogram (XPRD) of the hydrated crystalline form SII (SII) of NaHDC.
Figure 42:
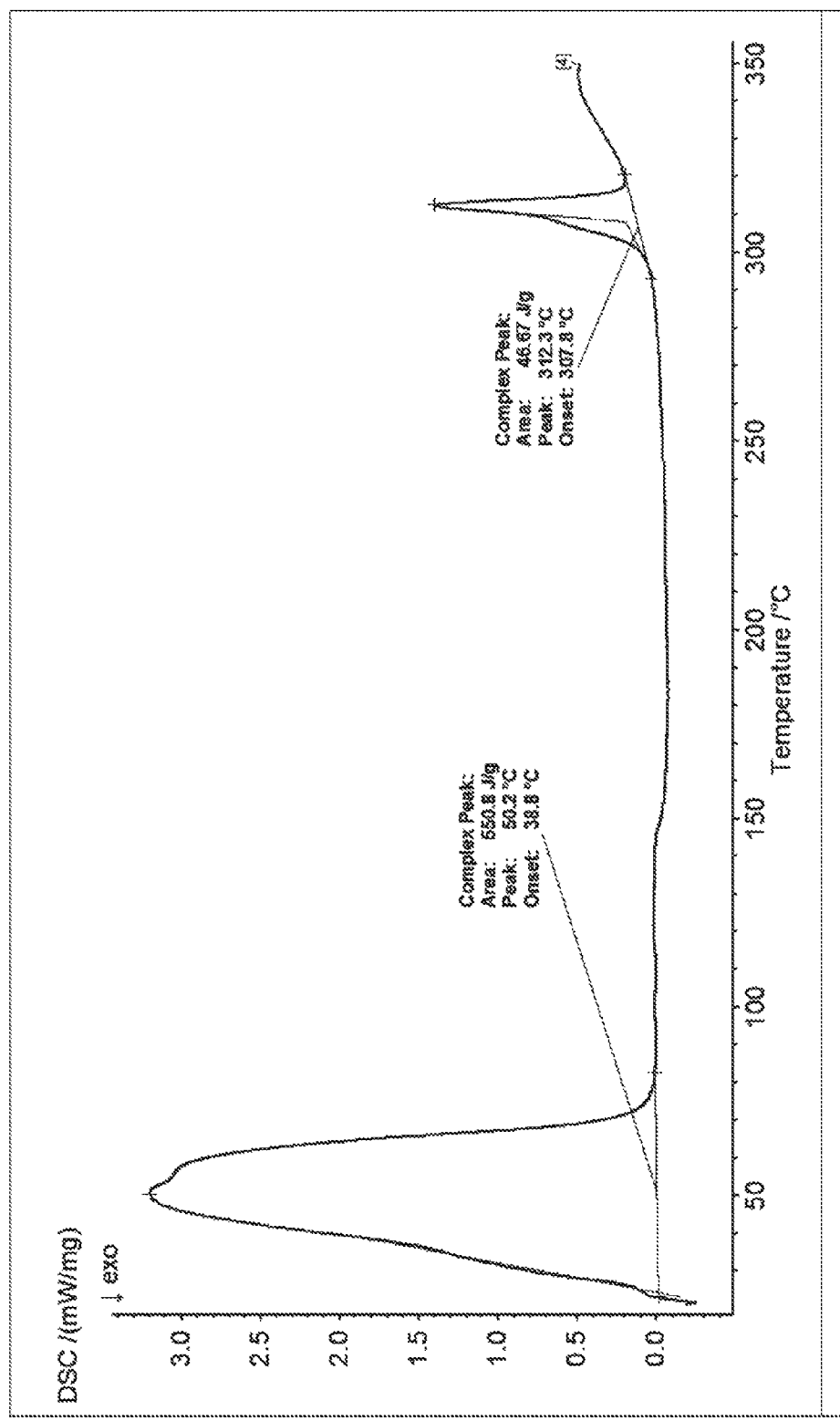
FIG. 42: shows the differential scanning calorimetry (DSC) profile of the hydrated crystalline form SII of NaHDC.
Figure 43:
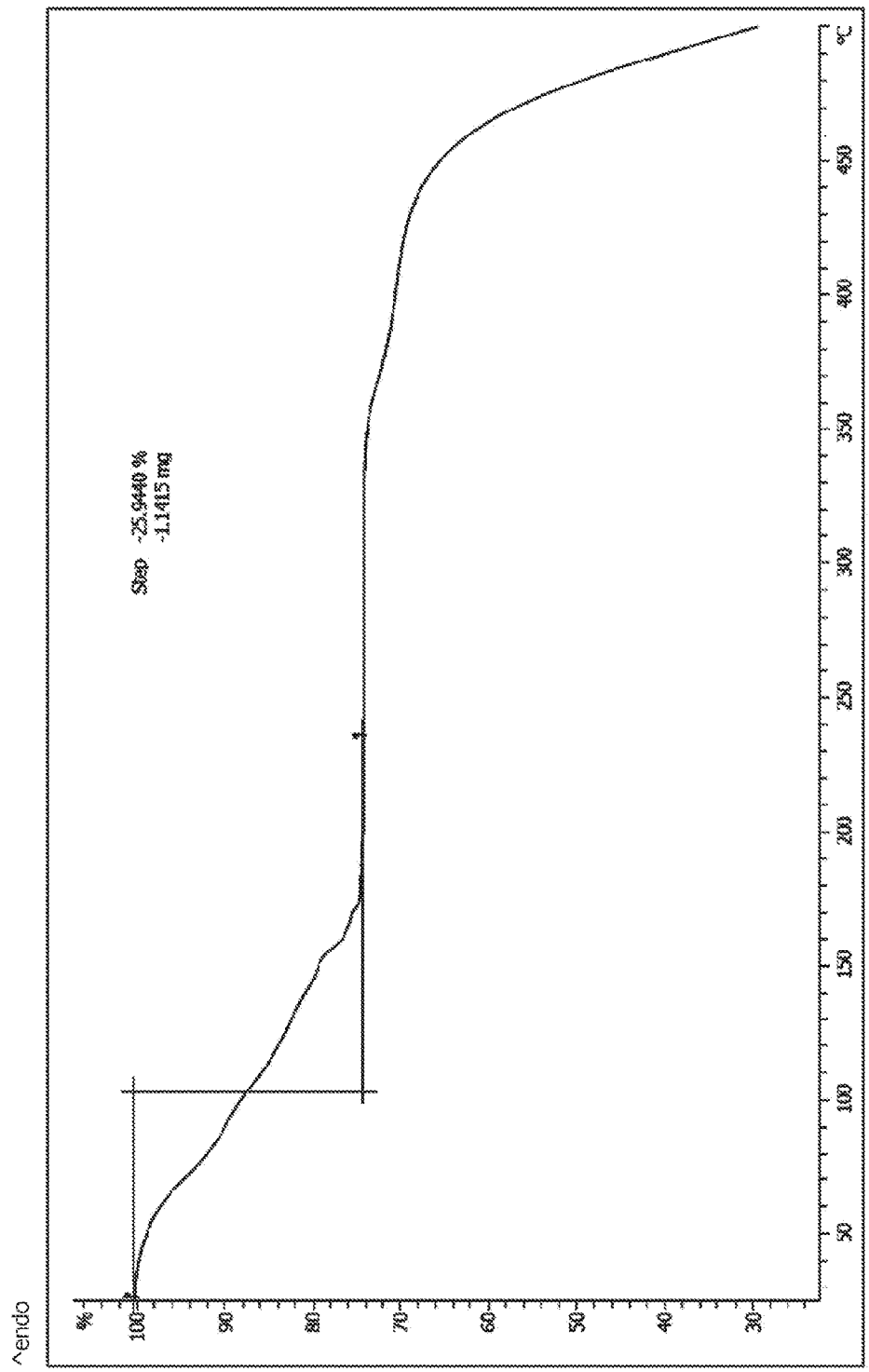
FIG. 43: shows the thermogravimetric profile (TGA) of the hydrated crystalline form SII of NaHDC.
Figure 44:
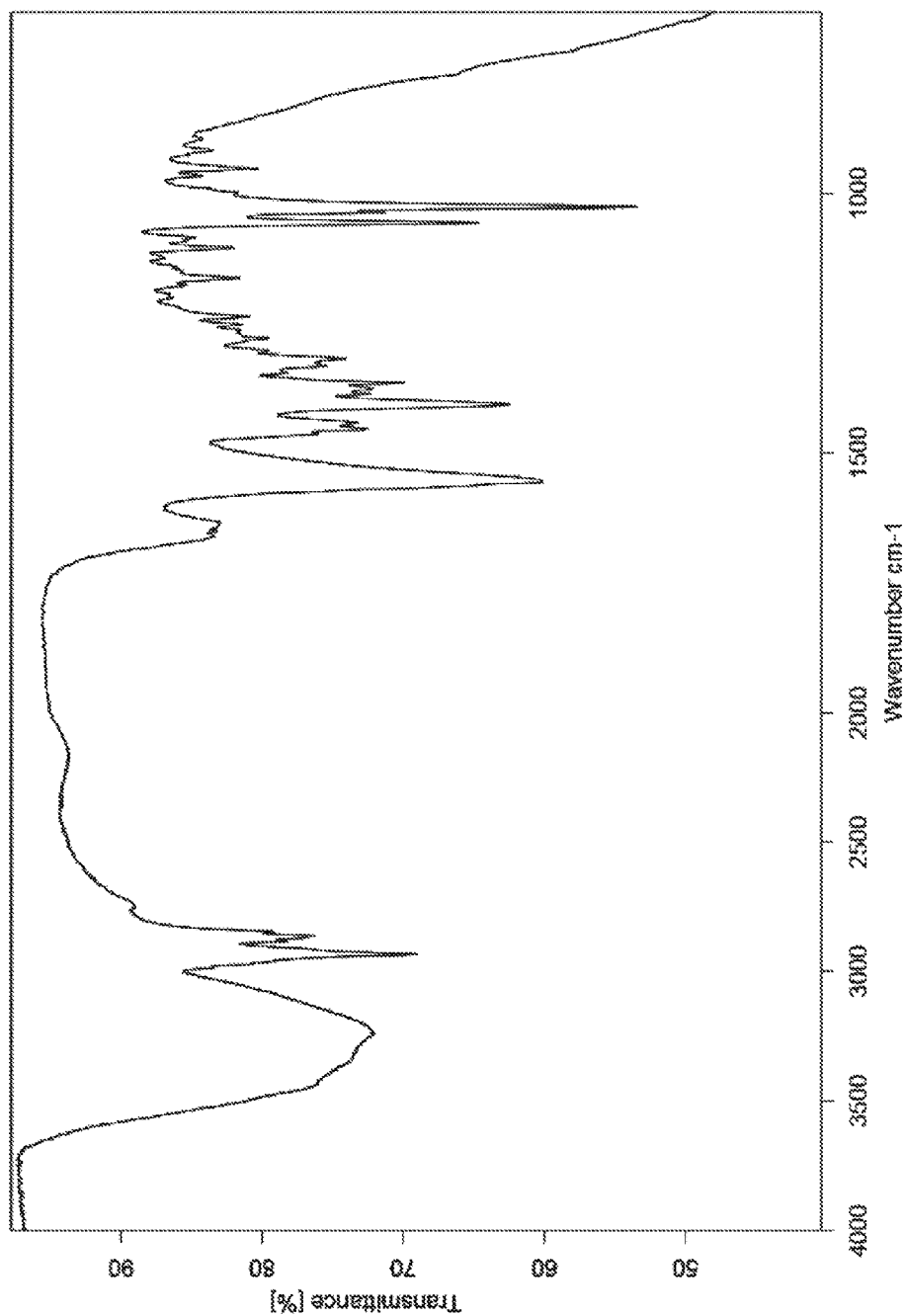
FIG. 44: shows the FT-IR/ATR spectrum of the hydrated crystalline form SII (SII) of NaHDC.

The hydrated polymorphic form SII of NaHDC is characterised by an X-ray powder diffractogram (XPRD) profile as given as an example in FIG. 40, and/or by a differential scanning calorimetry (DSC) profile as given as an example in FIG. 42, and/or by a thermogravimetric profile (TGA) as given as an example in FIG. 43 and/or by an FT-IR/ATR spectrum as shown in FIG. 44.

The hydrated polymorphic form SII of NaHDC is characterised by the XPRD profile shown in FIG. 40, the characteristic peaks of which are found at the following 2 theta positions in FIG. 41: 4.88; 8.81; 12.82; 15.30; 15.47; 16.24; 17.45; 19.12; 19.52; 20.05; 20.83; 21.68; 22.32; 22.95; 25.30; 26.64; 27.33; 27.64; 28.07; 29.75 degrees, with a margin of error on the value indicated for each peak of ±0.20 degrees 2 theta.

FIG. 41 shows the values of the aforementioned XPRD peaks of the hydrated polymorphic form SII, together with the corresponding relative intensity.

The hydrated polymorphic form SII of NaHDC is characterised by the DSC profile shown in FIG. 42. In such a graph it is possible to see an endothermic event at about 50° C. (Complex Peak onset 38.8° C., Peak 50.2° C. and enthalpy 550.8 Joule/g associated with the loss of water and an endothermic peak at about 310° C. with Peak onset at 307.8° C., Peak at 312.3° C. and enthalpy of fusion equal to 46.67 Joule/g, due to the melting of the anhydrous form FI into which the hydrated form SII interconverts.

The hydrated polymorphic form SII of NaHDC is characterised by the TGA profile shown in FIG. 43. The TGA profile shows an initial weight loss at about 100° C., of about 25% attributable to the loss of water of such a form.

The hydrated polymorphic form SII of NaHDC is characterised by the FT-IR/ATR spectrum shown in FIG. 44.

Sodium hyodeoxycholate in the amorphous form.

Figure 45:
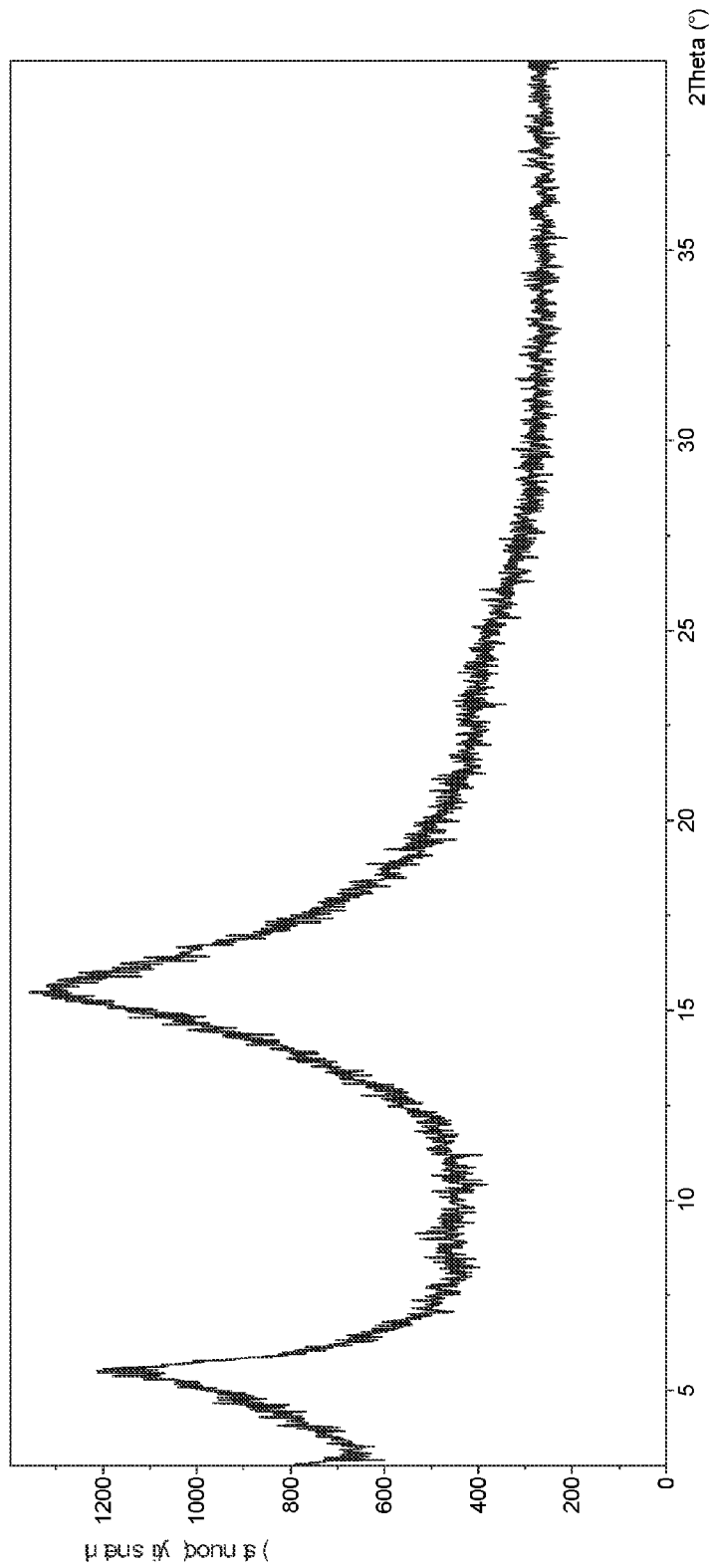
FIG. 45: shows the X-ray powder diffractogram (XPRD) of the amorphous form of NaHDC.
Figure 47:
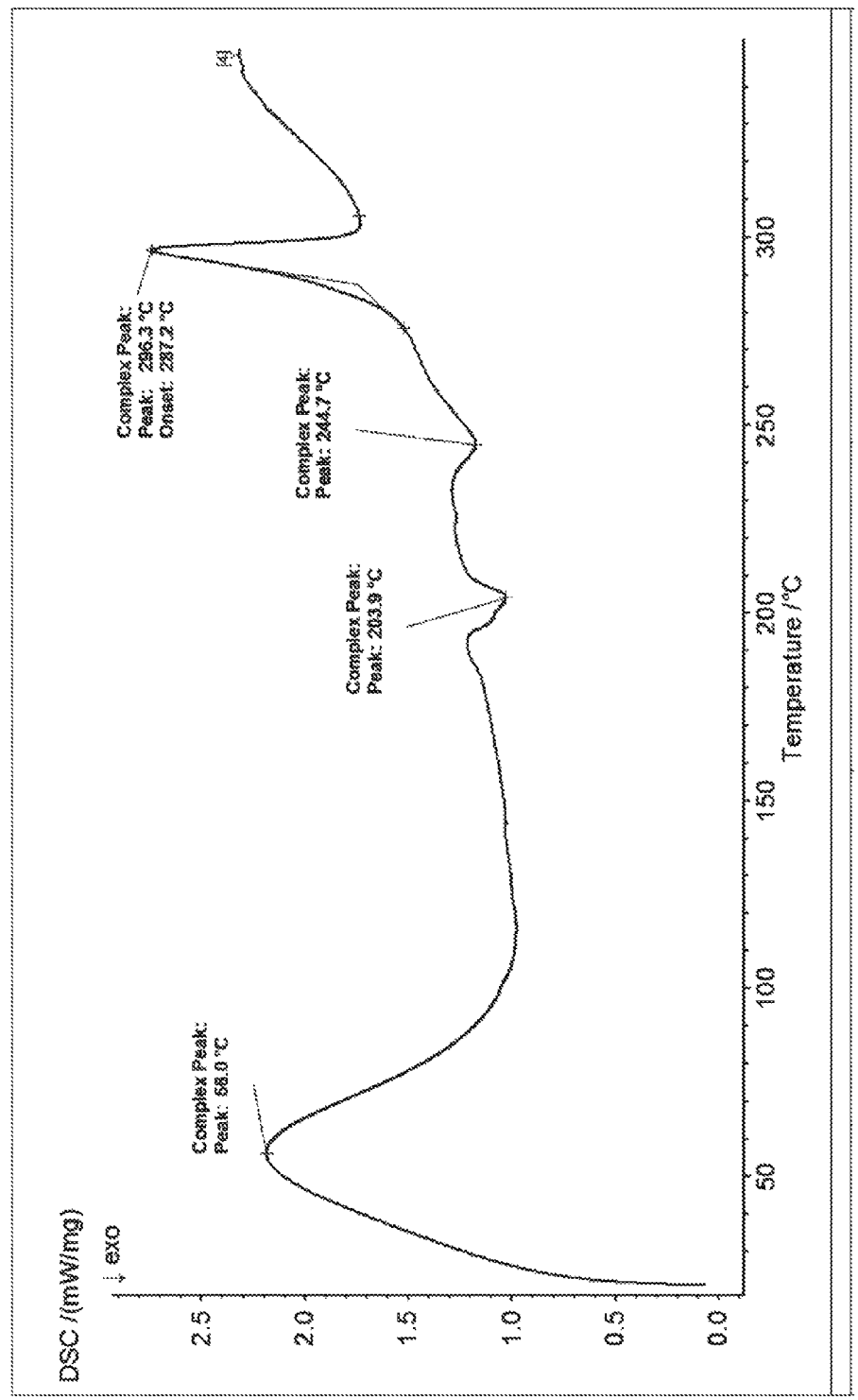
FIG. 47: shows the differential scanning calorimetry (DSC) profile of the amorphous form of NaHDC.
Figure 48:
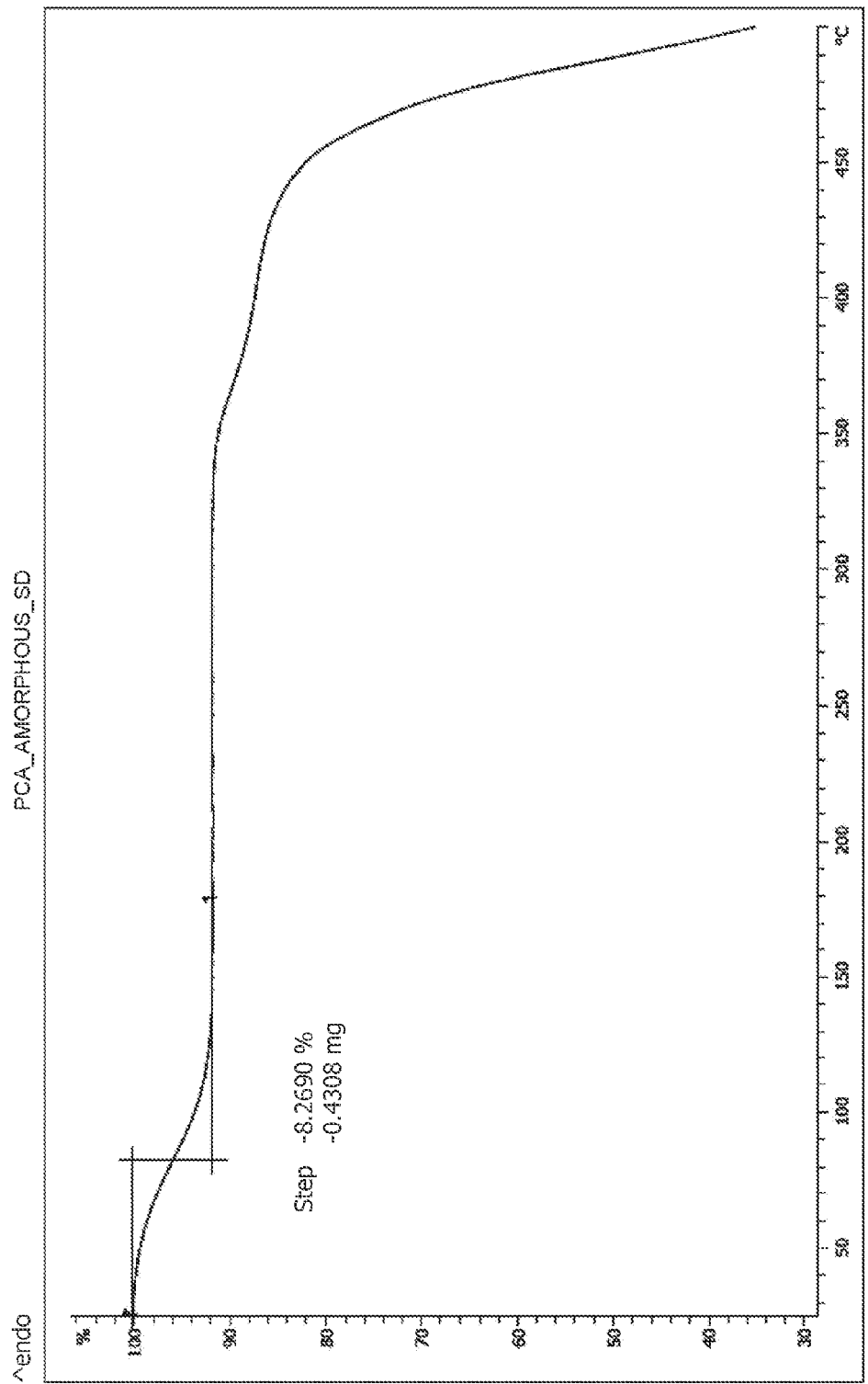
FIG. 48: shows the thermogravimetric profile (TGA) of the amorphous form of NaHDC.
Figure 49:
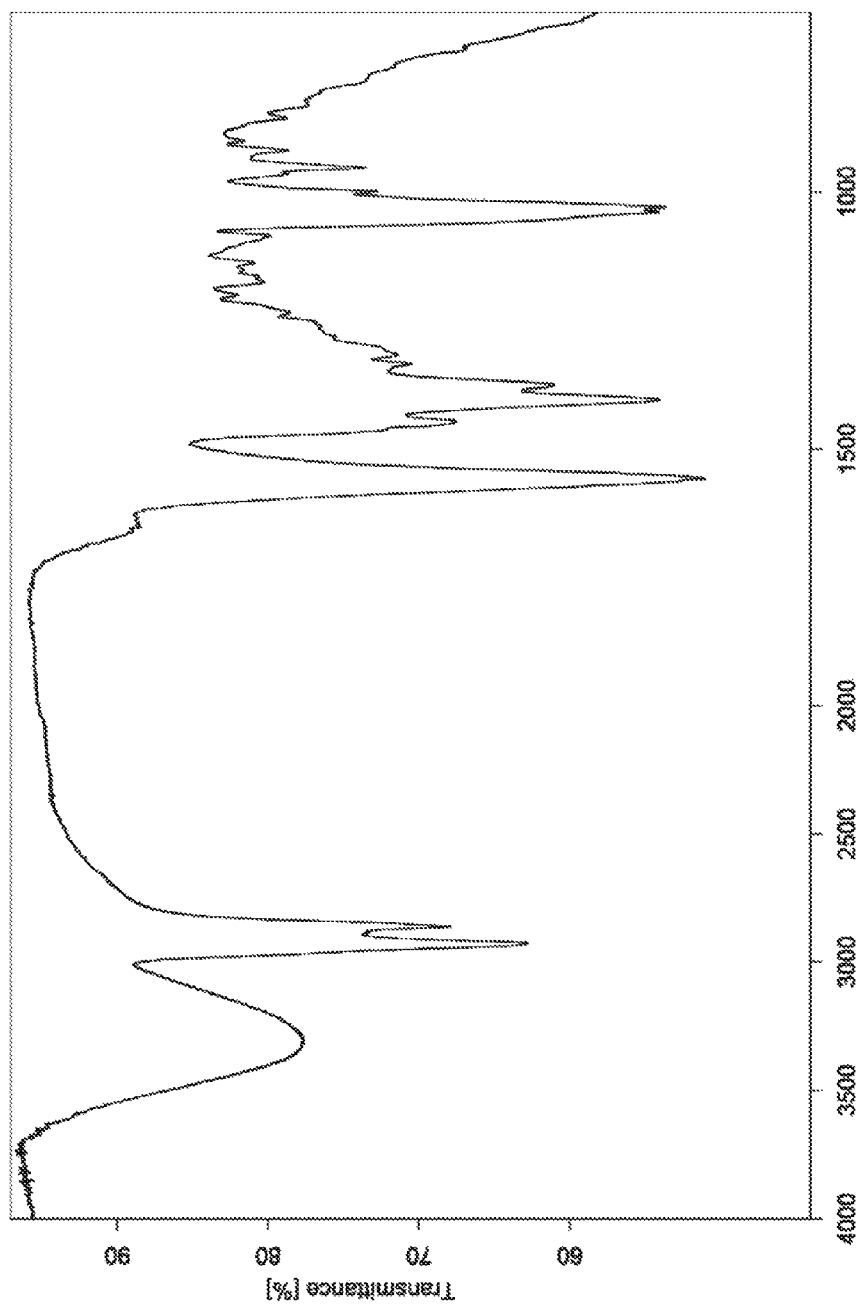
FIG. 49: shows the FT-IR/ATR spectrum of the amorphous form of NaHDC.
Figure 51:
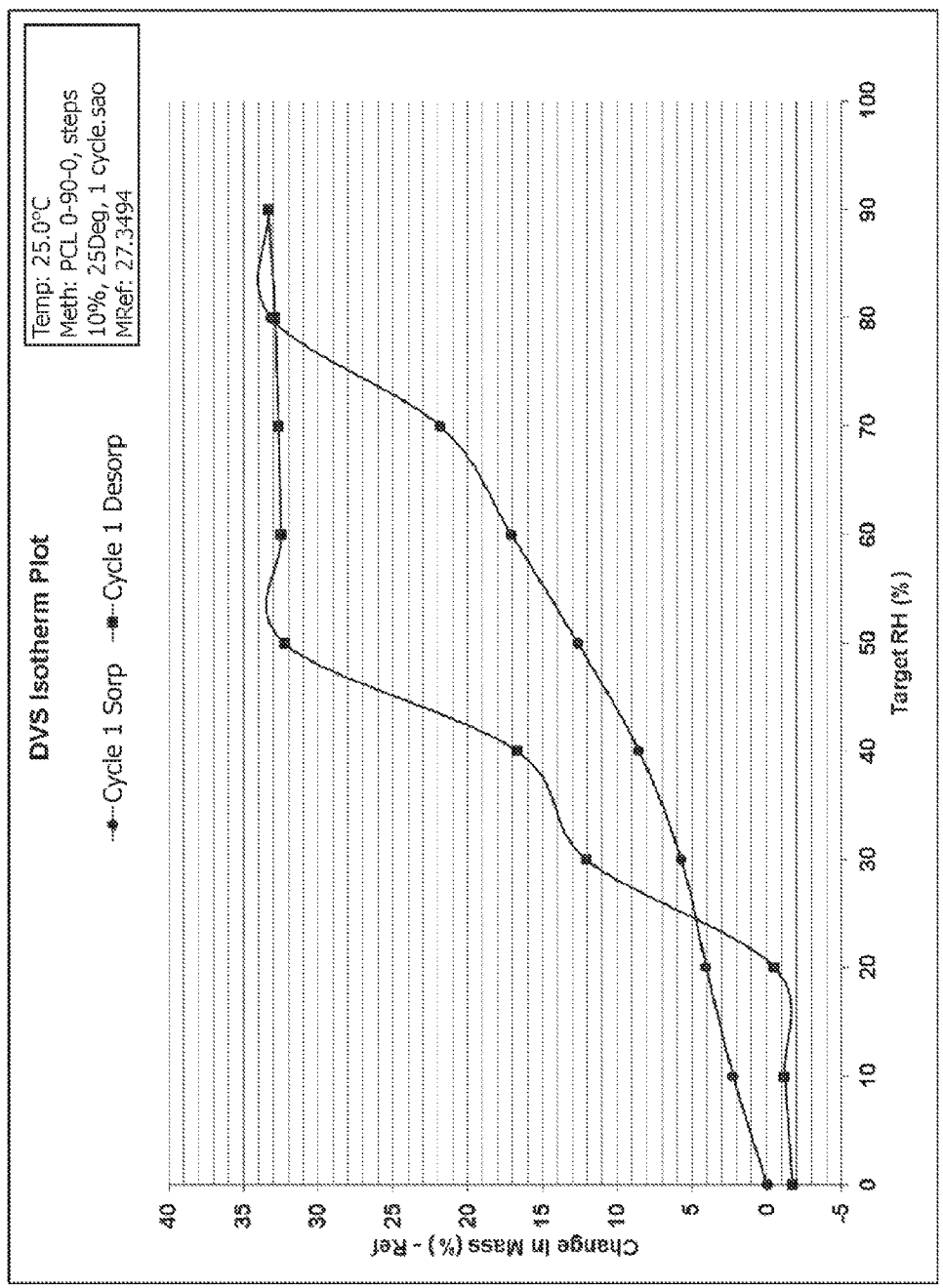
FIG. 51: isotherm at 25° C. amorphous form of NaHDC.

The amorphous form of NaHDC is characterised by an X-ray powder diffractogram (XPRD) profile as given as an example in FIG. 45, and/or by a differential scanning calorimetry (DSC) profile as given as an example in FIG. 47, and/or by a thermogravimetric profile (TGA) as given as an example in FIG. 48 and/or by an FT-IR/ATR spectrum as shown in FIG. 49, by a dynamic vapour sorption (DVS) analysis in isotherm at 25° C. as given as an example in FIG. 51.

Figure 46:
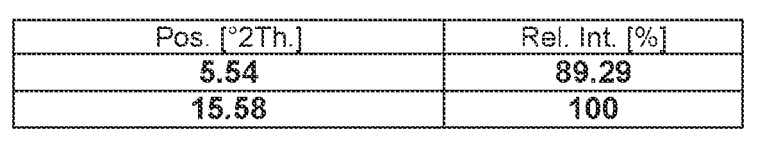

The amorphous form of NaHDC is characterised by the XPRD profile shown in FIG. 45, the characteristic peaks of which are found at the following 2 theta positions in FIG. 46: 5.54; 15.58 degrees, with a margin of error on the value indicated for each peak of ±0.20 degrees 2 theta.

FIG. 46 shows the values of the aforementioned XPRD peaks of the amorphous form, together with the corresponding relative intensity.

The amorphous form of NaHDC is characterised by the DSC profile shown in FIG. 47. In such a graph it is possible to see an endothermic event at about 50° C. (Complex Peak 56.0° C. associated with the loss of water. Moreover, it has two exothermic peaks (Complex Peak 203.9° C. and 244.7° C.) after 200° C. probably associated with the recrystallization of the amorph and an endothermic event at about 300° C. with Peak onset at 287.2° C., Peak at 296.3° C. due to fusion.

The amorphous form of NaHDC is characterised by the TGA profile shown in FIG. 48. The TGA profile shows an initial weight loss at about 80° C. of about 8% attributable to the loss of water.

The amorphous form of NaHDC is characterised by the FT-IR/ATR spectrum shown in FIG. 49, the characteristic peaks of which are found at the following frequencies in FIG. 50: 3316.7; 2928.4; 2863.6; 1557.3; 1446.2; 1404.4; 1374.4; 1334.4; 1316.9; 1038.4; 1029.3; 998.7.1; 952.8; 912.2 cm$^{-1}$ with a margin of error on the value indicated for each peak of ±1 cm$^{-1}$.

The amorphous form of NaHDC is characterised by the DVS graph in isotherm at 25° C.±0.1 as given as an example in FIG. 51 and by the corresponding values expressed in % as shown in FIG. 52.

In sorption, at 30% RH, the sample shows a weight change of about 6% and at 70% RH of 22%. At 90% RH there is a weight change of about 35%. In desorption the sample is stable up to 50% RH preserving the weight change of about 34% (which corresponds to about 8 water molecules). At about 40% RH it is possible to see an inflection, and at this point the sample seems to still contain about 17% water (which corresponds to about 4 water molecules). At 0% RH the sample shows a weight that is less than the starting weight.

Sodium hyodeoxycholate obtained before the last reprecipitation stage, which takes place for example in acetone under heat, is a complex mixture of the different forms described.

The amount of water in the NaHDC crystal mixture is less than 5%, preferably less than 3% and even more preferably it is less than 2%, where said percentages are in relation to the total weight of the crystal.

Figure 53:
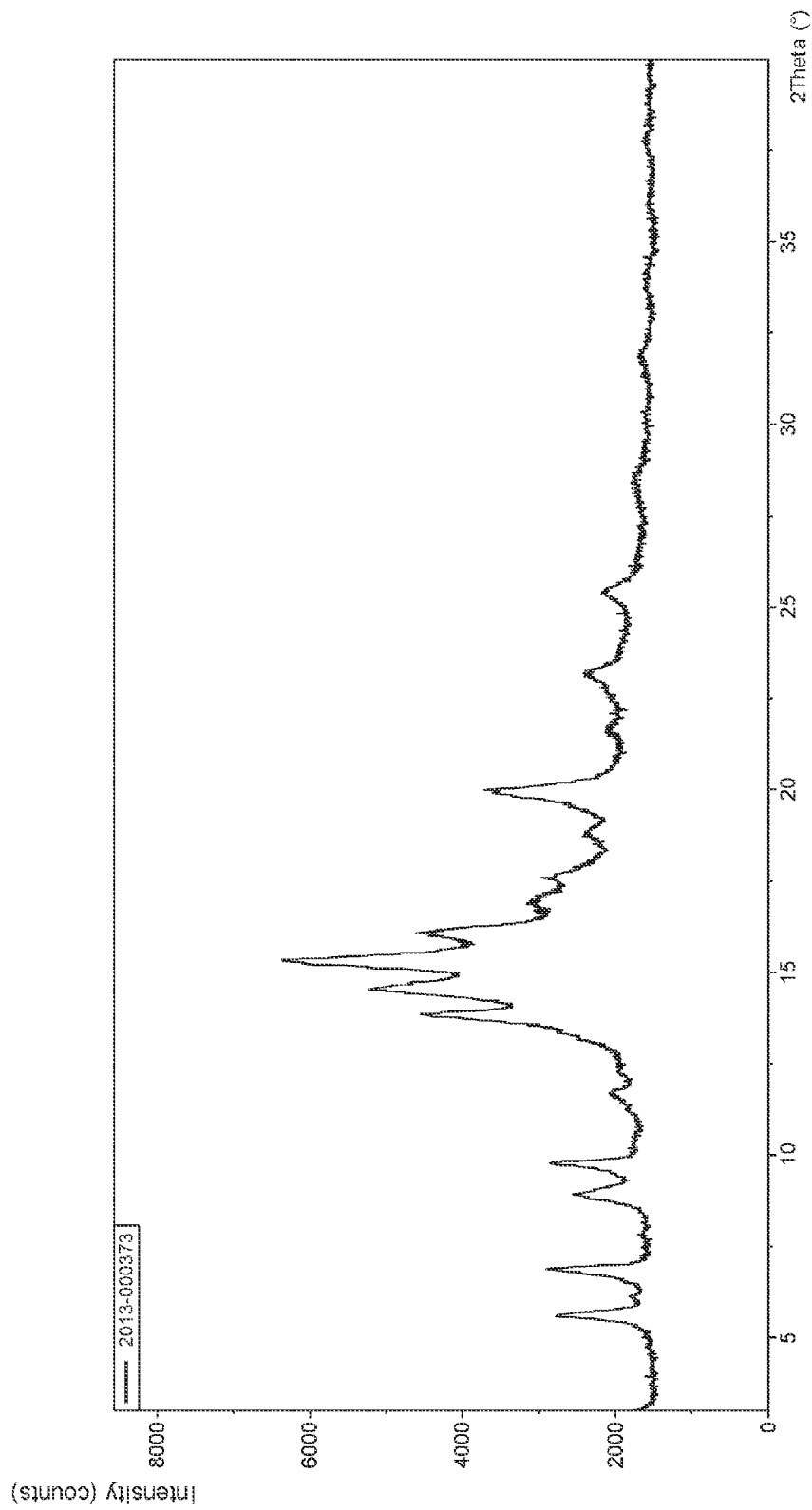
FIG. 53: shows the X-ray powder diffractogram (XPRD) of NaHDC mixture.
Figure 54:
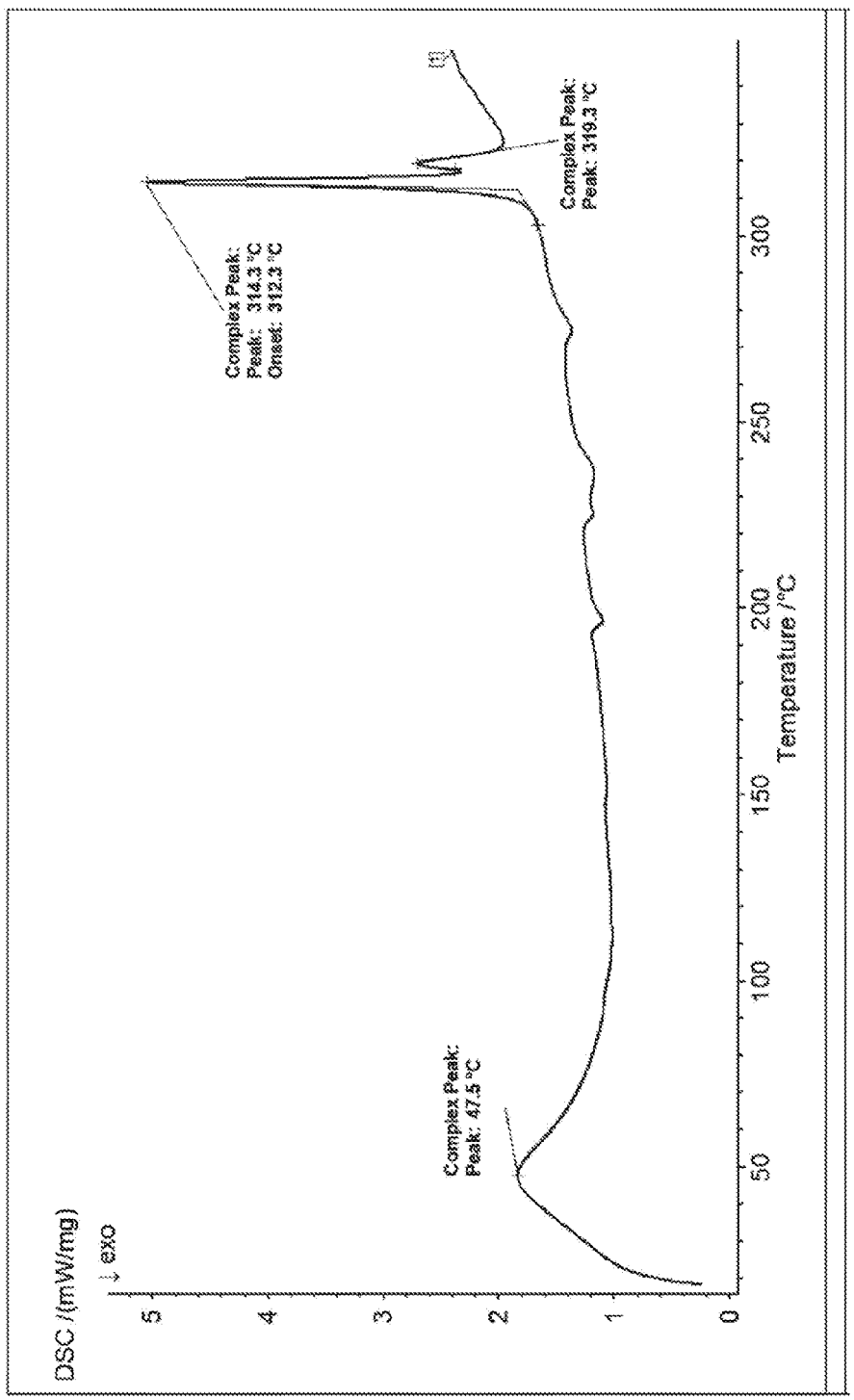
FIG. 54: shows the differential scanning calorimetry (DSC) profile of NaHDC mixture.
Figure 55:
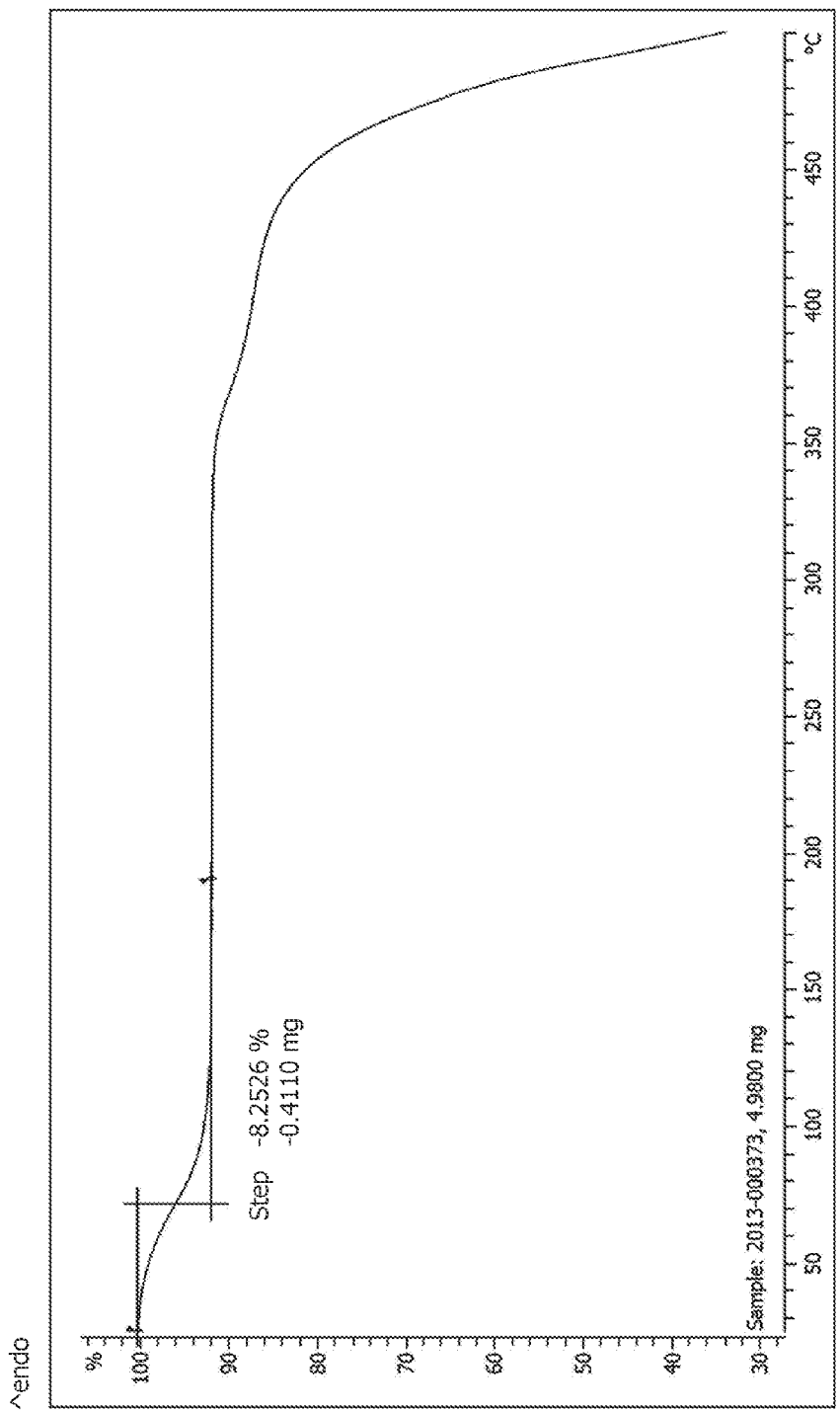
FIG. 55: shows the thermogravimetric profile (TGA) of NaHDC mixture.
Figure 56:
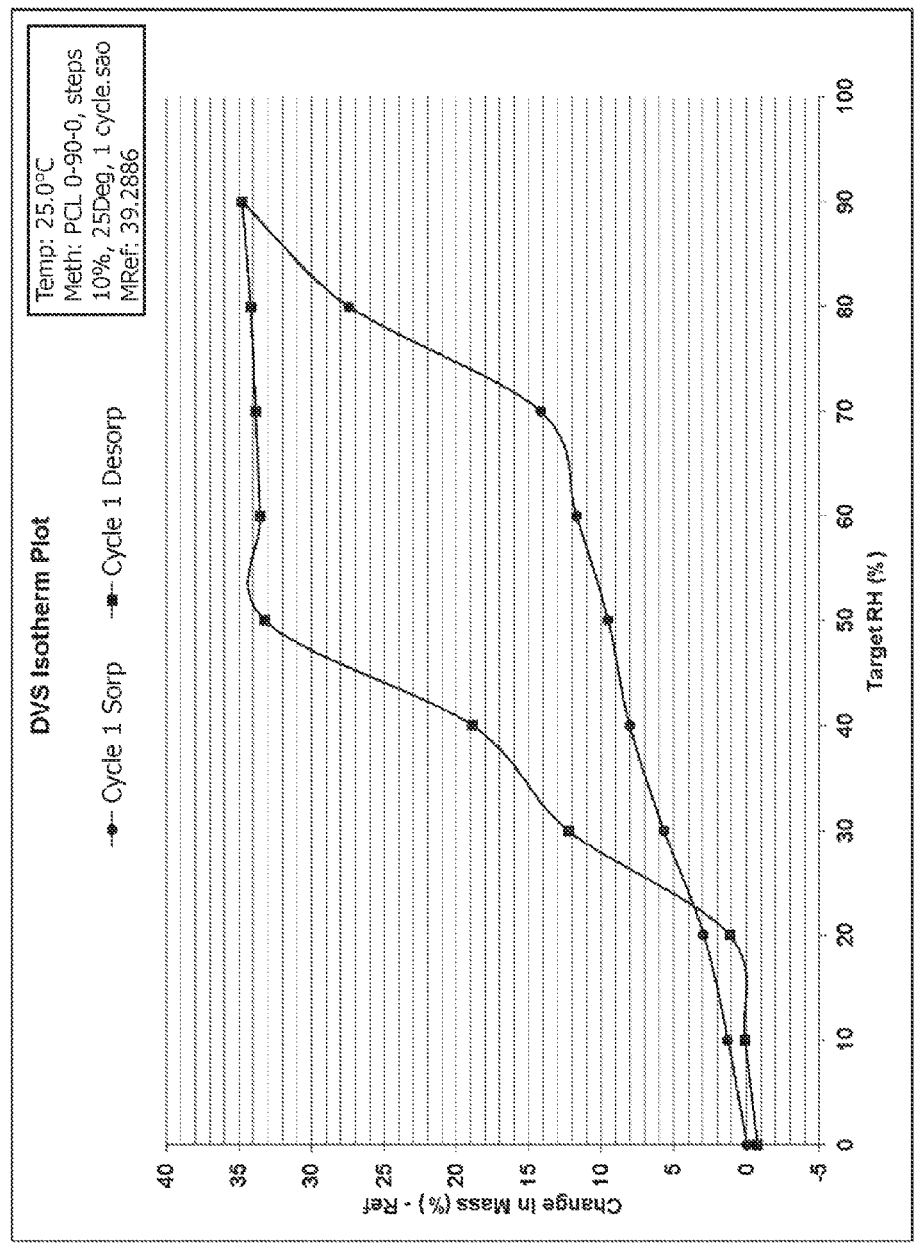
FIG. 56: isotherm at 25° C. of NaHDC mixture.

Such a mixture of NaHDC is characterised by an X-ray powder diffractogram (XPRD) profile as given as an example in FIG. 53, and/or by a differential scanning calorimetry (DSC) profile as given as an example in FIG. 54, and/or by a thermogravimetric profile (TGA) as given as an example in FIG. 55 and/or by a dynamic vapour sorption (DVS) analysis in isotherm at 25° C. as given as an example in FIG. 56. Moreover, there is a description of the comparison of the dynamic vapour sorption (DVS) analysis in isotherm at 25° C. of the mixture of different forms and the anhydrous crystalline form FII as given as an example in FIG. 58.

Such a mixture of NaHDC forms is characterised by the XPRD profile shown in FIG. 53.

The mixture of forms of NaHDC is characterised by the DSC profile shown in FIG. 54. In such a graph it is possible to see an endothermic event at about 50° C. associated with the loss of water (Complex Peak 47.5° C.), two exothermic events after 200° C. probably associated with the recrystallization of the amorph and an endothermic event characterised by a double peak at a temperature of over 310° C. due to fusion (Complex Peak onset 312.3° C., Peak 314.3° C., Peak 319.3° C.)

The mixture of forms of NaHDC is characterised by the TGA profile shown in FIG. 55. The TGA profile shows an initial weight loss at about 70° C. of about 8% attributable to water.

The mixtures of forms of NaHDC is characterised by the DVS graph in isotherm at 25° C.±0.1 as given as an example in FIG. 56 and by the corresponding values expressed in % as shown in FIG. 57.

In sorption at 20% RH, the sample shows a weight change of about 3% and at 70% RH of 15%. At 90% RH there is a weight change of about 35%. In desorption the sample is stable up to 50% RH having the weight increase of about 34% (which corresponds to about 8 water molecules), after about 40% RH it is possible to see an inflection and the sample seems to contain about 18% water (which corresponds to about 4 water molecules).

Figure 58:
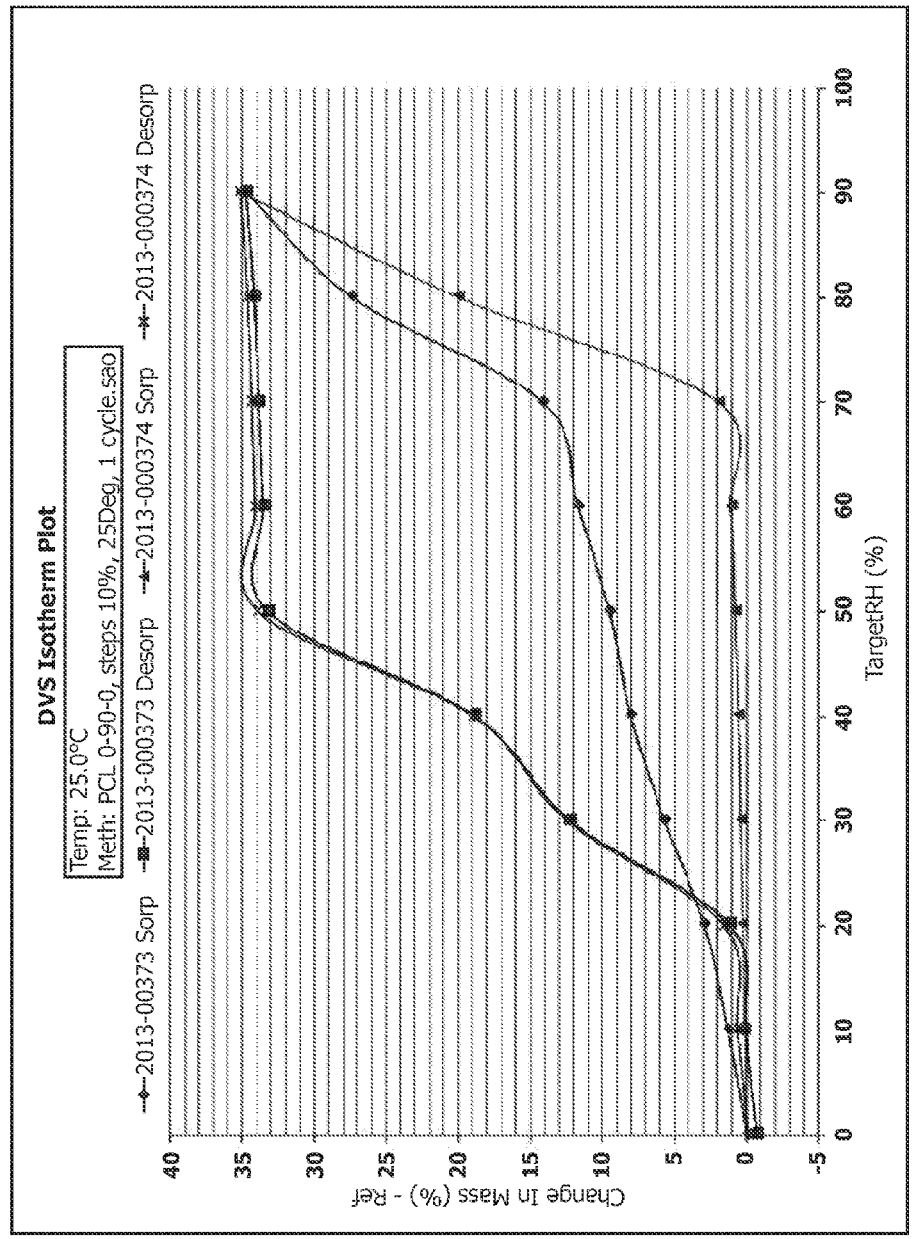
FIG. 58: isotherm comparison at 25° C. of NaHDC mixture and anhydrous form FII of NaHDC.

Moreover, a comparison was carried out in isotherm at 25° C. of the mixture of forms and the polymorphic form FII of NaHDC as shown in FIG. 58. For comparative purposes, FIG. 58 shows the DVS profile of crude NaHDC, which as explained is a complex and irreproducible mixture of the different forms that has a chemical purity of 99.5%. This mixture is obtained industrially before final reprecipitation under heat of the reaction mass, for example in acetone, under reflux.

Such crude NaHDC is a mixture of anhydrous and hydrated polymorphic forms and potentially with immeasurable percentages of amorphous part. The mixtures of polymorphic forms, hydrated and amorphous, cannot be formulated so as to obtain a univocal product to be used in clinical trials that are carried out before commercialisation of a medicine. Therefore, the present invention has the advantage of offering a new stable anhydrous polymorphic form of NaHDC, i.e. the polymorphic form FII, with high chemical and polymorphic purity, suitable for pharmaceutical formulation.

As given as an example in the experimental part, the polymorphic form FII is the preferred form for the formulation as active ingredient, thanks also to its stability over time and to the temperature (stable up to 260° C.): it is the form that is most thermodynamically stable at room temperature (as already described) and most stable with regard to humidity having a surprising and unforeseeable stability with regard to humidity both at 25° C. and at 40° C., as demonstrated by the tests carried out according to the guidelines ICH Q1A (version 4, 6 Feb. 2003) for carrying out the stability tests of new pharmaceutical compounds at 25° C./60% RH and 40° C./75% RH.

Moreover, the synthesis process of the new polymorphic form FII of NaHDC described hereafter, makes it possible to obtain such an active ingredient with an optimal particle size for the pharmaceutical formulation, thus avoiding the need for processes to control particle size, such as grinding, micronization or sieving, which can jeopardise the polymorphic purity and the chemical purity of the polymorphic form FII due to the large amount of energy involved in these operations.

The synthesis process of the polymorphic form FII of NaHDC of the present invention comprises a final reprecipitation step by an organic solvent selected from a ketonic solvent, a solvent belonging to the category of esters, an alcohol, a solvent belonging to the category of nitriles or they mixture.

Preferably, the ketonic solvent has chain $C_3$-$C_6$, the solvent belonging to the category of esters has chain $C_2$-$C_5$, the alcoholic solvent has chain $C_1$-$C_5$ and/or the solvent belonging to the category of nitriles has chain $C_2$-$C_3$.

More preferably, the ketonic solvent is selected from acetone, methyl-iso-butyl ketone (MIBK), methyl-ethyl-ketone (MEK) or their mixtures, the solvent belonging to the category of esters is selected from ethyl acetate, ethyl formate, propyl acetate or their mixtures, the alcoholic solvent is selected from methanol, ethanol, 1-propyl alcohol (1-propanol), isopropyl alcohol (2-propanol), 1-butanol, 2-butanol, 2-pentanol or their mixtures, and/or the solvent belonging to the category of nitriles is selected from acetonitrile, propionitrile or their mixtures.

The preferred organic solvent are the ketones and even more preferred is acetone under heat.

The preferred temperature at which the reprecipitation of NaHDC anhydrous crystalline form II is carried out is comprised in the range between 55 and 120° C. Generally, it is preferred to use a temperature close to the reflux temperature of each solvent.

When acetone is used, the preferred temperature is comprised between 55 and 60° C., and even more preferably it is comprised between 55 and 56° C.

The reprecipitation takes place in a time comprised between 6 and 10 hours, more preferably between 6 and 8 hours.

Ketonic solvents are preferred and among these acetone is the preferred solvent.

In particular, the preferred ratio of NaHDC and solvent, which preferably is ketonic and even more preferably is anhydrous acetone, is 1 to 8 (weight of NaHDC with respect to the volume of solvent) and even more preferably it is 1 to 6 (weight of NaHDC with respect to the volume of solvent).

In a preferred embodiment, the process of the invention comprises the following steps:
a) at least one purification step of HDCA of formula II, carried out through preparation of a salt of an alkaline-earth metal of hyodeoxycholic acid and its subsequent acidification to obtain purified HDCA;
b) preparation of NaHDC through treatment of purified HDCA with NaOH up to pH comprised between 8.5 and 9.5;
c) obtaining the polymorphic form FII of NaHDC through reprecipitation by an organic solvent selected from a ketonic solvent, a solvent belonging to the category of esters, an alcohol, a solvent belonging to the category of nitriles or they mixture.

Preferably, in the above described step c) the ketonic solvent has chain $C_3$-$C_6$, the solvent belonging to the category of esters has chain $C_2$-$C_5$, the alcoholic solvent has chain $C_1$-$C_5$ and/or the solvent belonging to the category of nitriles has chain $C_2$-$C_3$.

More preferably, in the above described step c) the ketonic solvent is selected from acetone, methyl-iso-butyl ketone (MIBK), methyl-ethyl-ketone (MEK) or their mixtures, the solvent belonging to the category of esters is selected from ethyl acetate, ethyl formate, propyl acetate or their mixtures, the alcoholic solvent is selected from methanol, ethanol, 1-propyl alcohol (1-propanol), isopropyl alcohol (2-propanol), 1-butanol, 2-butanol, 2-pentanol or their mixtures, and/or the solvent belonging to the category of nitriles is selected from acetonitrile, propionitrile or their mixtures.

In a more preferred embodiment of the process of the invention indicated above, step c) is carried out at a temperature comprised between 55 and 120° C., for a time comprised between 6 and 10 hours.

The preferred salt of an alkaline-earth metal of hyodeoxycholic acid to be used in step a) is the magnesium salt of hyodeoxycholic acid of formula III ($(HDC)_2Mg$).

The purification carried out in step a) is carried out through salification of HDCA with a base, obtaining the salt of an alkaline-earth metal of hyodeoxycholic acid, preferably of formula III ($(HDC)_2Mg$), and its acidification to obtain purified HDCA.

Preferably, the starting HDCA of stage a) has a chemical purity comprised between 80 and 90% and it can be obtained according to the methods of the prior art.

Preferably, the HDCA obtained at the end of step a) has a final chemical purity comprised between 99.5% and 99.9%.

Step a) is preferably repeated twice.

In this last case, starting from a chemical purity of HDCA comprised between 80 and 90%, after the first purification a chemical purity of HDCA comprised between 98.5% and 99.0% is obtained, and after the second purification a chemical purity comprised between 99.5% and 99.9% is obtained.

In step b) NaHDC with chemical purity comprised between 99.5% and 99.9% is preferably obtained.

In step c) the polymorphic form FII of NaHDC preferably with a chemical purity comprised between 99.5% and 99.9% is obtained.

In step a) the bases used in the invention are preferably inorganic bases, like for example NaOH, KOH, $NH_3$, or organic ones, like for example a primary, secondary or tertiary amine, like for example isopropylamine, dimethylamine, triethylamine etc.

In a preferred embodiment of the process of the invention, the starting HDCA in step a) is added to with deionized or drinking water, by itself or in mixture with alcohols with chain $C_1$-$C_5$, like for example methanol, ethanol, 1-propyl alcohol (1-propanol), isopropyl alcohol (2-propanol), 1-butanol, 2-butanol, 2-pentanol etc., preferably ethanol.

The mixtures of water and alcohols, the preferred ones of which are water and ethanol, have a ratio that can vary from 7 to 2 volume/volume.

In these mixtures of water and alcohols, the preferred ones of which are water and ethanol, the ratio between the weight of HDCA with respect to the total volume of solvent (water and alcohols) varies between 1:9 and 1:25. Said mixtures of water and alcohols are preferably used at room temperature (20-25° C.).

Then a base is added, which as indicated above can be an inorganic or organic base.

In step a) the base is added in a stoichiometric amount, preferably comprised between 1 and 1.3 equivalents with respect to each equivalent of HDCA and even more preferably between 1.0 and 1.1 equivalents for each equivalent of starting HDCA.

The suspension obtained with HDCA and the selected base, possibly added to with water by itself or in mixture with alcohols as indicated above, is left under stirring for a time preferably comprised between 30 and minutes, at a temperature preferably comprised between 60 and 90° C., until a clear solution is obtained, named "Solution A", with a pH preferably comprised between 6.5 and 8.5, even more preferably of 7.5.

In another reactor a stoichiometric amount of a salt of an alkaline-earth metal, preferably magnesium, preferably comprised between 1 and 1.3 equivalents with respect to each equivalent of starting HDCA and even more preferably between 1 and 1.1 equivalents, is added to an amount of water comprised between 10 to 15 volumes of deionized or drinking water, with respect to the dry weight of salt of the alkaline-earth metal, at room temperature. A clear solution named "Solution B" is thus obtained.

The salt of an alkaline-earth metal, preferably magnesium, added to the water, can for example be a sulphate salt or a hydrochloride salt, like for example magnesium sulphate heptahydrate, magnesium chloride, etc.

The addition of solution B to solution A is preferably carried out at a temperature comprised between 60 and 90° C., in a time preferably comprised between 20 and 50 minutes, and it makes it possible to obtain an aqueous or hydroalcoholic suspension of the salt of an alkaline-earth metal, preferably magnesium, of hyodeoxycholic acid.

The final pH of this suspension is preferably comprised between 5 and 7.

After having kept this suspension at the temperature of 60-90° C. for a further time of 30-60 minutes, it is cooled to room temperature in 2-4 hours and the salt of an alkaline-earth metal, preferably magnesium, of hyodeoxycholic acid is recovered, as a white solid, for example by filtration.

The subsequent suspension in water of the salt of an alkaline-earth metal of hyodeoxycholic acid, preferably the magnesium salt of formula III, in a ratio of from 1 to 5 to 1 to 10 (weight of HDCA with respect to the volume of water), followed by a slight heating under stirring, preferably up to 60-80° C., and by the addition of a mineral acid, up to pH comprised between 1 and 2, makes it possible to obtain, after cooling to room temperature in a time of 1-2 hours, purified HDCA as a white solid, for example by filtration.

Particularly preferred mineral acids are hydrochloric acid, sulphuric acid or phosphoric acid etc. and the preferred amount of mineral acid used is comprised between 1 and 1.5 equivalents with respect to each equivalent of the magnesium salt di formula III, even more preferably comprised between 1 and 1.3 equivalents.

Purified HDCA is preferably recovered by filtration and the residue on the filter is washed with water up to pH neutral to remove the residual acidity.

After this first purification, in the case of starting HDCA with a chemical purity comprised between and 90%, HDCA with a chemical purity comprised between 98.5% and 99.0% is obtained.

The repetition of step a), preferably carried out in its preferred form, on HDCA of chemical purity between 98.5% and 99.0% obtained after the first purification, makes it possible to obtain final HDCA in step a) with chemical purity comprised between 99.5% and 99.9%.

The next step, i.e. step b), contemplates the preparation of NaHDC through treatment of purified HDCA with base. Preferably, the purified HDCA coming from step a) has a chemical purity comprised between 99.5% and 99.9%.

In a preferred embodiment of the process of the invention, purified HDCA coming from step a) is added to water, preferably deionized, under stirring, at room temperature (20-25° C.), where the water is present in a ratio from 1 to 4 to 1 to 8, (weight of HDCA with respect to the volume of water).

The use in this step of deionized water makes it possible to obtain NaHDC in accordance with the specifications required for the classification of active pharmaceutical ingredient (API).

In step b) the base NaOH is added in a stoichiometric amount, preferably comprised between 1 and 1.1 equivalents with respect to each equivalent of HDCA.

The suspension obtained is left under stirring for a time preferably comprised between 30 and 60 minutes, at a temperature comprised between 40 and 70° C., until a clear solution is obtained, with a final pH comprised between 8.5 and 9.5.

A vacuum distillation of the water present is carried out, at −1/−0.9 bar with respect to ambient pressure until a highly viscous oily residue is obtained.

Then organic solvent is added to the oily residue, in a time comprised between 3 and 6 hours, in a ratio of from 1 to 6 to 1 to 8 (weight of HDCA with respect to the volume of solvent), preferably in a ratio of 1 to 6 (weight of HDCA with respect to the volume of solvent), at a temperature preferably comprised between 45 and 50° C., thus obtaining a slightly cloudy solution.

Preferably, the solvent used in this part of stage b) is an organic solvent, like for example a ketonic solvent, preferably with chain $C_3$-$C_6$, like for example acetone, methyl-iso-butyl ketone (MIBK), methyl-ethyl-ketone (MEK), etc., a solvent belonging to the category of esters, preferably with chain $C_2$-$C_5$, like for example ethyl acetate, ethyl formate, propyl acetate etc., an alcohol, preferably with chain $C_1$-$C_5$, like for example methanol, ethanol, 1-propyl alcohol (1-propanol), isopropyl alcohol (2-propanol), 1-butanol, 2-butanol, 2-pentanol etc., a nitrile with chain $C_2$-$C_3$, like for example acetonitrile, propionitrile etc.

The preferred temperature at which the precipitation of NaHDC takes place is comprised in the range between 55 and 120° C.

The preferred solvent is anhydrous acetone and in this case, the preferred temperature is comprised between 55 and 60° C., and even more preferably it is comprised between 55 and 56° C.

After slight heating, the solution is cooled to room temperature in a time comprised between 3 and 6 hours.

Then the precipitation of NaHDC is observed since the solvent used, preferably ketonic, is a non-solvent for this compound, in a time comprised between 8 and 10 hours.

The NaHDC product is recovered by filtration and the residue on the filter is washed with a solution of acetone/water 80:20 (v/v), preferably acetone/water 90:10 (v/v) and more preferably anhydrous acetone, then it is subjected to drying.

NaHDC thus obtained is a mixture of the six polymorphic forms described above, i.e. of the polymorphic forms FI, FII, FIII, SI, SII and the amorphous form and it is henceforth abbreviated as "NaHDC mixture".

The amount of water present in NaHDC mixture after drying is less than 5%, preferably less than 3% and even more preferably it is less than 2%, where said percentages are in relation to the total weight of the NaHDC mixture crystal.

Preferably, NaHDC mixture obtained at the end of step b) has a chemical purity comprised between 99.5% and 99.9%.

FIG. 54 shows the DSC profile of NaHDC mixture obtained by precipitation in the case in which the ketonic solvent used is anhydrous acetone without having carried out a further final reprecipitation of the dried NaHDC mixture product.

The polymorphic form FII of NaHDC is obtained in step c) through treatment of NaHDC mixture obtained in point b) with organic solvents, preferably ketonic.

Examples of organic solvents used to reprecipitate the polymorphic form FII of NaHDC, i.e. that act as non-solvents, are for example organic solvents selected from ketonic solvents, preferably with chain $C_3$-$C_6$, like for example acetone, methyl-iso-butyl ketone (MIBK) and methyl-ethyl-ketone (MEK), ester solvents, preferably with chain $C_2$-$C_5$, like for example ethyl acetate, ethyl formate and propyl acetate, alcohol solvents, preferably with chain $C_1$-$C_5$, like for example methanol, ethanol, 1-propyl alcohol (1-propanol), isopropyl alcohol (2-propanol), 1-butanol, 2-butanol and 2-pentanol and/or solvents belonging to the category of nitriles, preferably with chain $C_2$-$C_3$, like for example aceto nitrile and propionitrile.

The preferred temperature at which the reprecipitation of NaHDC anhydrous crystalline form II is carried out is comprised in the range between 55 and 120° C.

When acetone is used, the preferred temperature is comprised between 55 and 60° C., and even more preferably it is comprised between 55 and 56° C.

The reprecipitation takes place in a time comprised between 6 and 10 hours, more preferably between 6 and 8 hours.

Ketonic solvents are preferred and among these acetone is the preferred solvent.

In particular, the preferred ratio of NaHDC and solvent, which preferably is ketonic and even more preferably is anhydrous acetone, is 1 to 8 (weight of NaHDC with respect to the volume of solvent) and even more preferably it is 1 to 6 (weight of NaHDC with respect to the volume of solvent).

A suspension is obtained that is slowly heated to the reflux temperature of the solvent.

In the case in which the solvent is acetone, it is heated up to a temperature comprised between 55 and 60° C., preferably 55-56° C.

The suspension is then cooled to 25° C. in a time comprised between 3 and 6 hours.

The product is recovered by filtration and the residue on the filter is washed with a solution of acetone/water 80:20 (v/v), preferably acetone/water 90:10 (v/v) and more preferably anhydrous acetone.

NaHDC thus obtained is NaHDC anhydrous polymorphic form FII, with chemical purity preferably comprised between 99.5% and 99.9%.

The amount of water in the NaHDC form FII crystal is less than 1%, preferably less than 0.6% and even more preferably it is less than 0.4%, where said percentages are in relation to the total weight of the crystal.

Preferably, the polymorphic form FII of NaHDC of the present invention does not contain amorphous NaHDC.

Moreover, the polymorphic form FII of NaHDC of the present invention does not contain any of the other polymorphic forms of NaHDC described above.

Anhydrous NaHDC polymorphic form FII is a pure polymorph, where by the term "pure" we mean that anhydrous NaHDC polymorphic form FII preferably has an impurity content of less than 1%, even more preferably less than 0.7% and even more preferably less than 0.5% where these percentages are in relation to the total weight of the crystal.

Preferably, the amount of each single impurity in the polymorph FII of NaHDC is less than 0.5%, more preferably less than 0.3% and even more preferably less than 0.1%, where these percentages are in relation to the total weight of the crystal.

The impurities in the polymorph FII of NaHDC were determined as described in Table 1, and proved to be known impurities, such as chenodeoxycholic acid (3α,7α-dihydroxy-5β-cholan-24-oic acid, abbreviated with CDCA) and hyocholic acid (3α,6α,7α-trihydroxy-5β-cholan-24-oic acid, abbreviated with HCA) indicated in Table 1, and impurities (unknown) not known in a percentage amount of less than 0.01% or at the limit of detectability with reference to the total weight of the crystal.

Figure 59:
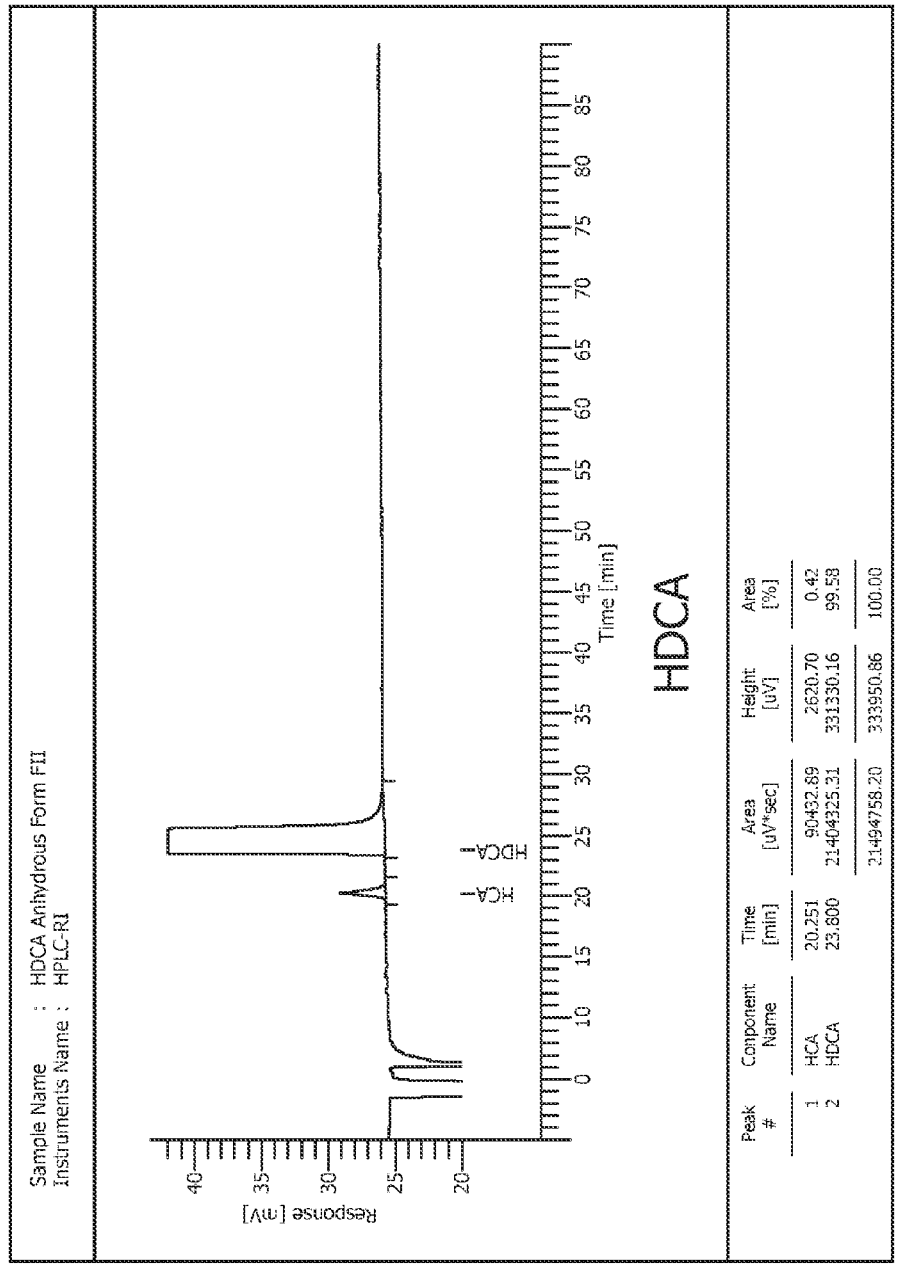
FIG. 59: HPLC (chromatogram) profile of the polymorphic form FII of NaHDC in acid form as HDCA.

The chemical purity profile is described in FIG. 59.

The purity of the polymorphic form FII of NaHDC obtained with the process of the present invention was evaluated through HPLC/RI (high-performance liquid chromatography/refractive index detector), through an analytical method described in FIG. 60, obtaining the results shown in the following Table 1:

TABLE 1

| Peak | Name of the component | Area [%] |
|---|---|---|
| 1 | HCA | 0.42 |
| 2 | HDCA | 99.58 |
| 3 | CDCA | n.a. |
| 4 | Σ (Unknown impurities) | <0.01% (n.a.) |

The other polymorphic forms described above were obtained according to the methods outlined hereafter.

The polymorphic form FI was obtained through a lyophilisation process using a lyophilizer 5 Pascal model LIO100P.

In particular, NaHDC mixture obtained according to the steps described above in points a) and b) is dissolved in deionized water at a temperature comprised between 30 and 40° C., obtaining a clear solution, which remains as such after 24 hours at a temperature of 25° C. The solution is then lyophilized at a constant temperature of −20° C. over a period of 72 hours, applying a pressure of $5\times10^{-2}$ mbar at the end of lyophilisation. Through this lyophilisation process the crystalline form FI of NaHDC is obtained as a very fine white crystalline solid. Such a crystalline form I of NaHDC was characterised through the analyses described above.

The polymorphic form FIII was obtained by dissolving NaHDC mixture obtained according to the steps described above in points a) and b) in deionized water at a temperature of 50° C. The clear solution obtained is slowly cooled to room temperature. A white precipitate is obtained that is filtered and dried in a stove at 230° C. for 15 hours. Such a precipitate was characterised as crystalline form III of NaHDC through the analyses described above.

The hydrated polymorphic form SI was obtained by dissolving NaHDC mixture obtained according to the steps described above in points a) and b) in deionized water at a temperature of 50° C. The clear solution obtained is slowly cooled to room temperature. A white precipitate is obtained that is filtered and left to dry for 24 hours in the air. Such a precipitate was characterised as crystalline form SI of NaHDC through the analyses described above.

The hydrated polymorphic form SII was obtained by leaving NaHDC mixture obtained according to the steps described above in points a) and b) at a constant temperature of 25° C. and at 90% relative humidity (RH) for two days.

Such a hydrated polymorphic form SII of NaHDC was characterised through the analyses described above.

The amorphous form of NaHDC was obtained by dissolving NaHDC mixture obtained according to the steps described above in points a) and b) in deionized water at room temperature.

The powder was obtained through nebulization and drying of the solution with a spray dryer Buchi mini spray dryer B-290.

It has also been observed that the hydrated polymorphic forms SI and SII interconvert into the polymorphic form FI by heating to a temperature of over 310° C.

It has also been observed, as shown in example 6, that the mixture of polymorphic form FI with the polymorphic form FII (1:1 weight/weight), through reprecipitation in ethyl acetate after 48 hours at room temperature (20-25° C.), completely converts into the polymorphic form FII. Said form is thus the most thermodynamically stable one at room temperature and up to 260° C., as already indicated above by the analyses shown.

The process of the present invention thus makes it possible to advantageously obtain the new polymorphic form FII of NaHDC that is pure both chemically and polymorphically.

An advantage of the present process is that of obtaining the polymorphic form FII of NaHDC with a defined particle size (granulometry) and optimal chemical-physical characteristics for the use of NaHDC as active pharmaceutical ingredient, particularly in the treatment and/or prevention of atherosclerotic disease.

Therefore, as already indicated above, no processes are necessary for homogenisation or to define the particle size that could alter the polymorphic form of interest.

The NaHDC powder polymorphic form FII obtained with the process of the present invention has a granulometry comprised between 25 μm and 425 μm, preferably between 25 μm and 250 μm and even more preferably between 75 μm and 250 μm.

In particular, 60-80% by weight of the NaHDC powder polymorphic form FII obtained with the process of the present invention has a granulometry comprised between 75

μm and 425 μm, 15-20% by weight has a granulometry of less than 250 μm and 95% by weight has a granulometry of over 25 μm.

The object of the present invention is thus the pharmaceutical compositions that comprise the polymorph FII of NaHDC, preferably for oral, parenteral, subcutaneous, intravenous, intramuscular, nasal, topical (for example transdermic or trans-mucosal) or rectal administration.

In particular, pharmaceutical forms for oral administration are preferred, like for example powders, granules, granulates, capsules, pills, boluses, tablets, caplets, cachets, liquid preparations, preferably in the form of solutions, syrups, suspensions, emulsions.

The compositions of the invention can comprise the polymorph FII of NaHDC together with one or more pharmaceutically acceptable excipients.

The polymorph FII of NaHDC is suitable for use in the treatment and/or prevention of atherosclerotic disease.

Therefore, a further object of the present invention are pharmaceutical formulations for use in the treatment and/or prevention of atherosclerotic disease, characterised by comprising the polymorphic form FII of NaHDC.

Materials and Methods

The thermal properties of the polymorphic forms described were obtained through differential scanning calorimetry (DSC). The DSC profiles were obtained with a heat flow instrument DSC 200 F3 Maia® (Netzsch). The DSC 200 F3 Maia® instrument was calibrated for temperature and enthalpy with an indium standard (melting point: 156.6° C.; ΔHf=28.45 Jg$^{-1}$). The samples were analysed according to the following conditions:

temperature range: 25-350° C.;
heating rate: 10° C./min;
sample-holder: perforated aluminium crucible;
gas: anhydrous nitrogen at a flow rate of 60 mL/min.

The loss of mass of the described polymorphic forms, due to the solvents and/or to the water ($H_2O$), was determined through thermo-gravimetric analysis (TGA) using a thermobalance TGA/DSC 1 Star$^e$ System Mettler Toledo. For each sample the % weight change was measured as a function of the temperature. The TGA/DSC 1 Star$^e$ System Mettler Toledo was calibrated for temperature with indium and aluminium.

The samples were analysed in the TGA/DSC according to the following conditions:

temperature range: 25-450° C.;
heating rate: 10° C./min;
sample-holder: perforated aluminium crucible;
gas: anhydrous nitrogen at a flow rate of 100 mL/min.

In order to determine the X-ray powder diffraction profiles (XPRD) a diffractometer Panalytical X'Pert Pro equipped with detector X'Celerator and X-ray tube (PW3373/00 Cu LFF DK312503) with current intensity 40 mA and voltage 40 kV was used. The instrument was calibrated with a silicon powder standard PANalytical640. The sample was positioned on a glass sample-carrier and analysed using the following parameters:

Scanning range(°): 3.0010-39.9997
Data acquisition range(°): 0.0167
Scanning mode: Continuous
Counter time (s): 12,700
soller slits (rad): 0.04
divergence slits: ¼
anti-scatter slits: ½

The IR spectra were obtained using a Nicolet FT-IR 6700 ThermoFischer spectrometer. The spectra were acquired in ATR mode on a ZnSe crystal with the following measurement parameters:

Number of scans per sample: 16
Resolution: 4.000
Number of scans per background: 16
Measurement range: 649.9-4000.2
Data acquisition range: 0.482124
Detector: DIGS KBr
DetectorBeamsplitter: KBr The Raman spectra were recorded on a FT-Raman Bruker MultiRam spectrometer equipped with a Ge-diode detector cooled with liquid nitrogen. The excitation source is a laser Nd3+–YAG (1064 nm) in the backscattering configuration (180°). The diameter of the focussed laser beam is about 100 μm and the spectral resolution is 4 cm$^{-1}$. The spectra were recorded with a laser power of about 60 mW.

To check the stability of the samples DVS (Dynamic vapour sorption) measurements were made using the DVS Intrinsic SMS instrument. The weight change of the sample associated with the change in humidity in a chamber at constant temperature was determined. Each sample was weighed in a range from 1 g to 4 g, with mass change equal to ±150 mg and mass resolution equal to ±0.1 μg, and positioned in the instrument and analysed at 25° C.±0.1 and 40° C.±0.1 in a relative humidity range comprised between 0% RH and 90% RH with increments of 10% RH, accuracy equal to ±1% RH. Moreover, the sample is brought from 0-90-0% RH with stages of 10% RH. The duration of these stages is as a function of the stabilization of the weight: if the weight change remains less than 0.002 dm (%)/dt (min) for 10 min, it goes on to the next stage. However, the stabilization for each stage cannot last more than 6 hours and in that case the instrument passes on to the next stage. The last stage contemplates the stabilization of the sample at 0% RH for 4 hours.

As an example, but not to limit the present invention, hereafter we give some Examples relating to the present invention.

EXAMPLES

Example 1

Preparation of NaHDC Polymorphic Form FII Through Reprecipitation in Acetone

Into a 2 liter jacketed reactor 900 ml of acetone (6 Volumes with respect to the dry solid loaded NaHDC mixture) is loaded, the mechanical stirrer is actuated setting the rate to 200 rpm and then 150 g (0.362 mol) of NaHDC mixture is slowly added. It is heated to the reflux temperature 56° C. and it is left under stirring for 4 hours.

A cooling ramp of 3 hours is used to bring the temperature of the mass from 56° C. to 25° C.

It is filtered on buckner and the white solid obtained is washed with 150 ml of a mixture of Acetone/water 80-20 v/v (1 Volume with respect to the dry solid loaded NaHDC mixture). The wet weight that is obtained is equal to 195.6 g, it is dried in an oven at 50° C. for 15 hours (in this case the solid does not soften during drying like in the case of obtaining NaHDC mixture)

The dry weight that is obtained is equal to 141.0 g which corresponds to a % yield w/w equal to 94.0% w/w and in mols of 93.9%.

The solid has a water content equal to 0.59% w/w. This solid was characterised as polymorphic form FII through the methods described in the text and in the figures of the present patent application.

Example 2

Preparation of NaHDC Polymorphic Form FII Through Reprecipitation in Methyl-Iso-Butyl Ketone (MIBK)

Into a 2 liter jacketed reactor 900 ml of methyl-iso-butyl ketone (MIBK) (6 Volumes with respect to the dry solid loaded NaHDC mixture) is loaded, the mechanical stirrer is actuated setting the rate to 200 rpm and then 150 g (0.362 mol) of NaHDC mixture is slowly added. It is heated to the reflux temperature 110° C. and it is left under stirring for 4 hours.

A cooling ramp of 3 hours is used to bring the temperature of the mass from 110° C. to 25° C.

It is filtered on buckner and the white solid obtained is washed with 150 ml of MIBK (1 Volume with respect to the dry solid loaded NaHDC mixture).

The wet weight that is obtained is equal to 188.2 g, it is dried in an oven at 50° C. for 15 hours (in this case the solid does not soften during drying like in the case of obtaining NaHDC mixture)

The dry weight that is obtained is equal to 140.3 g which corresponds to a % yield w/w equal to 93.5% w/w and in mols 93.4%.

The solid obtained is the polymorphic form FII and it has a water content equal to 0.5% w/w. This solid was characterised as polymorphic form FII through the methods described in the text and in the figures of the present patent application.

Example 3

Preparation of NaHDC Polymorphic Form FII Through Reprecipitation in Isopropyl Alcohol (2-Propanol)

Into a 2 liter jacketed reactor 900 ml of isopropyl alcohol (2-propanol—IPA) (6 Volumes with respect to the dry solid loaded NaHDC mixture) is loaded, the mechanical stirrer is actuated setting the rate to 200 rpm and then 150 g (0.362 mol) of NaHDC mixture is slowly added. It is heated to the reflux temperature 80° C. and it is left under stirring for 4 hours.

A cooling ramp of 3 hours is used to bring the temperature of the mass from 80° C. a 25° C.

It is filtered on buckner and the white solid obtained is washed with 150 ml of a IPA/$H_2O$ mixture 80-20 v/v (1 Volume with respect to the dry solid loaded NaHDC mixture). The water contained in the wash tends to dissolve the filtered solid (in this case the solid does not soften during drying like in the case of obtaining NaHDC mixture).

The wet weight that is obtained is equal to 128.0 g and it is dried in an oven at 50° C. for 15 hours.

The dry weight that is obtained is equal to 94.1 g which corresponds to a % yield w/w equal to 62.7% w/w and in mols 62.7%.

The solid obtained is the polymorphic form FII and it has a water content equal to 0.27% w/w. This solid was characterised as polymorphic form FII through the methods described in the text and in the figures of the present patent application.

Example 4

Preparation of NaHDC Polymorphic Form FII Through Reprecipitation in Ethyl Acetate (EtOAc)

Into a 2 liter jacketed reactor 900 ml of ethyl acetate (EtOAc) (6 Volumes with respect to the dry solid loaded NaHDC mixture) is loaded, the mechanical stirrer is actuated setting the rate to 200 rpm and then 150 g (0.362 mol) of NaHDC mixture is added slowly. It is heated to the reflux temperature 74° C. and it is left under stirring for 4 hours.

A cooling ramp of 3 hours is used to bring the temperature of the mass from 74° C. to 25° C.

It is filtered on buckner and the white solid obtained is washed with 150 ml of EtOAc (1 Volume with respect to the dry solid loaded NaHDC mixture).

The wet weight that is obtained is equal to 218.4 g and it is dried in an oven at 50° C. for 15 hours (in this case the solid does not soften during drying like in the case of obtaining NaHDC mixture).

The dry weight that is obtained is equal to 145.7 g which corresponds to a % yield w/w equal to 97.1% w/w and in mols 97.0%.

The solid obtained is the polymorphic form FII and it has a water content equal to 0.24% w/w. This solid was characterised as polymorphic form FII through the methods described in the text and in the figures of the present patent application.

Example 5

Preparation of NaHDC Polymorphic Form FII Through Reprecipitation in Acetonitrile (ACN)

Into a 2 liter jacketed reactor 900 ml of acetonitrile (ACN) (6 Volumes with respect to the dry solid loaded NaHDC mixture) is loaded, the mechanical stirrer is actuated setting the rate to 200 rpm and then 150 g (0.362 mol) of NaHDC mixture is added slowly. It is heated to the reflux temperature 80° C. and it is left under stirring for 4 hours.

A cooling ramp of 3 hours is used to bring the temperature of the mass from 80° C. to 25° C.

It is filtered on buckner and the white solid obtained is washed with 150 ml of ACN (1 Volume with respect to the dry solid loaded NaHDC mixture).

The wet weight that is obtained is equal to 226.2 g and it is dried in an oven at 50° C. for 15 hours (in this case the solid does not soften during drying like in the case of obtaining NaHDC mixture).

The dry weight that is obtained is equal to 146.2 g which corresponds to a % yield w/w equal to 97.5% w/w and in mols 97.5%.

The solid obtained is the polymorphic form FII and it has a water content equal to 0.47% w/w. This solid was characterised as polymorphic form FII through the methods described in the text and in the figures of the present patent application.

Example 6

Preparation of NaHDC Polymorphic Form FII Through Reprecipitation in Ethyl Acetate (EtOAc) of the Mixture Polymorphic Form FI and Polymorphic Form FII 1:1 (Weight/Weight) at Room Temperature (20-25° C.) for 48 Hours Into a 2 liter jacketed reactor 1000 ml of ethyl acetate (EtOAc) is loaded, the mechanical stirrer is actuated setting the rate to 200 rpm and then 25 g of polymorphic form FI and 25 g of polymorphic form FII are slowly added. It is left under stirring for 48 hours at a temperature of 25° C.

It is filtered on buckner and the white solid obtained is washed with 50 ml of EtOAc (1 Volume with respect to the loaded total dry solid NaHDC polymorphic form FI and NaHDC polymorphic form FII).

The wet weight that is obtained is equal to 75.1 g and it is dried in an oven at 50° C. for 15 hours (in this case the solid does not soften during drying like in the case of obtaining NaHDC mixture).

The dry weight that is obtained is equal to 48.5 g which corresponds to a % yield w/w equal to 97.0% w/w and in mols 96.7%.

The solid has a water content equal to 0.26% w/w.

Figure 61:
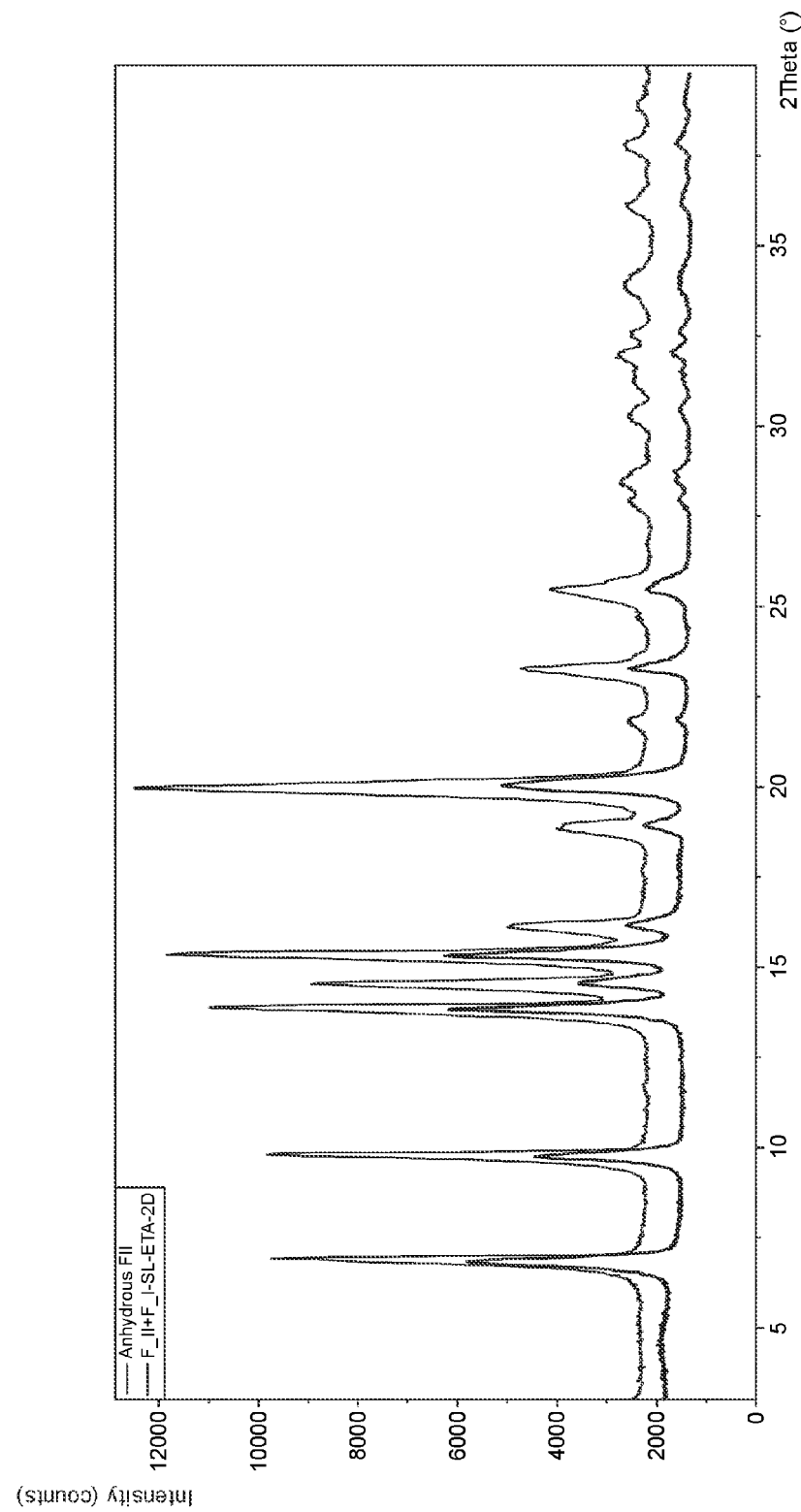
FIG. 61: shows the X-ray powder diffractogram (XPRD) of the polymorphic form FII of NaHDC obtained by mixing the polymorphic form FI of NaHDC and the polymorphic form FII of NaHDC in 1:1 ratio (w/w) after reprecipitation in ethyl acetate for 48 hours at a temperature of 25° C.

The powder analysed shows the XPRD pattern of the Anhydrous form FII (see FIGS. 61,62).

It has thus been demonstrated that in this way the polymorphic form FI interconverts into the polymorphic form FII, i.e. into the most thermodynamically stable form at room temperature.

Example 7

Preparation of NaHDC Mixture Through Reprecipitation in Anhydrous Acetone (3 Hours of Reflux and 3 Hours of Cooling)

Into a 2 liter jacketed reactor 300 ml of deionized water (2 Volumes with respect to the dry solid loaded NaHDC mixture) is loaded, the mechanical stirrer is actuated setting the rate to 180 rpm and then 150 g (0.362 mol) of NaHDC mixture is added slowly. It is heated to the temperature of 60° C. and it is left under stirring until the solid is completely dissolved. The yellowish viscous solution thus obtained is vacuum distilled until in the reactor there ends up being a highly viscous oily residue with a water content equal to 135 ml and an overall weight of 285 g.

The distillation temperature does not exceed 60° C. Once the distillation is complete, the temperature is lowered to 45°-50° C. and 900 ml of Acetone (6 Volumes with respect to the loaded dry solid NaHDC) is dripped in a time of 3 hours. It is heated to the reflux temperature equal to 56° C. and it is left under stirring for a time of 3 hours. A cooling ramp of 3 hours is used to bring the temperature of the mass from 56° C. to 25° C. It is filtered on buckner and the white solid obtained is washed with 150 ml of a mixture of Acetone/water 80-20 v/v (1 Volume with respect to the dry solid loaded NaHDC mixture).

The wet weight that is obtained is equal to 232.6 g and it is dried in an oven under vacuum at a temperature of 25° C. for 15 hours, it is increased to 30° C. for 4 hours and then to 50° C. for 15 hours.

The dry weight that is obtained is equal to 135.7 g which corresponds to a % yield w/w equal to 90.5% w/w and in mol 90.3%. The solid has a water content equal to 2.17% w/w. This solid is a mixture of the different polymorphic forms, as indicated in FIGS. 53-54-55-56-57-58-59-60.

Example 8

Preparation of NaHDC Mixture Through Reprecipitation in Anhydrous Acetone (30 Minutes of Reflux and 6 Hours of Cooling)

Into a 2 liter jacketed reactor 300 ml of deionized water (2 Volumes with respect to the dry solid loaded NaHDC mixture) is loaded, the mechanical stirrer is actuated setting the rate to 180 rpm and then 150 g (0.362 mol) of NaHDC mixture is added slowly. It is heated to a temperature of 60° C. and it is left under stirring until the solid is completely dissolved. The yellowish viscous solution thus obtained is vacuum distilled until in the reactor there ends up being a highly viscous oily residue with a water content equal to 135 ml and an overall weight of 285 g.

The distillation temperature does not exceed 60° C.

Once the distillation is complete, the temperature is lowered to 45° C.-50° C. and 900 ml of acetone (6 Volumes with respect to the loaded dry solid NaHDC) is dripped in a time of 3 hours. It is heated to the reflux temperature equal to 56° C. and it is left under stirring for a time of 30 minutes.

A cooling ramp of 6 hours is used to bring the temperature of the mass from 56° C. to 25° C.

It is filtered on buckner and the white solid obtained is washed with 150 ml of a mixture of Acetone/water 80-20 v/v (1 Volume with respect to the dry solid loaded NaHDC mixture).

The wet weight that is obtained is equal to 191.3 g and it is dried in an oven under vacuum at a temperature of 25° C. for 15 hours, increased to 30° C. for 4 hours and then to 50° C. or 15 hours.

The dry weight that is obtained is equal to 136.1 g which corresponds to a % yield w/w equal to 90.7% w/w and in mols 90.6%.

The solid, which has a water content equal to 2.13% w/w, is a mixture of the different polymorphic forms as indicated in FIGS. 53-54-55-56-57-58-59-60

Example 9

Comparative Example of Dynamic Vapour Sorption (DVS) Analysis in Isotherm at 25° C.±0.1 Between the Polymorphic Form FII and the Polymorphic Form FI In order to verify the stability of the samples DVS (Dynamic vapour sorption) measurements were carried out using the DVS Intrinsic SMS instrument. The weight change of the sample associated with the change in humidity in a chamber at constant temperature was determined. Each sample was positioned in the instrument and analysed at 25° C.±0.1 in a humidity range that ranges from 0% to 90% RH with increments of 10% RH, RH accuracy equal to ±1% RH. The sample is stabilized at 0% RH for 4 hours. The duration of the single stages is as a function of the stabilization of the weight: if the weight change remains less than 0.002 dm (%)/dt (min) for 10 min, it goes on to the next stage. The stabilization cannot last more than 6 hours and in that case it passes on to the next stage. The last stage contemplates the stabilization of the sample at 0% RH for 4 hours.

4 g of NaHDC polymorphic form FII are weighed accurately, mass change equal to ±150 mg and mass resolution equal to ±0.1 µg, and positioned in a chamber at a constant temperature of 25° C.±0.1, after which the weight change is recorded as the % relative humidity changes (RH). As can be seen from the graph in FIGS. 10 and 27 and from the values expressed in % in FIG. 11 the sample is surprisingly stable up to 70% RH. Indeed, in sorption at 25° C.±0.1 the polymorphic form FII is stable up to 70% RH (at 70% RH it shows a weight increase of less than 2%). After 70% RH it absorbs humidity and at 90% RH there is a weight change of about 35%.

Unlike the polymorphic form FI in sorption at 25° C., already at 30% RH the sample shows a weight change of about 2% and at 70% RH of 15%. At 90% RH there is a weight change of about 35%.

In desorption at 25° C.±0.1 the polymorphic form FII is stable up to 50% RH, preserving the weight change of about 34% (which corresponds to about 8 water molecules). At about 40% RH it is possible to see an inflection, and at this point the sample seems to still contain about 18% water (which corresponds to about 4 water molecules). At 0% RH the weight change is zero.

In desorption at 25° C.±0.1 the polymorphic form FI is stable up to 50% RH, preserving the weight change of about 34% (which corresponds to about 8 water molecules). At about 40% RH it is possible to see an inflection, and at this point the sample seems to still contain about 18% water (which corresponds to about 4 water molecules).

At 0% RH the weight change is zero.

From DVS analysis at 25° C.±0.1, the polymorphic form FI is less stable than the polymorphic form FII: the polymorphic form FII is stable in sorption at 25° C. up to about 70% RH, whereas the polymorphic form FI already at 20% RH shows a change in weight of about 2%, whereas at 70% RH it has an enormously higher increase, of about 15% water (see FIGS. 23,24,27).

Example 10

Comparative Example of Dynamic Vapour Sorption (DVS) Analysis in Isotherm at 40° C.±0.1 Between the Polymorphic Form FII and the Polymorphic Form FI To check the stability of the samples DVS (Dynamic vapour sorption) measurements were made using the DVS Intrinsic SMS instrument. The weight change of the sample associated with the change in humidity in a chamber at constant temperature was determined. Each sample is positioned in the instrument and analysed at 40° C.±0.1 in a humidity range from 0% to 90% RH with increments of 10% RH, RH accuracy equal to ±1% RH. The sample is stabilized at 0% RH for 4 hours. The duration of the single stages is as a function of the stabilization of the weight, if the weight change remains less than 0.002 dm (%)/dt (min) for 10 min, it goes on to the next stage. The stabilization cannot last more than 6 hours and in that case it passes on to the next stage. The last stage contemplates the stabilization of the sample at 0% RH for 4 hours.

4 g of NaHDC polymorphic form FII are weighed accurately, mass change equal to ±150 mg and mass resolution equal to ±0.1 μg, and positioned in a chamber at a constant temperature of 40° C.±0.1, after which the weight change is recorded as the % relative humidity changes (RH). As can be seen from the graph in FIGS. 12, 28 and from the values expressed in % in FIG. 13 the sample is surprisingly stable up to 70% RH. In sorption at 40° C.±0.1 the sample is stable up to 60% RH (at 70% RH it shows a weight increase of less than 2%). At 90% RH there is a weight change of about 45% (probably the sample becomes deliquescent). Unlike in sorption at 40° C.±0.1 the polymorphic form FI already at 30% RH, the sample shows a weight change of about 2% and at 70% RH of 8%.

At 90% RH there is a weight change of about 43%.

In desorption at 40° C.±0.1 the polymorphic form FII at 50-40% RH the curve shows a plateau probably at the solidification of the sample. At 0% RH the weight change is about 6%. In desorption at 40° C. the polymorphic form FI at 50-40% RH the curve shows a plateau and the sample shows a change in weight of about 17%.

At 0% RH the weight change is zero.

From DVS analysis at 40° C.±0.1, the form FI is less stable than the form FII: the form FII is stable in sorption up to about 70% RH, whereas the form FI already at 30% RH shows a change in weight of about 2%.

Example 11

Comparative Example of Dynamic Vapour Sorption (DVS) Analysis in Isotherm at 25° C.±0.1 Between the Polymorphic Form FII and NaHDC Mixture To check the stability of the samples DVS (Dynamic vapour sorption) measurements were made using the DVS Intrinsic SMS instrument. The weight change of the sample associated with the change in humidity in a chamber at constant temperature was determined. Each sample was positioned in the instrument and analysed at 25° C.±0.1 in a humidity range from 0% RH to 90% RH with increments of 10% RH, accuracy equal to ±1% RH. The sample is stabilized at 0% RH for 4 hours. The duration of the single stages is as a function of the stabilization of the weight: if the weight change remains less than 0.002 dm (%)/dt (min) for 10 min, it goes on to the next stage. The stabilization cannot last more than 6 hours and in that case it passes on to the next stage. The last stage contemplates the stabilization of the sample at 0% RH for 4 hours.

4 g/mg of NaHDC polymorphic form FII are weighed accurately, mass change equal to ±150 mg and mass resolution equal to ±0.1 μg, and positioned in a chamber at a constant temperature of 40° C.±0.1, and positioned in a chamber at a constant temperature of 25° C.±0.1, after which the weight change is recorded as the % relative humidity changes (RH). As can be seen from the graph in FIG. 10,58 and from the values expressed in % in FIG. 11 the sample is surprisingly stable up to 70% RH.

Indeed, in sorption at 25° C.±0.1 the polymorphic form FII is stable up to 70% RH (at 70% RH it shows a weight increase of less than 2%). After 70% RH it absorbs humidity and at 90% RH there is a weight change of about 35%. Unlike NaHDC mixture in sorption at 25° C.±0.1 already at 20% RH, the sample shows a weight change of about 3% and at 70% RH of 15%. At 90% RH there is a weight change of about 35%.

In desorption at 25° C.±0.1 the polymorphic form FII is stable up to 50% RH, preserving the weight change of about 34% (which corresponds to about 8 water molecules). At about 40% RH it is possible to see an inflection, and at this point the sample seems to still contain about 18% water (which corresponds to about 4 water molecules). At 0% RH the weight change is zero.

In desorption NaHDC mixture is stable up to 50% RH having a weight increase of about 34% (which corresponds to about 8 water molecules), and after about 40% RH it is possible to see an inflection and the sample seems to contain about 18% water (which corresponds to about 4 water molecules).

From DVS analysis at 25° C.±0.1, NaHDC mixture is less stable than the polymorphic form FII: the polymorphic form FII is stable in sorption at 25° C.±0.1 up to about 70% RH, whereas NaHDC mixture already at 20% RH shows a change in weight of about 3%, whereas at 70% RH it has an enormously higher increase, of about 15% water. (see FIGS. 56,57,58).

Example 12

Obtaining the Polymorphic Form FI

The form FI was obtained through a lyophilisation process.

A 5 Pascal model LIO100P lyophilizer was used.

5 g of NaHDC mixture was dissolved in 95 ml of deionized $H_2O$ at a temperature of 30-40° C., obtaining a clear solution that remains as such after a time of 24 hours at a temperature of 25° C.

The solution was lyophilized at a constant temperature of −20° C. in a time of 72 hours, applying a pressure of 5.10-2 mbar at the end of lyophilisation. A very fine crystalline white solid was obtained, which was characterised as polymorphic form FI through the methods described in the text and in the figures of the present patent application.

Example 13

Obtaining the Polymorphic Form FIII

The polymorphic form FIII was obtained by dissolving 1.5 g of NaHDC mixture in 3.5 ml of deionized $H_2O$ at a temperature of 50° C. The clear solution obtained was cooled slowly to a temperature of 25° C. A white precipitate was obtained that was filtered and dried in an oven at 230° C. for 15 hours.

Said precipitate was characterised as polymorphic form FIII through the methods described in the text and in the figures of the present patent application.

Example 14

Obtaining the Hydrated Polymorphic Form SI

The hydrated polymorphic form SI was obtained by dissolving 1.5 g of NaHDC mixture in 3.5 ml of deionized $H_2O$ at a temperature of 50° C. The clear solution was cooled slowly to room temperature of 25° C. A white precipitate was obtained that was filtered and left to dry for 24 hours in the air.

Said precipitate was characterised as hydrated polymorphic form SI through the methods described in the text and in the figures of the present patent application.

Example 15

Obtaining the Hydrated Polymorphic Form SII

The hydrated polymorphic form SII was obtained by leaving 1 g of NaHDC mixture in isotherm at room temperature of 25° C. and at 90% relative humidity (RH) for two days.

Example 16

Obtaining the Amorphous Form of NaHDC

The amorphous form was obtained by dissolving 2 g of NaHDC mixture in 500 ml of deionized $H_2O$ at room temperature. The powder was obtained through nebulization and drying of the solution using a spray dryer Buchi mini spray dryer B-290. An entry temperature of 140° C., an exit temperature of 60° C., an air flow of 473 L/h and a pump rate of 9 ml/min were applied.

The invention claimed is:

1. Sodium hyodeoxycholate in polymorphic form FII, characterised in that it has a powder X-ray diffraction spectrum having the following peaks ±0.20 degrees (2 theta): 6.94; 9.84; 13.92; 20.13; 23.30.

2. Sodium hyodeoxycholate (NaHDC) in polymorphic form FII, according to claim 1, having a DSC profile showing an endothermic peak at 260° C., with Peak onset at 263.5° C., Peak at 268.9° C. and enthalpy equal to 14.11 Joule/g.

3. Sodium hyodeoxycholate in polymorphic form FII, according to claim 1, characterised by a thermogravimetric profile wherein no significant losses of mass are observed up to 350° C.

4. Sodium hyodeoxycholate in polymorphic form FII, according to claim 1, having an FT-IR/ATR spectrum showing the following characteristic peaks at the following frequencies in FIG. 8: 3254.5; 2958.9; 2917.3; 2874.6; 2851.0; 1560.7; 1474.9; 1454.7; 1443.6; 1394.2; 1347.4; 1292.9; 1261.0; 1245.7; 1218.6; 1161.2; 1002.3 $cm^{-1}$, with a margin of error on the value indicated for each peak of ±1 $cm^{-1}$.

5. Sodium hyodeoxycholate in polymorphic form FII, according to claim 1, wherein the amount of water in the NaHDC crystal crystalline form FII is less than 1%, where said percentages refer to the total weight of the crystal.

6. Method for obtaining sodium hyodeoxycholate in polymorphic form FII, according to claim 1, comprising subjecting sodium hyodeoxycholate to reprecipitation by an organic solvent selected from a ketonic solvent, a solvent belonging to the category of esters, an alcohol, a solvent belonging to the category of nitriles or they mixture.

7. Method for obtaining sodium hyodeoxycholate in polymorphic form FII according to claim 6, wherein the ketonic solvent has chain $C_3$-$C_6$, the solvent belonging to the category of esters has chain $C_2$-$C_5$, the alcoholic solvent has chain $C_1$-$C_5$ and/or the solvent belonging to the category of nitriles has chain $C_2$-$C_3$.

8. Method for obtaining sodium hyodeoxycholate in polymorphic form FII according to claim 6, wherein the ketonic solvent is selected from acetone, methyl-iso-butyl ketone (MIBK), methyl-ethyl-ketone (MEK) or their mixtures, the solvent belonging to the category of esters is selected from ethyl acetate, ethyl formate, propyl acetate or their mixtures, the alcoholic solvent is selected from methanol, ethanol, 1-propyl alcohol (1-propanol), isopropyl alcohol (2-propanol), 1-butanol, 2-butanol, 2-pentanol or their mixtures, and/or the solvent belonging to the category of nitriles is selected from acetonitrile, propionitrile or their mixtures.

9. Method according to claim 6, wherein the reprecipitation takes place at a temperature comprised between 55-120° C.

10. Method according to claim 6, wherein the reprecipitation takes place in a time comprised between 6 and 10 hours.

11. Method according to claim 6, comprising the following steps:
   a) at least one purification step of hyodeoxycholic acid of formula II, carried out through preparation of a salt of an alkaline-earth metal of hyodeoxycholic acid and its subsequent acidification to obtain purified hyodeoxycholic acid;
   b) preparation of sodium hyodeoxycholate through treatment of purified hyodeoxycholic acid with NaOH up to pH comprised between 8.5 and 9.5;
   c) obtaining the polymorphic form FII of sodium hyodeoxycholate through reprecipitation by an organic solvent selected from a ketonic solvent, a solvent belonging to the category of esters, an alcohol, a solvent belonging to the category of nitriles or they mixture.

12. Method according to claim 11, wherein in step c) the ketonic solvent has chain $C_3$-$C_6$, the solvent belonging to the category of esters has chain $C_2$-$C_5$, the alcoholic solvent has chain $C_1$-$C_5$ and/or the solvent belonging to the category of nitriles has chain $C_2$-$C_3$.

13. Method according to claim 11, wherein in step c) the ketonic solvent is selected from acetone, methyl-iso-butyl ketone (MIBK), methyl-ethyl-ketone (MEK) or their mixtures, the solvent belonging to the category of esters is selected from ethyl acetate, ethyl formate, propyl acetate or their mixtures, the alcoholic solvent is selected from methanol, ethanol, 1-propyl alcohol (1-propanol), isopropyl alcohol (2-propanol), 1-butanol, 2-butanol, 2-pentanol or their mixtures, and/or the solvent belonging to the category of nitriles is selected from acetonitrile, propionitrile or their mixtures.

14. Method according to claim 11, wherein step c) is carried out at a temperature comprised between 55-120° C. and/or said step c) takes place in a time comprised between 6 and 10 hours, preferably between 6 and 8 hours.

15. Method according to claim 11, wherein the salt of an alkaline-earth metal of hyodeoxycholic acid is the magnesium salt of hyodeoxycholic acid, of formula III:

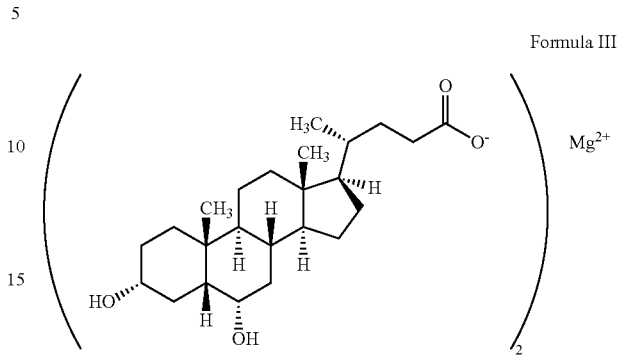

Formula III

16. Method according to claim 11, wherein step a) is repeated twice.

17. Method according to claim 16, wherein hyodeoxycholic acid of formula II obtained at the end of step a) has a chemical purity comprised between 99.5% and 99.9%.

18. Method according to claim 17, wherein sodium hyodeoxycholate obtained at the end of step b) has a chemical purity comprised between 99.5% and 99.9%.

19. Method according to claim 18, wherein sodium hyodeoxycholate polymorphic form FII obtained at the end of step c) has a chemical purity comprised between 99.5% and 99.9%.

20. Pharmaceutical compositions comprising sodium hyodeoxycholate in the crystalline polymorphic form FII as defined according to claim 1.

21. Pharmaceutical compositions according to claim 20, comprising sodium hyodeoxycholate in the polymorphic form FII with a granulometry comprised between 25 μm and 425 μm.

22. Pharmaceutical compositions according to claim 20, for oral, parenteral, subcutaneous, intravenous, intramuscular, nasal, topical (for example trans-dermic or trans-mucosal) or rectal administration.

* * * * *